US008663652B2

(12) United States Patent
Itescu

(10) Patent No.: US 8,663,652 B2
(45) Date of Patent: *Mar. 4, 2014

(54) REGENERATION OF ENDOGENOUS MYOCARDIAL TISSUE

(75) Inventor: Silviu Itescu, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 559 days.

This patent is subject to a terminal disclaimer.

(21) Appl. No.: 10/693,480

(22) Filed: Oct. 23, 2003

(65) Prior Publication Data

US 2004/0247564 A1 Dec. 9, 2004

Related U.S. Application Data

(63) Continuation-in-part of application No. PCT/US03/12768, filed on Apr. 23, 2003, which is a continuation-in-part of application No. 10/128,738, filed on Apr. 23, 2002, now abandoned.

(51) Int. Cl.
A61K 38/16 (2006.01)
A61K 38/18 (2006.01)
C07K 14/475 (2006.01)

(52) U.S. Cl.
USPC ...... 424/198.1; 514/16.4; 514/21.3; 530/300; 530/399

(58) Field of Classification Search
None
See application file for complete search history.

(56) References Cited

U.S. PATENT DOCUMENTS

| 5,008,284 | A | 4/1991 | Grover et al. |
| 5,061,620 | A | 10/1991 | Tsukamoto et al. |
| 5,451,399 | A | 9/1995 | Gimbrone, Jr. et al. |
| 5,552,381 | A | 9/1996 | Atkinson |
| 5,599,703 | A | 2/1997 | Davis et al. |
| 5,880,090 | A | 3/1999 | Hammond et al. |
| 5,980,887 | A | 11/1999 | Isner |
| 6,106,830 | A | 8/2000 | Li |
| 6,288,103 | B1 | 9/2001 | Faull et al. |
| 7,220,407 | B2 | 5/2007 | Mehta et al. |
| 7,473,425 | B2 | 1/2009 | Fukuda et al. |
| 7,507,705 | B2 | 3/2009 | Buschmann et al. |
| 7,662,392 | B2 * | 2/2010 | Itescu ................. 424/198.1 |
| 7,887,796 | B2 | 2/2011 | Itescu |
| 8,153,113 | B2 | 4/2012 | Itescu |
| 8,242,091 | B2 | 8/2012 | Itescu |
| 2002/0107195 | A1 | 8/2002 | Gupta |
| 2002/0115081 | A1 | 8/2002 | Lee et al. |
| 2003/0054418 | A1 | 3/2003 | Bodnar et al. |
| 2003/0054973 | A1 | 3/2003 | Anversa |
| 2003/0199464 | A1 | 10/2003 | Itescu |
| 2004/0131585 | A1 | 7/2004 | Itescu |
| 2005/0233992 | A1 | 10/2005 | Itescu |
| 2006/0051334 | A1 | 3/2006 | Kornowski |
| 2006/0057722 | A1 | 3/2006 | Kornowski |
| 2006/0111290 | A1 | 5/2006 | Itescu |
| 2007/0172467 | A1 | 7/2007 | Itescu |
| 2008/0057069 | A1 | 3/2008 | Itescu |
| 2009/0142296 | A1 | 6/2009 | Itescu |

FOREIGN PATENT DOCUMENTS

| EP | 0897980 A2 | 2/1999 |
| EP | 2292631 | 3/2011 |
| EP | 1290033 B1 | 10/2012 |
| JP | 06-287167 | 10/1994 |
| JP | 08-231595 | 9/1996 |
| WO | WO 98/19712 | 5/1998 |
| WO | WO 98/54210 | 12/1998 |
| WO | WO 99/17798 A1 | 4/1999 |
| WO | WO 99/18460 | 4/1999 |
| WO | WO 99/37751 | 7/1999 |
| WO | WO 99/37779 | 7/1999 |
| WO | WO 99/43839 | 9/1999 |
| WO | WO 99/45775 | 9/1999 |
| WO | WO 9937751 | 11/1999 |
| WO | WO 99/65507 | 12/1999 |
| WO | WO 00/57922 | 10/2000 |
| WO | WO 01/94420 | 12/2001 |
| WO | WO 02/16416 | 2/2002 |
| WO | WO 02036078 | 10/2002 |
| WO | WO 03047616 | 7/2003 |
| WO | WO 03/090512 | 11/2003 |

OTHER PUBLICATIONS

Tachibana et al. The chemokine receptor CXCR4 is essential for vascularization of the gastrointestinal tract. Nature 393: 591-594, 1998.*
Tews, TS. Apoptosis and muscle fibre loss in neuromuscular disorders. Neuromuscular Dis 12: 613-622, 2002.*
Woo, D. Apoptosis and loss of renal tissue in polycystic kidney diseases. New Engl J Med 333: 18-25, 1995.*
Canbay et al. Apoptosis and fibrosis in non-alcoholic fatty liver disease. Turk J Gastroenterol 16(1): 1-6, 2005.*
Behl et al. Apoptosis and Alzheimer's disease. J Neural Transm 107: 1325-1344, 2000.*

(Continued)

Primary Examiner — Bridget E Bunner
(74) Attorney, Agent, or Firm — John P. White; Cooper & Dunham LLP

(57) ABSTRACT

This invention provides a method of treating a disorder of a subject's heart involving loss of cardiomyocytes which comprises administering to the subject a composition comprising an amount of a human stromal derived factor-1 and an amount of a human granulocyte-colony stimulating factor, the composition being administered in an amount effective to cause proliferation of cardiomyocytes within the subject's heart so as to thereby treat the disorder. This invention also provides a method of treating a subject suffering from a disorder of a tissue involving loss and/or apoptosis of cells of the tissue which comprises administering to the subject a composition comprising an amount of an agent which induces phosphorylation and/or activation of protein kinase B, or an agent which induces phosphorylation and/or activation of an extracellular signal-regulated protein kinase, or an agent which induces activation of CXCR4.

9 Claims, 51 Drawing Sheets

(56) References Cited

OTHER PUBLICATIONS

Askari et al. Effect of stromal-cell-derived factor 1 on stem-cell homing and tissue regeneration in ischaemic cardiomyopathy. Lancet 362 : 697-703, 2003.*
Peled et al. The chemokine SDF-1 activates the integrins LFA-1, VLA-4, and VLA-5 on immature human CD34(+) cells: role in transendothelial/stromal migration and engraftment of NOD/SCID mice. Blood 95(11) : 3289-3296, 2000.*
Moore et al. Mobilization of endothelial and hematopoietic stem and progenitor cells by adenovector-mediated elevation of serum levels of SDF-1, VEGF, and angiopoietin-1. Ann NY Acad Sci 938: 36-47, 2001.*
Nagasawa et al. Role of chemokine SDF-1/PBSF and its receptor CXCR4 in blood vessel development. Ann NY Acad Sci 947: 112-116, 2001.*
Rempel et al. Identification and localization of the cytokine SDF1 and its receptor, CXC chemokine receptor 4, to regions of necrosis and angiogenesis in human glioblastoma. Clin Can Res 6 :102-111, 2000.*
Yamaguchi et al. Stromal cell-derived factor-1 effects on ex vivo expanded endothelial progenitor cell recruitment for ischemic neovascularization. Circulation 107: 1322-1328, 2003.*
Petit et al. The SDF-1-CXCR4 signaling pathway: a molecular hub modulating neo-angiogenesis. Trends in Immunol 28(7) : 299-307, 2007.*
Salcedo et al. Vascular endothelial growth factor and basic fibroblast growth factor induce expression of CXCR4 on human endothelial cells: In vivo neovascularization induced by stromal-derived factor-1alpha. Am J Pathol 154(4) : 1125-1135, 1999.*
Yu et al. Identification and expression of novel isoforms of human stromal cell-derived factor 1. Gene 374: 174-179, 2006.*
Watanabe et al. Effect of basic fibroblast growth factor on angiogenesis in the infarcted porcine heart. Basic Res Cardiol 93: 30-37, 1998.*
Stegman et al. Therapeutic angiogenesis: intramyocardial growth factor delivery of FGF-1 as sole therapy in patients with chronic coronary artery disease. Cardiac Vascul Regen 1: 259-267, 2000.*
Buja et al. Cardiomyocyte death and renewal in the normal and diseased heart. Cardiovasc Pathol 17(6): 349-374, 2008.*
Freedman et al. Therapeutic angiogenesis for coronary artery disease. Ann Internal Med 136: 54-71, Jan. 2002.*
Arenberg et al. In vitro and in vivo systems to assess role of c-x-c chemokines in regulation of angiogenesis. Meth Enzymol 288: 190-220, 1997.*
Belperio et al. CXC chemokines in angiogenesis. J Leukoc Biol 68: 1-8, 2000.*
"Heart Muscle" definition; www.medterms.com/script/main/art.asp?articlekey=9658; downloaded Mar. 5, 2013; 2 pages.*
"Myocardium" defintion; www.stedmans.online.com/context.aspx?id=mlrM2500001994&termtype=t; downloaded Mar. 5, 2013; 2 pages.*
"intramyocardial" definition; www.merriam-webster.com/medical/intramyocardial; downloaded Mar. 5, 2013; 1 page.*
Itescu et al. (2003) "Myocardial neovascularization by adult bone marrow-derived angioblasts: strategies for improvement of cardiomyocyte function" Heart Failure Rev 8: 253-258.
Itescu et al. (2003) "New directions in strategies using cell therapy for heart disease" J Mol Med 81: 288-296.
Noishiki et al. (1999) "Angiogenic growth factor release system for in vivo tissue engineering: a trial of bone marrow transplantation into ischemic myocardium" J Artif Organs 2: 85-91.
Orlic et al. (2001) "Mobilized bone marrow cells repair the infarcted heart, improving function and survival" Proc Natl Acad Aci USA 98(18):10344-10349.
Yin et al. (1997) "AC 133, A novel marker for human hematopoietic stem and progenitor cells" Blood 90(12):5002-5012.
Supplementary Partial European Search Report issued on Oct. 25, 2004 in connection with E.P. Application No. 01942041.3.
Lee et al. (1991) J. Biol. Chem. 266(24) 16188-16192.
Kajstura, Jan. et al. (1998) Myocyte proliferation in end-stage cardiac failure in humans, Proc. Natl. Acad. Sci. USA 95: 8801-8805.
Kalka, Christoph et al. (2000) Transplantation of ex vivo expanded endothelial progenitor cells for therapeutic neovascularization, PNAS 97: 3422-3427.
Kocher, A.A. et al. (2001) Neovascularization of ischemic myocardium by human bone-marrow-derived angioblasts prevents cardiomyocyte apoptosis, reduces remodeling and improves cardiac function, Nature Medicine 7: 430-436.
Beltrami, Antonio P. et al. (2001) Evidence That Human Cardiac Myocytes Divide after Myocardial Infarction, The New England Journal of Medicine 344: 1750-1757.
Asahara, Takayuki et al. (1999) VEGF contributes to postnatal neovascularization by mobilizing bone marrow-derived endothelial progenitor cells, EMBO Journal 18: 3964-3972.
Kawamoto, Atsuhiko et al. (2001) Therapeutic Potential of Ex Vivo Expanded Endothelial Progenitor Cells for Myocardial Ischemia, Circulation 103: 634-637.
Murohara, Toyoaki et al. (2000) Transplanted cord blood-derived endothelial precursor cells augment, postnatal neovascularization, The Journal of Clinical Investigation 105: 1527-1536.
Callard, Robin E. et al. (1994) The Cytokine FactsBook, Academic Press.
International Search Report issued Oct. 18, 2001 in connection with PCT/US01/18399.
European Search Report issued Apr. 26, 2004 in connection with E.P. 01942041.
International Search Report issued in connection with PCT/US03/12678, filed Apr. 23, 2002.
Futamatsu, H. et al. (2003), Cardiovascular Research, 59(1):95-105.
Stenhoff, J. et al. (2004), Biochem. Biophys. Res. Comm., 319(3):871-878.
Gupta, S. et al. (2002), Biochim. Biophys. Acta, 1589(3):247-260.
Placentini, L. et al. (2000), J. Mol. Cell. Cardiol., 32(4):565-567.
Okuno et al. (2000), Lab. Invest., 80(3):433-440.
Feucht, M. (1997), Am. J. Path., 151(5):1407-1416.
Asahara, T. et al. (1997), Science, 275:964-967.
Takahashi, T. et al. (1999), Nat. Med., 5:434-438.
Kennedy, M. et al. (1997), Nature, 386:488-493.
Choi, K.. et al. (1998), Development, 125:725-732.
Elefanty, A.G. et al. (1997), Blood, 90:1435-1447.
Shi, Q. et al. (1998), Blood, 92:362-367.
Lin, Y. et al. (2000), J. Clin. Invest., 105:71-77.
Tavian, M. et al. (1996), Blood, 87:67-72.
Jaffredo, T. et al. (1998), Development, 125:4575-4583.
Labastie, M.C. et al. (1998), Blood, 92:3624-3635.
Peichev, M. et al. (2000), Blood, 95:952-958.
Tsai, F.Y. et al. (1994), Nature, 371:221-225.
Asahara, T. et al. (1999), Circulation Research, 85:221-228.
Bhattachaya, et al. (2000), J. Vasc. Surgery, 32:116-123.
Dale, et al. (1993), Blood, 81:2496-2502.
De Revel, et al. (1994), Blood, 83(12):3795-3799.
Molineaux, et al. (1990), Blood, 76:2153-2158.
Möhle et al. (1998) "The Chemokine Receptor CXCR-4 Is Expressed on CD34+ Hematopoietic Progenitors and Leukemic Cells and Mediates . . . ," Blood 12:4523-4530.
Hattori, Koichi et al. (2001) "Plasma elevation of stromal cell-derived factor-1 induces mobilization of mature and immature hematopoietic progenitor and stem cells" Blood 97:3354-3360.
Lataillade, Jean-Jacques et al. (2000) "Chemokine SDF-1 enhances circulating CD34+ cell proliferation in synergy with cytokines: possible role in progenitor survival" Blood 95:756-768.
Jul. 29, 2005 Office Action issued in connection with U.S. Appl. No. 10/128,738.
Mar. 27, 2006 Office Action issued in connection with U.S. Appl. No. 10/220,554.
Mar. 27, 2002 Office Action issued in connection with U.S. Appl. No. 09/587,441.
Jan. 2, 2002 Office Action issued in connection with U.S. Appl. No. 09/587,441.
Sep. 19, 2001 Office Action issued in connection with U.S. Appl. No. 09/587,441.

(56) References Cited

OTHER PUBLICATIONS

Jan. 22, 2008 Office Action issued in connection with U.S. Appl. No. 11/234,879.
Aug. 14, 2007 Office Action issued in connection with U.S. Appl. No. 10/512,518.
Nov. 28, 2007 Office Action issued in connection with U.S. Appl. No. 11/648,769.
May 30, 2008 Office Action issued in connection with U.S. Appl. No. 10/512,518.
European Search Report issued on Aug. 28, 2008 in connection with European Patent Application No. EP03724217.9.
Sep. 26, 2008 Office Action issued in connection with U.S. Appl. No. 11/648,769.
Mar. 20, 2008 Communication Pursuant to Article 94(3) EPC in connection with European Patent Application No. EP01942041l.3.
International Search Report issued on Aug. 24, 2004 in connection with corresponding International Application No. PCT/US03/12768, filed Apr. 23, 2002.
Bonaros et al. (2008), "CCR3- and CXCR4-mediated Interactions Regulate Migration of CD34+ Human Bone Marrow . . . Repair." J. Thor. Cardio. Surg., 136(4):1044-1053.
Chavakis, E. (2006), "IL-8: A New Player in the Homing of Endothelial Progenitor Cells to Ischemic Myocardium." J. Mol. Cell. Cardiol. 40:442-445.
Janeway, et al. (1997), "Immunobiology: The Immune System in Health and Disease." NY: Current Biology Limited. 1:11-12.
Khachigian, LM, (2000), "Catalytic DNAs as Potential Therapeutic Agents and Sequence-Specific Molecular Tools . . . Function." J. of Clin Investigation 106(10):1189-1195.
Kocher, et al. (2006), "Myocardial Homing and Neovascularization by Human Bone Marrow Angioblasts is Regulated by IL-8/Gro CXC Chemokines." J. Mol. Cell. Cardiol. 40:455-464.
Lefer, et al. (1991), "Cardioprotective and Endothelial Protective Effects of [Ala-IL8] 77 in a Rabbit Model of Myocardial . . . Reperfusion." Br. J. Pharmacol.103:1152-1159.
Nishiyama, et al. (1999), "Identification of Thioredoxin-Binding Protein-2/Vitamin D3 Up-Regulated Protein 1 as a Negative Regulator of . . ."J Biol. Chem. 274(31):21645-21650.
Pak, J.H. et al. (2002), "An antisense Oligonucleotides to 1-cys Peroxiredoxin Causes Lipid Peroxidation and Apoptosis in Lung . . . Cells." J. Bio. Chem., 277(51):49927-49934.
Park, S. et al. (2000), "Antisense of Human Peroxiredoxin II Enhances Radiation-Induced Cell Death." Clin. Cancer. Research, 6:4915-4920.
Rinn, et al. (2006), "Anatomic Demarcation by Positional Variation in Fibroblast Gene Expression Programs." PLOS Genetics 2(7):1084-1096.
UniprotKB/Swiss-Prot P10145 (IL_8HUMAN), www.uniprot/ P10145. Last Modified May 26, 2009. Version 120.
Wang, L. (2000), "ACE Inhibitors and Beta Blockers Equally Attenuate Ischemia-Induced Reduction in Ventricular . . . Threshold." Exp. Clin. Cardiol. 5(2):82-86.
Xiang et al. 2005, Catalytic Degradation of Vitamin D Up-Regulated Protein 1 mRNA Enhances Cardiomyocytes Survival and Prevents Left Ventricula . . . J Biol Chem 280(47):39394-3.
Mar. 10, 2006 Official Action issued in connection with corresponding Chinese Patent Application No. 03814715.7.
Apr. 29, 2008 Official Action issued in connection with corresponding Israeli Patent Application No. 164671.
Nov. 20, 2008 Final Office Action issued in connection with co-pending U.S. Appl. No. 11/234,879.
Dec. 31, 2008 Office Action issued in connection with co-pending U.S. Appl. No. 11/894,555.
Feb. 12, 2009 Office Action issued in connection with co-pending U.S. Appl. No. 11/894,555.
Mar. 10, 2009 Office Action issued in connection with co-pending U.S. Appl. No. 10/512,518.
Mar. 13, 2009 Office Action issued in connection with co-pending U.S. Appl. No. 11/648,769.
Jun. 12, 2009 Office Action issued in connection with co-pending U.S. Appl. No. 11/894,581.
Jul. 9, 2009 Notice of Allowance and Fee(s) Due issued in connection with co-pending U.S. Appl. No. 11/234,879.
Mar. 12, 2009 Communication issued in connection with European Patent Application No. 03724217.9.
Mar. 3, 2009 Communication issued in connection with Japanese Patent Application No. 2003-587162.
Arai, A. et al. 1997, "Murine Cardiac Progenitor Cells Require Visceral . . . Streak for Terminal Differentiation." Developmental Dynamics, 210:344-353.
Junn, E. et al., "Vitamin D3 Up-Regulated Protein 1 Mediates Oxidative Stress Via Suppressing the Thioredoxin Function," J. Immunol., Jun. 2000; 164: 6287-6295.
Zhou, Y. et al. 2000, "Mouse Peroxiredoxin V is a Thioredoxin Peroxidase . . . Apoptosis." Biochemical and Biophysical Research Communications, 268, 1921-927.
Mar. 23, 2010 Office Action issued in connection with U.S. Appl. No. 11/894,555.
Hill et al. (2005) "Outcomes and Risks of Granulocyte Colony—Stimulating Factor in Patients with Coronary Artery Disease" Am coll Cardiol 46:1643-8.
Wang et al. (2005) "Effect of Mobilization of Bone Marrow Stem Cells by Granulocyte Colony Stimulating Factor on Clinical Symptoms, Left Ventricular Perfusion and Function in Patients with Severe Chronic Ischemic Heart Disease" Int J Cardiol 100:477-483.
Werneck-de-Castro et al. (2006) "G-CSF Does Not Improve Systolic Function in a Rat Model of Acute Myocardial infarction" Basic Res Cardiol 101:494-501.
Louzada et al. (2010) "Granulocyte-Colony Stimulating Factor Treatment of Chronic Myocardial Infarction" Cardiovasc Drugs Ther Feb. 2, 2010.
Srinivas et al. (2009) "Cytokines and Myocardial Regeneration" Cardiol Rev 17:1-9.
Tomikawa et al. (1993) "Warm Renal Ischemia and Reperfusion Injury in Rats Treated with Cyclophosphamide and/or Granulocyte Colony—Stimulating Factor" Transplant Proc 25(6): 3230-3.
Leong et al. (2000) "Neutrophil-independent Protective Effect of r-metHuG-CSF in Ischaemia-reperfusion Injury in Rat Skeletal Muscle" Int J Exp Path 81:41-49.
Sullivan et al. (1993) "Effects of Perioperative Granulocyte Colony—stimulating Factor on Horses with Ascending Colonic Ischemia" Vet Surg 22(5):343-350.
Squadrito et al. (1997) "The effects of Recombinant Human Granulocyte-colony Stimulating Factor on Vascular Dysfunction and Splanchnic Ischaemia-reperfusion Injury" Brit J Pharmacol 120:333-9.
Phillips, A.J (2001) The Challenge of Gene Therapy and DNA Delivery J Pharm Pharmacol 53:1169-74.
Apr. 28, 2010 Office Action issued in connection with Mexican Patent Application No. Pa/a/2002/012067.
Jun. 23 2010 Office Action issued in connection with U.S. Appl. No. 11/894,581.
Wheeler et al. (1988) "Cultured Human Endothelial Cells Stimulated with Cytokines or Endotoxin Produce an Inhibitor of Leukocyte Adhesion" J Clin Invest 82: 1211-1218.
Gimbrone et al. (1989) "Endothelial Interleukin-8: a Novel Inhibitor of Leukocyte-endothelial Interactions" Science 246:1601-03.
Hebert et al. (1990) Endothelial and Leukocyte Forms of IL-8 J Immunol 145:3033-40.
De Simoni et al. (2008) "Silencing of peroxiredoxin 3 and peroxiredoxin 5 reveals the role of mitochondrial peroxiredoxins in the protection of human neuroblastoma SH-SY5Y cells toward MPP+" Neuroscience Letters 433:219-224.
Chang et al. (2002) "Regulation of peroxiredoxin I activity by Cdc2-mediated phosphorylation" J Biol Chem. 277:25370-6.
Aug. 3, 2010 Official Action issued in connection with Japanese Patent Application No. 2003-587162.
May 26, 2010 Official Action issued in connection with European Patent Application No. EP01942041.3.
Berk, B. (2007), "Novel Approaches to Treat Oxidative Stress and Cardiovascular Disease," Tans. Am. Clin. Clim. Assoc., 118:209-214.

(56) References Cited

OTHER PUBLICATIONS

Prosperi et al. (1993), "A Human cDNA Corresponding to a Gene Overexpressed during Cell Proliferation Encodes a Product . . . " J. Biol. Chem., 268(15):11050-11056.
Smith, W. (1991), "Interleukin-8 induces Neutrophil Transendothelial Migration," Immunology 72:65-72.
Takahashi et al. (1995) "Effects of Endothelial Interleukin-8 on Neutrophol Migration Across an Endothelial Monolayer," Cardiovasc Res 29:670-675.
Kang et al. (1998) "Mammalian Peroxiredoxin Isoforms can Reduce Hydrogen Peroxide Generated in Response to Growth . . . ," Journal of Biological Chemistry 273(11):6297-6302.
Zhang et al. (1997) "Thioredoxin Peroxidase in a Novel Inhibitor of Apoptosis with a Mechanism Distinct from that of BCL-2," Journal of Biological 272(49):30615-8.
Berggren et al. (2001) "Thioredoxin Peroxidase-1 (Peroxiredoxin-1) is Increased in Thioredoxin-1 Transfected Cells . . . ," Archives of Biochemistry and Biophysics 392(1):103-9.
Song et al. (2003) "Vitamin D3 Up-regulating Protein 1 (VDUP1) Antisense DNA Regulates Tumorigenicity and Melanogenesis . . . " Immunol Lett 86:235-247.
Perrone et al. (2009) "Thioredoxin Interacting Protein (TXNIP) Induces Inflammation Chromatin Modification in Retinal Capillary Endothelial . . . " J Cell Physiol 221:262-272.
Weber et al. (2000) "Fibrosis and Hypertensive Heart Disease" Curr Opin Cardiol 15:264-272.
Dec. 23, 2009 Final Office Action issued in connection with U.S. Appl. No. 11/894,581.
Dec. 29, 2009 Final Office Action issued in connection with U.S. Appl. No. 11/648,769.
Jan. 28, 2010 Office Action issued in connection with U.S. Appl. No. 10/512,518.
Terui et al. (1998) "Activated Endothelial Cells Induce Apoptosis in Leukemic Cells by Endothelial Interleukin-8" Blood 92:2672-80.
Terui et al. (1999) "NH2-terminal Pentapeptide of Endothelial Interleukin 8 is Responsible for the Induction of Apoptosis in leukemic Cells . . . " Cancer Research 59:5651-5.
Boyle et al. (1998) "Inhibition of Interleukin-8 Blocks Myocardial Ischemia-Reperfusion Injury", J Thoracic and Cardiovascular Surgery 116: 114-121.
Damas et al. (2000) "CXC-Chemokines, A New Group of Cytokines in Congestive Heart Failure—Possible Role of Platelets and Monocytes", Cardiovascular Research 45:428-436.
Higuchi et al. (2009) "Direct Injection of Kit Ligand-2 Lentivirus Improves Cardiac Repair and Rescues Mice Post-myocardial Infarction" Mol. Ther. 17:262-268.
Himmelmann et al. (1999) "New Information on the Role of Beta-blockers in Cardiac Therapy", Cardiovasc Drugs Therapy, 13:469-477.
Jayasankar et al. (2004) "Targeted Overexpression of Growth Hormone by Adenoviral Gene Transfer Preserves Myocardial Function and Ventricular Geometry in Ischemiccardiomyopathy" J Mal Cell Cardiol. 36:531-538.
Schuster et al. (2002) "Stromal Derived Growth Factor (SDF)-1 Augments Myocardial Neovascularization and Cardiomyocyte Regeneration Induced by Human Bone Marrow Angioblasts" Circulation 106 (19 Supplement): II-65, Nov. 2002.
Tendera et al. (2005) "Clinical Trials Using Autologous Bone Autologous Bone Marrow and Peripheral Blood-derived Progenitor Cells in Patients With Acute Myocardial Infarction", Folia Histiochemica Cytobiol, 43(4):233-235.
Walter et al. (2002) "Endothelial Progenitor Cell: Regulation and Contribution to Adult Neovascularization", Herz, 27:579-588.
Zampetaki et al. (2008), "Vascular Repair by Endothelial Progenitor Cells", Cardiovasc Res 78:413-421.
Oct. 7, 2010 Official Action issued in connection with Canadian Patent Application No. 2,412,436.
Mar. 18, 2011 Office Action issued in connection with U.S. Appl. No. 11/894,581.
Dec. 7, 2010 Office Action issued in connection with U.S. Appl. No. 11/894,555.
Feb. 16, 2011 Office Action issued in connection with U.S. Appl. No. 12/657,264.
Jun. 8, 2011 Office Action issued in connection with U.S. Appl. No. 12/657,264.
Feb. 23, 2011 Official Action issued in connection with European Patent Application No. EP01942041.3.
Apr. 26, 2011 European Search Report and Opinion issued in connection with European Patent Application No. EP10012751.1.
Oct. 12, 2010 Notice of Allowance issued in connection with U.S. Appl. No. 10/512,518.
Nov. 17, 2010 Official Action issued in connection with Canadian Patent Application No. 2,482,996.
Feb. 7, 2011 Communication issued in connection with European Patent Application No. EP10164397.1.
Extended European Search Report issued in connection with Patent Application No. EP10164397.1, Feb. 7, 2011.
Mar. 14, 2011 Communication Pursuant to Rules 70(2) and 70a(2) EPC and Reference to Rule 39(1) EPC issued in connection with European Patent Application No. EP10164397.1.
Jan. 26, 2011 Office Action issued in connection with Israeli Patent Application No. 164671.
Apr. 5, 2011 Decision of Dismissal of Amendment and Decision of Rejection issued in connection with Japanese Patent Application No. 2003-587162.
Donath et al. (1998) "Acute Cardiovascular Effects of Insulin-Like Growth Factor I in Patients With Chronic Heart Failure" J. Clin. Endo. and Metabolism, 83:3177-3183.
Lee et al. (1999) "Insulin-Like Growth Factor I Improves Cardiovascular Function and Suppresses Apoptosis of Cardiomyocytes in Dilated Cardiomyopathy" Endocrinology 140:4831-4840.
Saitoh et al. (2001) "Rapid Induction and Ca2+ Influx-Mediated Suppression of Vitamin D3 Up-regulated Protein 1 (VDUP1) mRNA in Cerebellas Granule Neurons Undergoing Apoptosis" J. Neurochem. 78:1267-1276.
Dec. 8, 2011 Notice of Allowance issued in connection with U.S. Appl. No. 11/894,581.
Aug. 23, 2011 Summons to Attend Oral Proceedings issued in connection with European Patent Application No. EP01942041.3.
Nov. 17, 2011 Second Summons to Attend Oral Proceedings issued in connection with European Patent Application No. EP01942041.3.
Jun. 28, 2011 Official Action issued in connection with Japanese Patent Applications No. 2002-501968.
Jan. 4, 2012 Office Action issued in connection with U.S. Appl. No. 11/648,769.
Sep. 6, 2011 Examination Report issued in connection with Australian Patent Application No. 2009213032.
Nov. 15, 2011 Examination Report issued in connection with Australian Patent Application No. 2009213032.
Extended European Search Report issued in connection with European Patent Application No. EP11157749.0.
Norrby (1996) "Interleukin-8 and de novo Mammalian Angiogenesis" Cell Prolif. 29:315-323.
Yanagisawa-Miwa et al. (1992) "Salvage of Infarcted Myocardium by Angiogenic Action of Basic Fibroblast Growth Factor" Science 257:1401-1403.
Feb. 3, 2012 Official Action issued in connection with Canadian Patent Application No. 2,412,436.
Mar. 21, 2012 Issue Notification issued in connection with U.S. Appl. No. 11/894,581.
Aug. 22, 2012 Final Office Action issued in connection with U.S. Appl. No. 11/894,555.
Jun. 27, 2012 Office Action issued in connection with U.S. Appl. No. 12/657,264.
Mar. 14, 2012 Brief Communication issued in connection with European Patent Application No. EP01942041.3.
May 10, 2012 Communication Under Rule 71(3) EPC issued in connection with European Patent Application No. EP01942041.3.

(56) References Cited

OTHER PUBLICATIONS

Oct. 5, 2012 Decision to Grant a European Patent Pursuant to Article 97(1) EPC issued in connection with European Patent Application No. EP01942041.3.
Oct. 31, 2012 Transmission of a Certificate for a European Patent Pursuant to Rule 74 EPC issued in connection with European Patent Application No. EP01942041.3.
Apr. 24, 2012 Official Action issued in connection with Japanese Patent Applications No. 2002-501968.
Apr. 12, 2012 Notice of Allowance issued in connection with U.S. Appl. No. 11/648,769.
Apr. 26, 2012 Communication issued in connection with U.S. Appl. No. 11/648,769.
Jul. 25, 2012 Issue Notification issued in connection with U.S. Appl. No. 11/648,769.
Feb. 22, 2013 Office Action issued in connection with Canadian Patent Application 2,482,996.
Oct. 30, 2012 Office Action issued in connection with Japanese Patent Application No. 2011-021983.
Extended European Search Report issued in connection with European Patent Application No. EP11157749.0, Aug. 29, 2011.

* cited by examiner

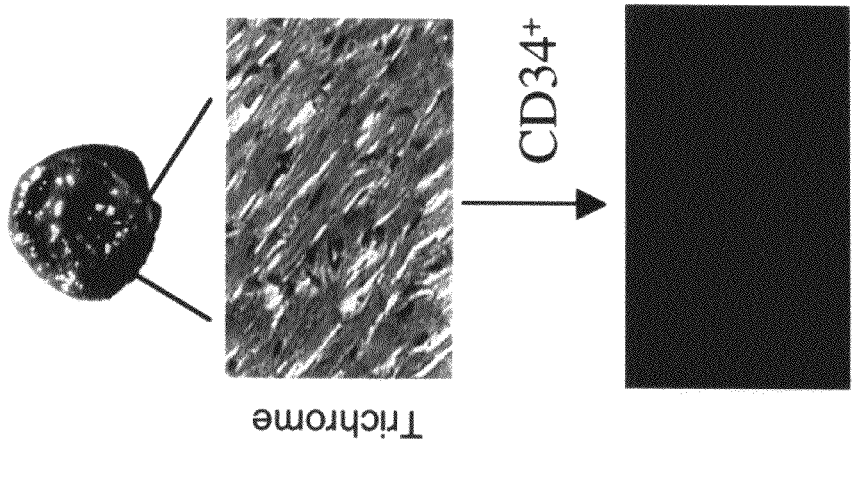
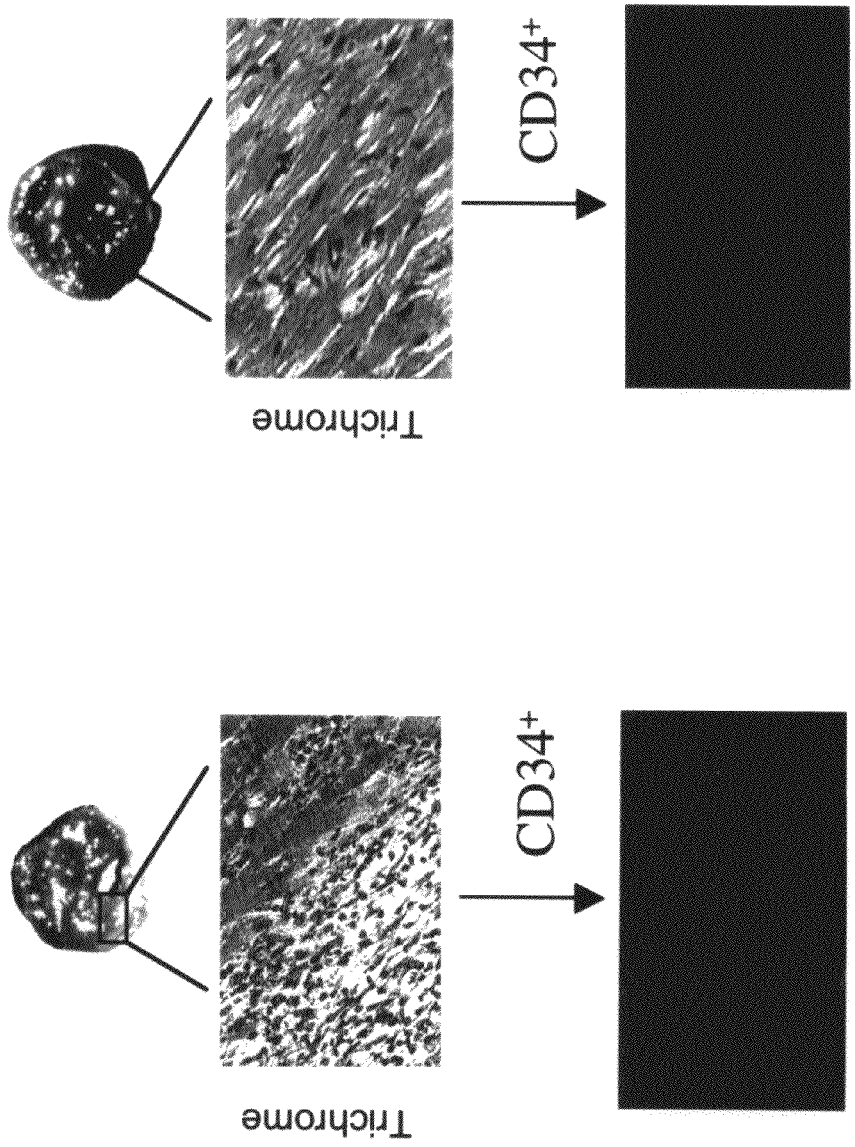
FIGURE 1A

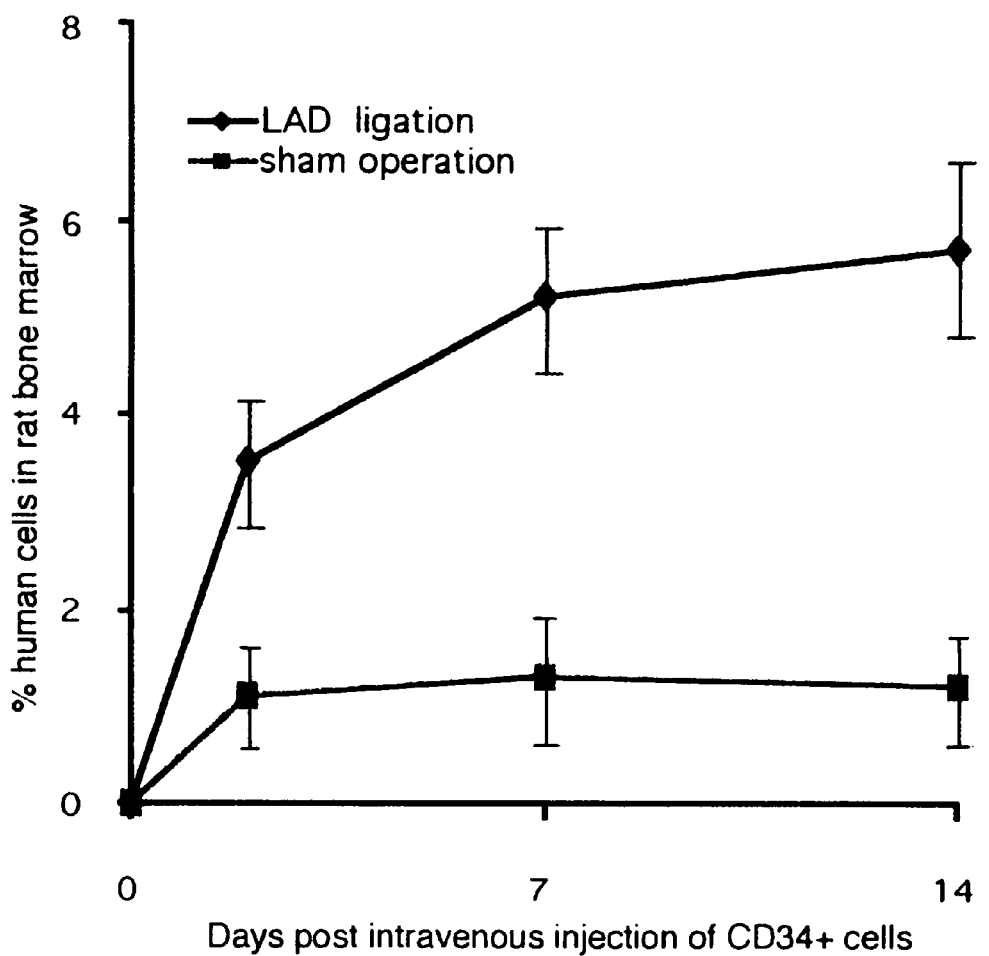

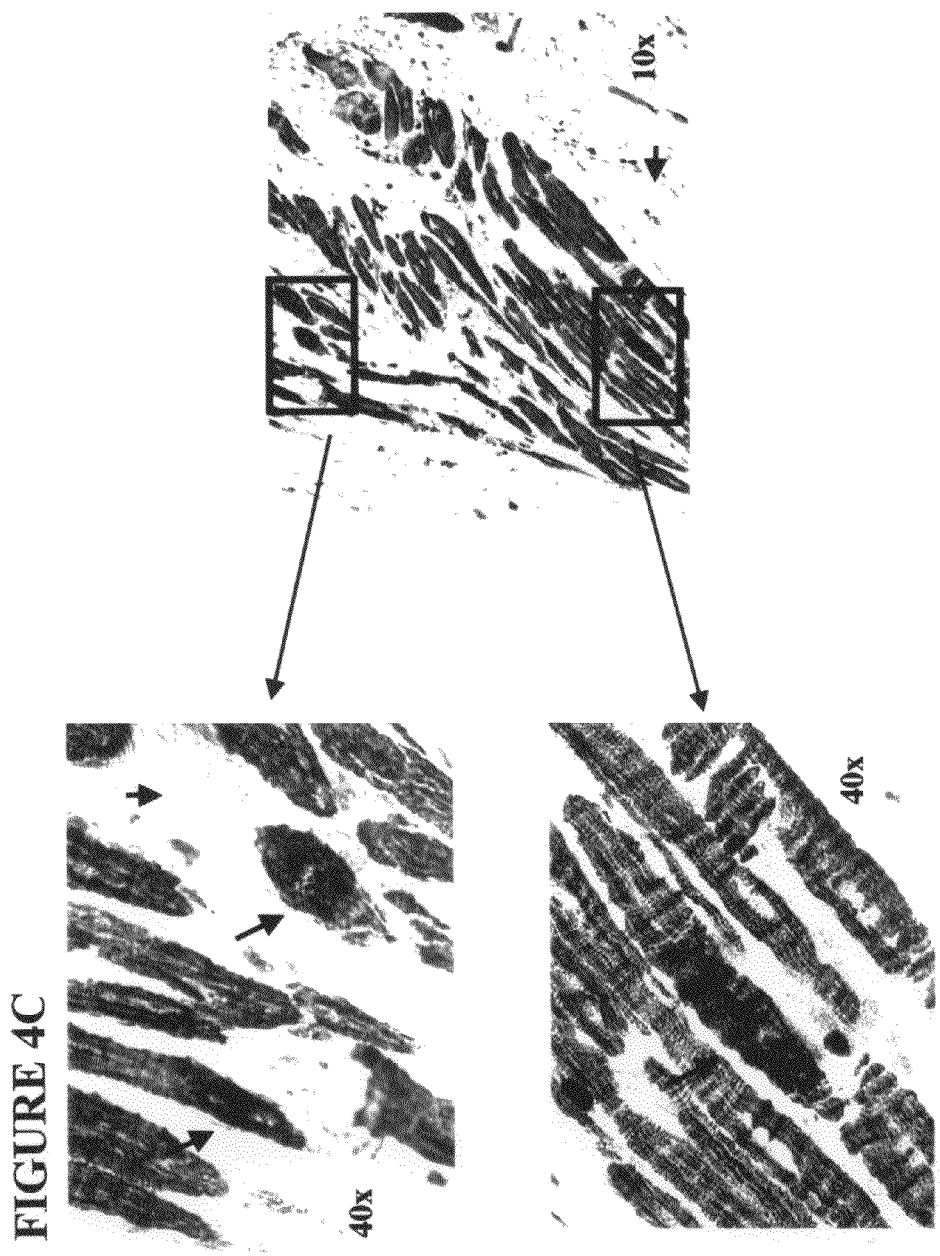

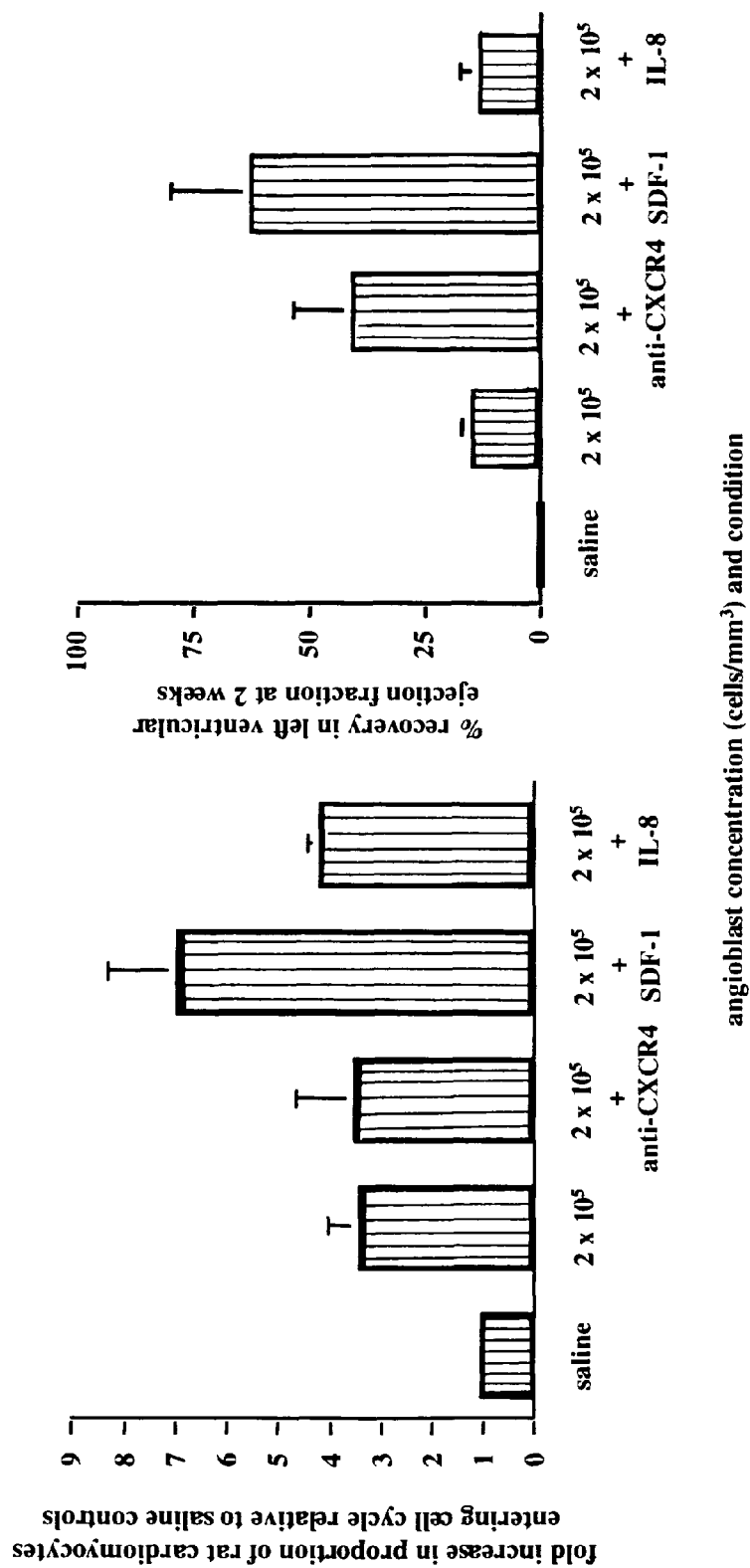

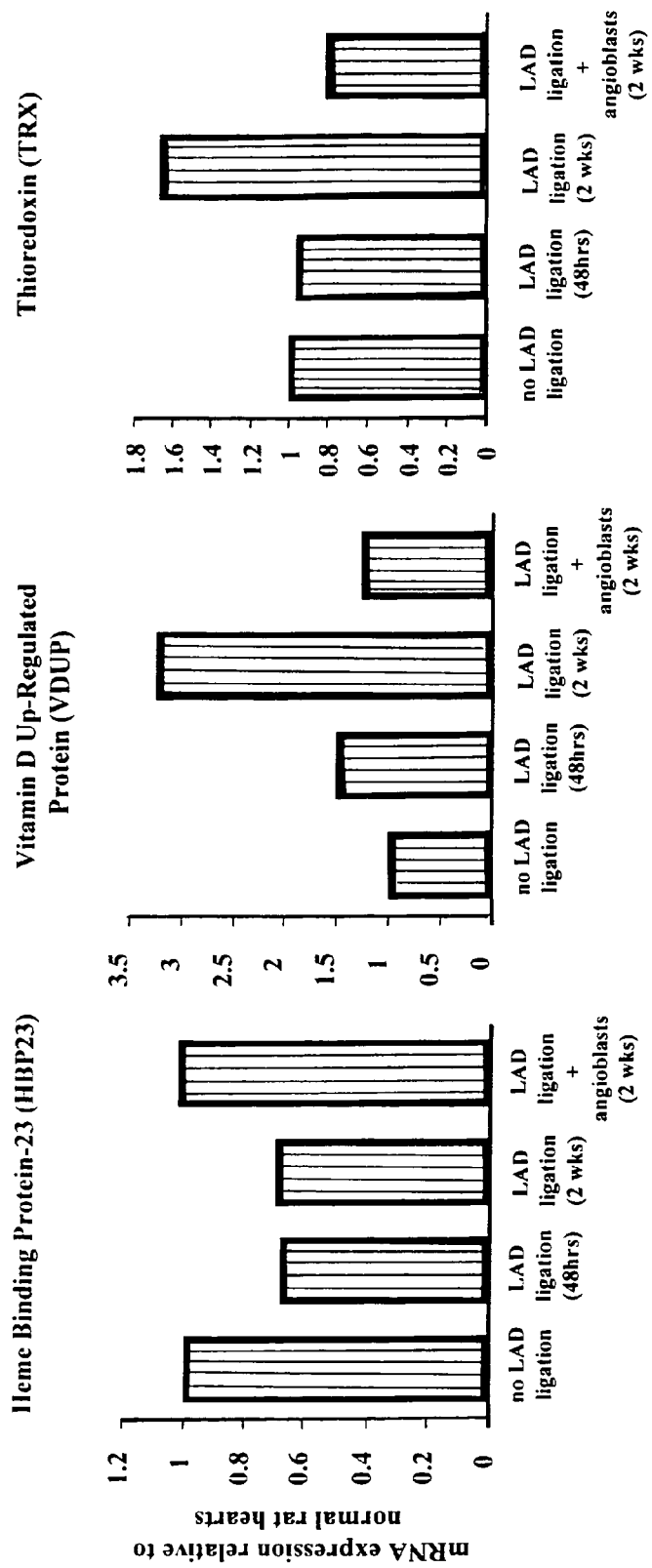

FIGURE 6

```
   1 aaactaaccc ctcttttcct ccaaaggagt gcttgtggag atcggatctt ttctccagca
  61 attgggggaa agaaggcttt ttctctgact tcgcttagtg taaccagcgg cgtatatttt
 121 ttaggcgcct tttcgaaaac ctagtagtta atattcattt gtttaaatct tatttattt
 181 ttaagctcaa actgcttaag aataccttaa ttccttaaag tgaaataatt ttttgcaaag
 241 gggtttcctc gatttggagc ttttttttc ttccaccgtc atttctaact cttaaaacca
 301 actcagttcc atcatggtga tgttcaagaa gatcaagtct tttgaggtgg tctttaacga
 361 ccctgaaaag gtgtacggca gtggcgagaa ggtggctggc cgggtgatag tggaggtgtg
 421 tgaagttact cgtgtcaaag ccgttaggat cctggcttgc ggagtggcta aagtgctttg
 481 gatgcaggga tcccagcagt gcaaacagac ttcggagtac ctgcgctatg aagacacgct
 541 tcttctggaa gaccagccaa caggtgagaa tgagatggtg atcatgagac ctggaaacaa
 601 atatgagtac aagttcggct ttgagcttcc tcaggggcct ctgggaacat ccttcaaagg
 661 aaaatatggg tgtgtagact actgggtgaa ggcttttctt gaccgcccga gccagccaac
 721 tcaagagaca aagaaaaact ttgaagtagt ggatctggtg gatgtcaata cccctgattt
 781 aatggcacct gtgtctgcta aaaagaaaa gaaagtttcc tgcatgttca ttcctgatgg
 841 gcgggtgtct gtctctgctc gaattgacag aaaaggattc tgtgaaggtg atgagatttc
 901 catccatgct gactttgaga atacatgttc ccgaattgtg gtccccaaag ctgccattgt
 961 ggcccgccac acttaccttg ccaatggcca gaccaaggtg ctgactcaga agttgtcatc
1021 agtcagaggc aatcatatta tctcagggac atgcgcatca tggcgtggca agagccttcg
1081 ggttcagaag atcaggcctt ctatcctggg ctgcaacatc cttcgagttg aatattcctt
1141 actgatctat gttagcgttc ctggatccaa gaaggtcatc cttgacctgc ccctggtaat
1201 tggcagcaga tcaggtctaa gcagcagaac atccagcatg ccagccgaa ccagctctga
1261 gatgagttgg gtagatctga acatccctga tacccagaa gctcctccct gctatatgga
1321 tgtcattcct gaagatcacc gattggagag cccaaccact cctctgctag atgacatgga
1381 tggctctcaa gacagcccta tctttatgta tgccctgag ttcaagttca tgccaccacc
1441 gacttatact gaggtggatc cctgcatcct caacaacaat gtgcagtgag catgtggaag
1501 aaaagaagca gcttaccta cttgtttctt tttgtctctc ttcctggaca ctcactttt
1561 cagagactca acagtctctg caatggagtg tgggtccacc ttagcctctg acttcctaat
1621 gtaggaggtg gtcagcaggc aatctcctgg gccttaaagg atgcggactc atcctcagcc
1681 agcgcccatg ttgtgataca ggggtgtttg ttggatgggt ttaaaaataa ctagaaaaac
1741 tcaggcccat ccatttctc agatctcctt gaaaattgag gccttttcga tagtttcggg
1801 tcaggtaaaa atggcctcct ggcgtaagct tttcaaggtt ttttggaggc ttttgtaaa
1861 ttgtgatagg aactttggac cttgaactta cgtatcatgt ggagaagagc caatttaaca
1921 aactaggaag atgaaaaggg aaattgtggc caaaactttg ggaaaggag gttcttaaaa
1981 tcagtgtttc ccctttgtgc acttgtagaa aaaaagaaa aaccttctag agctgatttg
2041 atggacaatg gagagagctt tccctgtgat tataaaaaag gaagctagct gctctacggt
2101 catctttgct taagagtata cttttaaacctg gcttttaaag cagtagtaac tgccccacca
2161 aaggtcttaa aagccatttt tggagcctat tgcactgtgt tctcctactg caaatatttt
2221 catatgggag gatggttttc tcttcatgta agtccttgga attgattcta aggtgatgtt
2281 cttagcactt taattcctgt caaattttt gttctcccct tctgccatct taaatgtaag
2341 ctgaaactgg tctactgtgt ctctagggtt aagccaaaag acaaaaaaa ttttactact
2401 tttgagattg ccccaatgta cagaattata taattctaac gcttaaatca tgtgaaaggg
2461 ttgctgctgt cagccttgcc cactgtgact tcaaacccaa ggaggaactc ttgatcaaga
2521 tgcccaaccc tgtgatcaga acctccaaat actgccatga gaaactagag ggcaggtctt
2581 cataaaagcc ctttgaaccc ccttcctgcc ctgtgttagg agatagggat attggcccct
2641 cactgcagct gccagcactt ggtcagtcac tctcagccat agcactttgt tcactgtcct
2701 gtgtcagagc actgagctcc accctttct gagagttatt acagccagaa agtgtgggct
2761 gaagatggtt ggtttcatgt
```

FIGURE 7

```
 314                   ATggtgA Tgttcaagaa gATcaagtct tttgaggtgg tctttaacga
 361 ccctgaaaag gtgtacggca gtggcgagaa ggtggctggc cgggtgATag tggaggtgtg
 421 tgaagttact cgtgtcaaag ccgttaggAT cctggcttgc ggagtggcta aagtgctttg
 481 gATgcagggA Tcccagcagt gcaaacagac ttcggagtac ctgcgctATg aagacacgct
 541 tcttctggaa gaccagccaa caggtgagaA TgagATggtg ATcATgagac ctggaaacaa
 601 ATATgagtac aagttcggct ttgagcttcc tcaggggcct ctgggaacAT ccttcaaagg
 661 aaaATATggg tgtgtagact actgggtgaa ggcttttctt gaccgcccga gccagccaac
 721 tcaagagaca aagaaaaact ttgaagtagt ggATctggtg gATgtcaATa ccctgATtt
 781 aATggcacct gtgtctgcta aaaaagaaaa gaaagtttcc tgcATgttcA TtcctgATgg
 841 gcgggtgtct gtctctgctc gaATtgacag aaaaggATtc tgtgaaggtg ATgagATttc
 901 cATccATgct gactttgaga ATacATgttc ccgaATtgtg gtccccaaag ctgccATtgt
 961 ggcccgccac acttaccttg ccaATggcca gaccaaggtg ctgactcaga agttgtcATc
1021 agtcagaggc aATcATATtA Tctcagggac ATgcgcATcA Tggcgtggca agagcctcg
1081 ggttcagaag ATcaggcctt ctATcctggg ctgcaacATc cttcgagttg aATATtcctt
1141 actgATctAT gttagcgttc ctgATccaa gaaggtcATc cttgacctgc ccctggtaAT
1201 tggcagcagA Tcaggtctaa gcagcagaac ATccagcATg gccagccgaa ccagctctga
1261 gATgagttgg gtagATctga acATcccctgA Tacccagag gctcctccct gctATATggA
1321 TgtcATtcct gaagATcacc gATtggagag cccaaccact cctctgctag ATgacATggA
1381 Tggctctcaa gacagccctA TcttATgtA Tgcccctgag ttcaagttcA Tgccaccacc
1441 gacttATact gaggtggATc cctgcATcct caacaacaAT gtgcagtga
```

FIGURE 8

```
 314                   atggtga tgttcaagaa gatcaagtct tttgaggtgg tctttaacga
 361 cctgaaaag gtgtacgGCa gtgGCgagaa ggtgGCtgGC cgggtgatag tggaggtgtg
 421 tgaagttact cgtgtcaaaG Ccgttaggat cctgGCttGC ggagtgGCta aagtGCtttg
 481 gatGCaggga tcccaGCagt GCaaacagac ttcggagtac ctGCGCtatg aagacacGCt
 541 tcttctgaa gaccaGCcaa caggtgagaa tgagatggtg atcatgagac ctggaaacaa
 601 atatgagtac aagttcgGCt ttgaGCttcc tcagggGCct ctgggaacat ccttcaaagg
 661 aaaatatggg tgtgtagact actgggtgaa gGCttttctt gaccGCccga GCcaGCcaac
 721 tcaagagaca aagaaaaact ttgaagtagt ggatctggtg gatgtcaata ccctgattt
 781 aatgGCacct gtgtctGCta aaaaagaaaa gaaagtttcc tGCatgttca ttcctgatgg
 841 GCgggtgtct gtctctgCtc gaattgacag aaaaggattc tgtgaaggtg atgagattc
 901 catccatGCt gactttgaga atacatgttc ccgaattgtg gtccccaaaG CtGCcattgt
 961 gGCccGCcac acttaccttG CcaatgGCca gaccaagGtG Ctgactcaga agttgtcatc
1021 agtcagagGC aatcatatta tctcagggac atGCGCatca tgGCgtgGCa agaGCcttcg
1081 ggttcagaag atcagGCctt ctatcctggG CtGCaacatc cttcgagttg aatattcctt
1141 actgatctat gttaGCgttc ctggatccaa gaaggtcatc cttgacctGC cctggtaat
1201 tgCaGCaga tcaggtctaa GCaCagaac atccaGCatg GCcaGCcgaa ccaGCtctga
1261 gatgagttgg gtagatctga acatccctga taccccagaa GCtcctcccct GCtatatgga
1321 tgtcattcct gaagatcacc gattggagaG Cccaaccact cctctGCtag atgacatgga
1381 tgGCtctcaa gacaGCccta tctttatgta tGCccctgag ttcaagttca tGCcaccacc
1441 gacttatact gaggtggatc cctGCatcct caacaacaat gtGCagtga
```

FIGURE 9

```
 314                   atgGTga tGTtcaagaa gatcaaGTct tttgagGTgG Tctttaacga
 361 ccctgaaaag GTGTacggca GTggcgagaa gGTggctggc cggGTgataG TggagGTGTG
 421 TgaaGTtact cGTGTcaaag ccGTtaggat cctggcttgc ggaGTggcta aaGTgctttg
 481 gatgcaggga tcccagcaGT gcaaacagac ttcggaGTac ctgcgctatg aagacacgct
 541 tcttctggaa gaccagccaa cagGTgagaa tgagatgGTg atcatgagac ctggaaacaa
 601 atatgaGTac aaGTtcggct ttgagcttcc tcaggggcct ctgggaacat ccttcaaagg
 661 aaaatatggG TGTGTagact actggGTgaa ggcttttctt gaccgcccga gccagccaac
 721 tcaagagaca aagaaaaact ttgaaGTaGT ggatctgGTg gatGTcaata ccctgattt
 781 aatggcacct GTGTctgcta aaaaagaaaa gaaaGTttcc tgcatGTtca ttcctgatgg
 841 gcggGTGTct GTctctgctc gaattgacag aaaaggattc tGTgaagGTg atgagattc
 901 catccatgct gactttgaga atacatGTtc ccgaattGTg GTcccccaaag ctgccattGT
 961 ggcccgccac acttaccttg ccaatggcca gaccaagGTg ctgactcaga aGTtGTcatc
1021 aGTcagaggc aatcatatta tctcagggac atgcgcatca tggcGTggca agagccttcg
1081 gGTtcagaag atcaggcctt ctatcctggg ctgcaacatc cttcgaGTtg aatattcctt
1141 actgatctat GTtagcGTtc ctggatccaa gaagGTcatc cttgacctgc ccctgGTaat
1201 tggcagcaga tcagGTctaa gcagcagaac atccagcatg gccagccgaa ccagctctga
1261 gatgaGTtgg GTagatctga acatccctga tacccccta gctcctccct gctatatgga
1321 tGTcattcct gaagatcacc gattggagag cccaaccact cctctgctag atgacatgga
1381 tggctctcaa gacagccta tcttttatGTa tgcccctgaG TtcaaGTtca tgccaccacc
1441 gacttatact gagGTggatc cctgcatcct caacaacaat GtgcaGTga
```

FIGURE 10

```
 314                 atggtga tgttcaagaa gatcaagtct tttgaggtgg tctttaACgA
 361 Ccctgaaaag gtgtACggca gtggcgagaa ggtggctggc cgggtgatag tggaggtgtg
 421 tgaagttACt cgtgtcaaag ccgttaggat cctggcttgc ggagtggcta aagtgctttg
 481 gatgcaggga tcccagcagt gcaaACagAC ttcggagtAC ctgcgctatg aagACACgct
 541 tcttctggaa gACcagccaA Caggtgagaa tgagatggtg atcatgagAC ctggaaACaa
 601 atatgagtAC aagttcggct ttgagcttcc tcagggcct  ctgggaACat cctttcaaagg
 661 aaaatatggg tgtgtagACt ACtgggtgaa ggctttttctt gACcgcccga gccagccaAC
 721 tcaagagACa aagaaaaaACt ttgaagtagt ggatctggtg gatgtcaatA Ccctgattt
 781 aatgcACct gtgtctgcta aaaaagaaaa gaaagtttcc tgcatgttca ttcctgatgg
 841 gcgggtgtct gtctctgctc gaattgACag aaaaggattc tgtgaaggtg atgagatttc
 901 catccatgct gACtttgaga atACatgttc ccgaattgtg gtccccaaag ctgccattgt
 961 ggcccgccAC ACttACcttg ccaatggcca gACcaaggtg ctgACtcaga agttgtcatc
1021 agtcagaggc aatcatatta tctcagggAC atgcgcatca tggcgtggca agagccttcg
1081 ggttcagaag atcagccctt ctatcctggg ctgcaACatc cttcgagttg aatattcctt
1141 ACtgatctat gttagcgttc ctggatccaa gaagtcatc  cttgACctgc cctggtaat
1201 tggcagcaga tcaggtctaa gcagcagaAC atccagcatg gccagccgaA Ccagctctga
1261 gatgagttgg gtagatctga ACatccctga tACcccagaa gctcctccct gctatatgga
1321 tgtcattcct gaagatcACc gattggagag cccaACCACt cctctgctag atgACatgga
1381 tggctctcaa gACagcccta tctttatgta tgcccctgag ttcaagttca tgccACcACc
1441 gACttatACt gaggtggatc cctgcatcct caACaACaat gtgcagtga
```

FIGURE 11

```
 314          atggtga tgTTcaagaa gaTcaagTcT TTtgaggtgg TcTTTaacga
 361 ccctgaaaag gtgTacggca gtggcgagaa ggtggctggc cgggtgaTag tggaggtgtg
 421 tgaagTTacT cgtgTcaaag ccgTTaggaT cctggcTTgc ggagtggcTa aagtgcTTtg
 481 gatgcaggga Tcccagcagt gcaaacagac TTcggagTac ctgcgcTatg aagacacgcT
 541 TcTTctggaa gaccagccaa caggtgagaa tgagatggtg aTcatgagac ctggaaacaa
 601 aTatgagTac aagTTcggcT TtgagcTTcc Tcaggggcct ctggaacaT ccTTcaaagg
 661 aaaaTatggg tgtgTagacT actgggtgaa ggcTTTTcTt gaccgcccga gccagccaac
 721 Tcaagagaca aagaaaaaacT TtgaagTagt ggaTctggtg gatgTcaaTa ccccctgaTTT
 781 aatgcaccct gtgTctgcTa aaaaagaaaa gaaagTTTcc tgcatgTTca TTcctgatgg
 841 gcgggtgTct gTcTctgcTc gaaTtgacag aaaaggaTTc tgtgaaggtg atgagaTTTc
 901 caTccatgct gacTTtgaga aTacatgTTc ccgaaTtgtg gTccccaaag ctgccaTTgt
 961 ggcccgccac acTTaccTtg ccaatggcca gaccaaggtg ctgacTcaga agTtgTcaTc
1021 agTcagaggc aaTcaTaTTa TcTcagggac atgcgcaTca tggcgtggca agagccTTcg
1081 ggTTcagaag aTcaggccTT cTaTcctggg ctgcaacaTc cTTcgagTtg aaTaTTccTT
1141 actgaTcTat gTTagcgTTc ctggaTccaa gaaggTcaTc cTtgacctgc ccctggTaaT
1201 tggcagcaga TcaggTcTaa gcagcagaac aTccagcatg gccagccgaa ccagcTctga
1261 gatgagTtgg gTagaTctga acaTccctga Taccccagaa gcTccTcoct gcTaTatgga
1321 tgTcaTTcct gaagaTcacc gaTtggagag cccaaccacT ccTctgcTag atgacatgga
1381 tggcTcTcaa gacagcccTa TcTTTatgTa tgccccctgag TTcaagTTca tgccaccacc
1441 gacTTaTact gaggtggaTc cctgcaTccT caacaacaat gtgcagtga
```

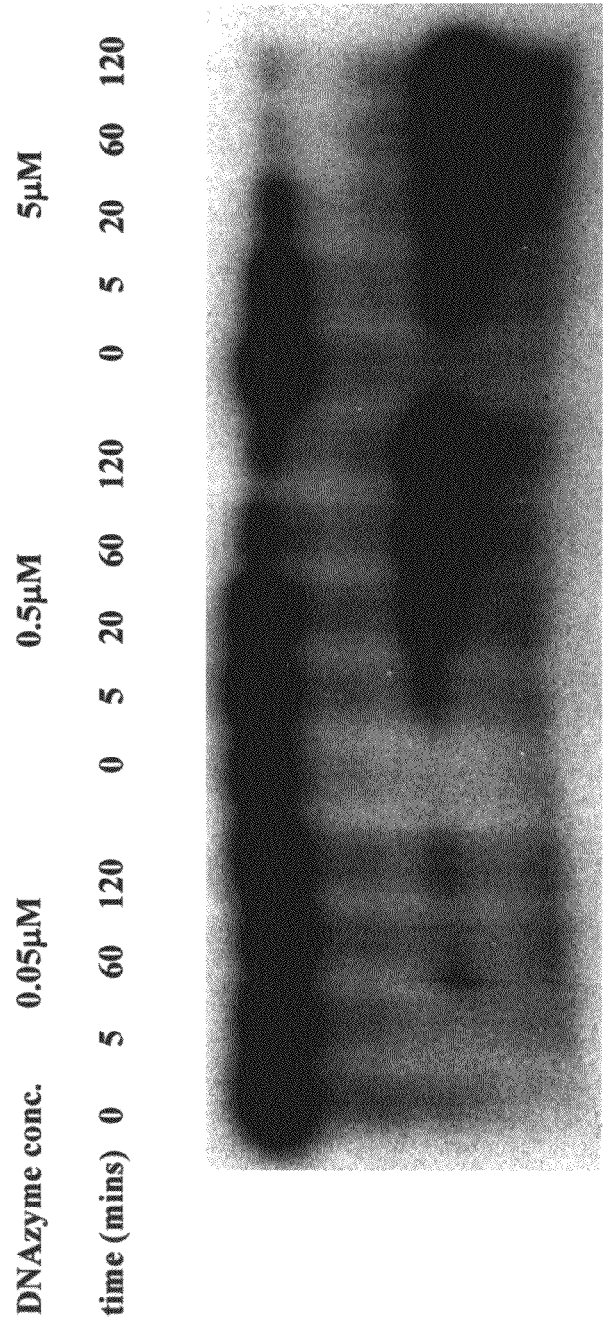

Early Proliferation/ Regeneration Of Immature Cardiomyocyte Lineage Progenitors Accompanying Neovascularization (confocal microscopy: red nucleus, yellow Ki67, blue cytoplasm alpha-sarcomeric actin)

Later Differentiation And Regeneration Of Mature Cardiomyocytes Accompanying Neovascularization
(immunohistochemistry: blue nucleus rat Ki67, brown cytoplasm troponin I)

Confocal microscopy showing nuclear cycling (blue nucleus, green rat Ki67) of troponin I-positive mature cardiomyocyte (red cytoplasm)

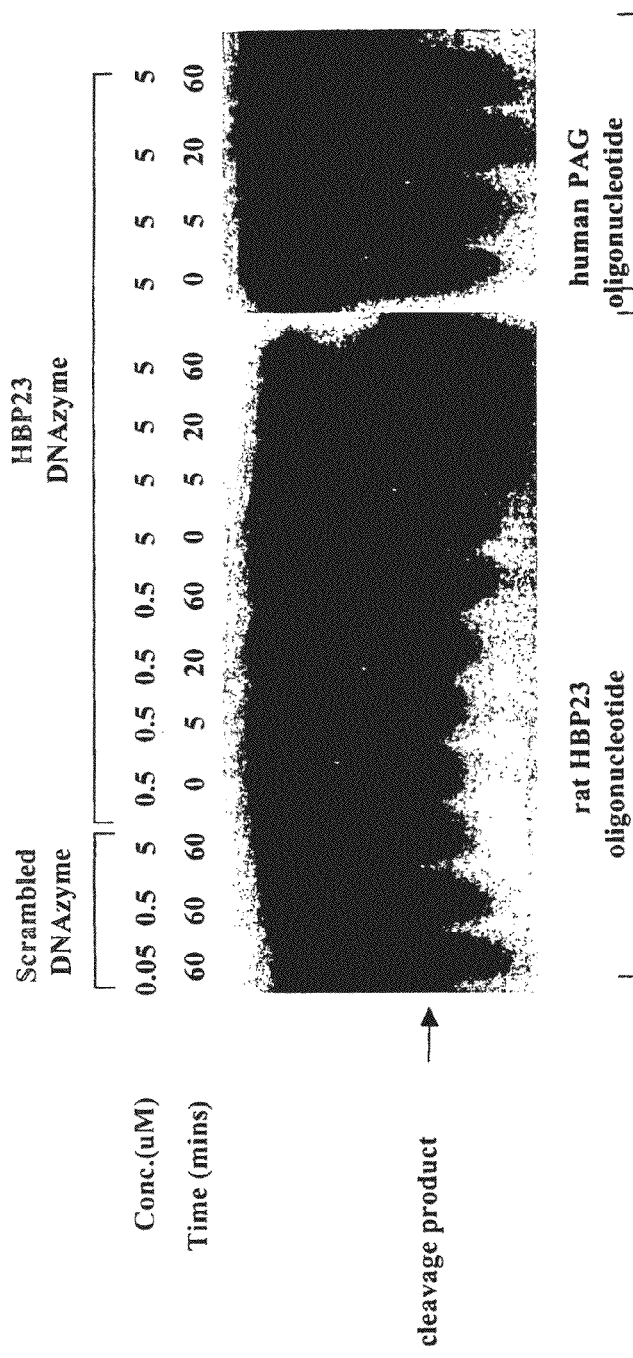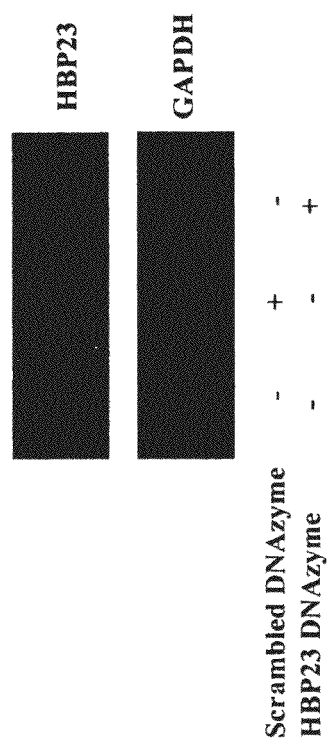
Figure 24A
Figure 24B

Pattern of CXCR4 Expression Following Acute Myocardial Ischemia Is Focal And Peri-Infarct Figure 29
Effect of SDF (100 nM) on pAKT/AKT and pERK/ERK Expression in Rat Neonatal Cardiac Myocytes
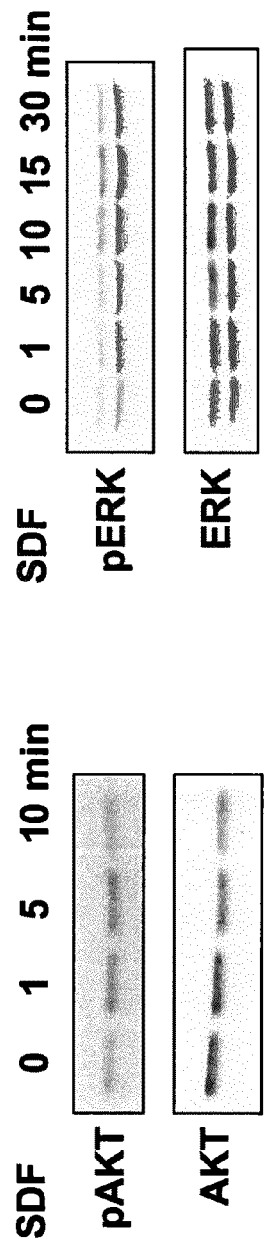
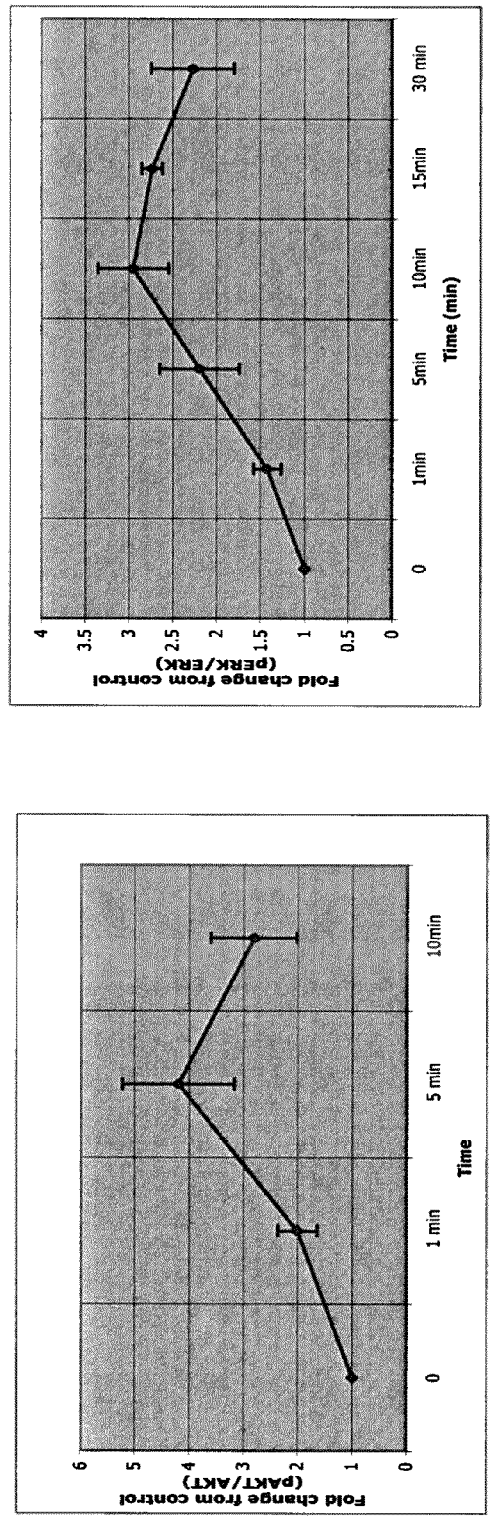

US 8,663,652 B2

REGENERATION OF ENDOGENOUS MYOCARDIAL TISSUE

This application is a continuation-in-part and claims priority of PCT International Application PCT/US03/12768, filed Apr. 23, 2003, which is a continuation-in-part and claims priority of U.S. Ser. No. 10/128,738, filed Apr. 23, 2002 now abandoned.

Throughout this application, various publications are referenced in parentheses by arabic numbers. Full citations for these references may be found at the end of the specification immediately preceding the claims. The disclosures of these publications in their entireties are hereby incorporated by reference into this application to more fully describe the state of the art to which this invention pertains.

BACKGROUND

Healing of a myocardial infarct is complicated by the need for viable myocytes at the peri-infarct rim to undergo compensatory hypertrophy in order to increase pump function in response to the loss of infarcted tissue (1,2). This initiates a process termed cardiac remodelling which is characterized by apoptotic loss of hypertrophied myocytes, expansion of the initial infarct area, progressive collagen replacement, and heart failure (3-6). We have recently put forward the hypothesis that hypertrophied cardiac myocytes undergo apoptosis because the endogenous capillary network cannot provide the compensatory increase in perfusion required for cell survival (7).

Vascular network formation is the end result of a complex process that begins in the pre-natal period with induction of vasculogenesis by hemangioblasts—cells derived from the human ventral aorta which give rise to both endothelial and hematopoietic elements (8-11). Cells which can differentiate into endothelial elements also exist in adult bone marrow (12-14) and can induce vasculogenesis in ischemic tissues (15-17). In the adult, new blood vessel formation can occur either through angiogenesis from pre-existing mature endothelium or vasculogenesis mediated by bone marrow-derived endothelial precursors. Recently, we identified a specific population of endothelial progenitor cells (angioblasts) derived from human adult bone marrow which has phenotypic and functional characteristics of embryonic angioblasts (7). We showed that intravenous administration of these cells resulted in selective homing to ischemic myocardium, induction of infarct bed vasculogenesis, prevention of peri-infarct myocyte apoptosis, and significant improvement in myocardial function (7).

We recently discovered that CXC chemokines containing the ELR motif regulate migration of human bone marrow-derived endothelial progenitor cells to sites of tissue ischemia. Moreover, since selective bone marrow homing and engraftment of hematopoietic progenitors depends on CXCR4 binding to SDF-1 expressed constitutively in the bone marrow (28-30), we demonstrated that interruption of CXCR4/SDF-1 interactions could redirect trafficking of human bone marrow-derived endothelial progenitor cells to sites of tissue ischemia, thereby augmenting therapeutic vasculogenesis. Our results indicated that CXC chemokines, including IL-8, Gro-alpha, and SDF-1, play a central role in regulating human adult bone marrow-dependent vasculogenesis.

Recent observations have suggested that a second compensatory response of viable cardiomyocytes is to proliferate and regenerate following injury (18,19). We have previously shown that pro-angiogenic factors, such as endothelial progenitor cells at a minimum concentration can induce vasculogenesis. Here we disclose the result that careful dosing of pro-angiogenic agents, or agents that can activate AKT or ERK, or activate CXCR4 on cells can induce cardiomyocyte proliferation or prevent loss of cardiomyoctyes also.

SUMMARY

This invention provides a method of treating a disorder of a subject's heart involving loss of cardiomyocytes which comprises administering to the subject a composition comprising an amount of a human stromal derived factor-1 and an amount of a human granulocyte-colony stimulating factor, the composition being administered in an amount effective to cause proliferation of cardiomyocytes within the subject's heart so as to thereby treat the disorder.

This invention also provides a method of treating a subject suffering from a disorder of a tissue involving loss and/or apoptosis of cells of the tissue which comprises administering to the subject a composition comprising an amount of an agent which induces phosphorylation and/or activation of protein kinase B, the composition being administered in an amount effective to cause proliferation of the cells and/or inhibit apoptosis of the cells of the tissue within the subject so as to thereby treat the disorder.

This invention also provides a method of treating a subject suffering from a disorder of a tissue involving loss and/or apoptosis of cells of the tissue which comprises administering to the subject a composition comprising an amount of an agent which induces phosphorylation and/or activation of an extracellular signal-regulated protein kinase, the composition being administered in an amount effective to inhibit apoptosis and/or cause proliferation of the cells of the tissue within the subject so as to thereby treat the disorder.

This invention also provides a method of treating a subject suffering from a disorder of a tissue involving loss and/or apoptosis of cells of the tissue which comprises administering to the subject a composition comprising an amount of an agent which induces activation of CXCR4, the composition being administered in an amount effective to cause proliferation of the cells and/or inhibit apoptosis of the cells of the tissue within the subject so as to thereby treat the disorder.

BRIEF DESCRIPTION OF THE FIGURES

FIGS. 1A-1D: IL-8/Gro-Alpha CXC Chemokines Regulate Migration Of Human Endothelial progenitor cells (angioblasts) To Myocardial Tissue In Vivo And Subsequent Development Of Vasculogenesis.

(A) DiI-labelled human endothelial progenitor cells (angioblasts)(>98% CD34+ purity) injected intravenously into nude rats infiltrate rat myocardium after coronary artery ligation and infarction but not after sham operation at 48 hours.

(B) Migration of human endothelial progenitor cells (angioblasts) to ischemic rat myocardium is inhibited by mAbs against either rat IL-8 or the IL-8/Gro-alpha chemokine family receptors CXCR1 and CXCR2 (all p<0.01), but not against VEGF or its receptor Flk-1 (results are expressed as mean+sem of three separate experiments).

(C) Masson's trichrome stain of rat myocardial infarct bed at two weeks after LAD ligation demonstrating diffuse increase in matrix deposition and few capillaries in representative animal injected with saline (×400), diffuse increase in capillaries (arrowheads) and reduction in matrix deposition in representative animal injected with human bone marrow-derived endothelial progenitor cells (×400), and reduction in capillary numbers in representative animal injected with human endothelial progenitor cells (angioblasts) together with mAb against human CXCR1/2 (×400).

(D) Intracardiac injection of IL-8 or SDF-1 at 1 µg/ml significantly increases in vivo chemotaxis of DiI-labelled human endothelial progenitor cells (angioblasts) (98% CD34+ purity) into non-ischemic rat heart in comparison with injection of saline or stem cell factor (SCF), $p<0.01$ (results are expressed as mean+sem of three separate experiments). Below is shown representative fluorescence microscopy of intravenously-injected DiI-labelled human endothelial progenitor cells infiltrating non-ischemic rat heart after intracardiac injection with saline, IL-8 or SDF-1.

Figure 2B:
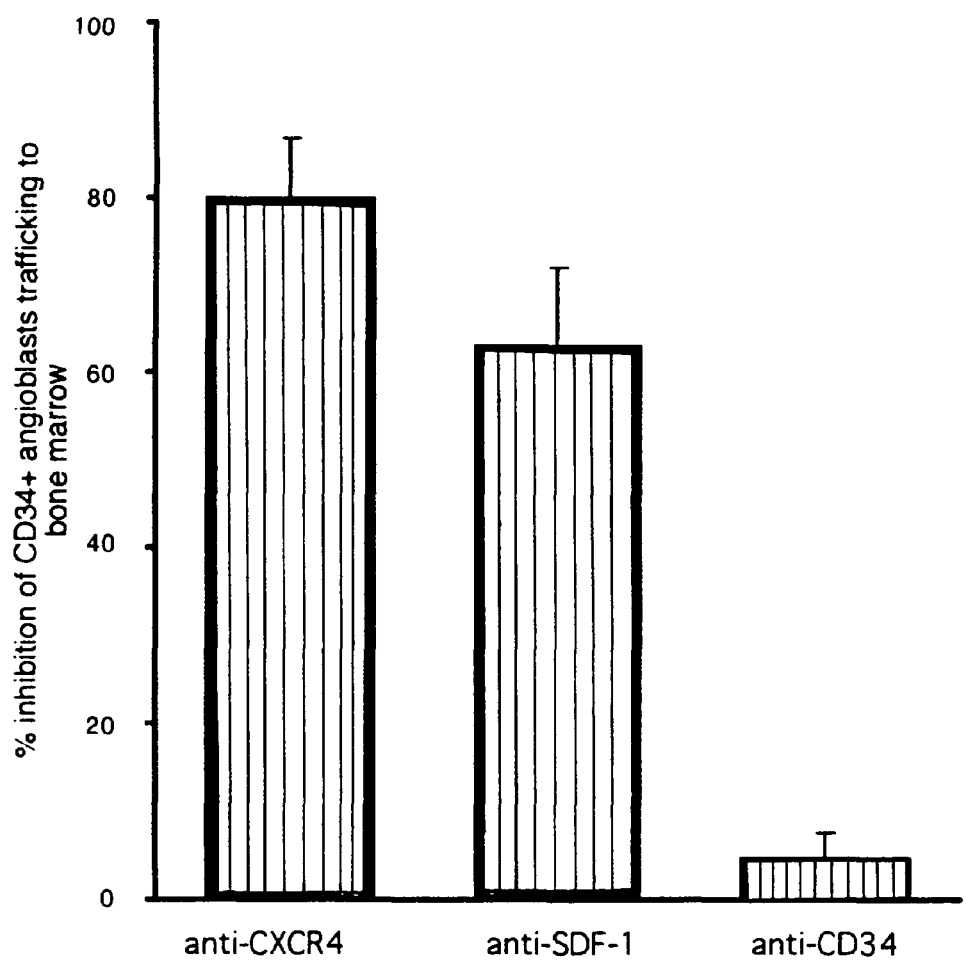
Figure 2C:
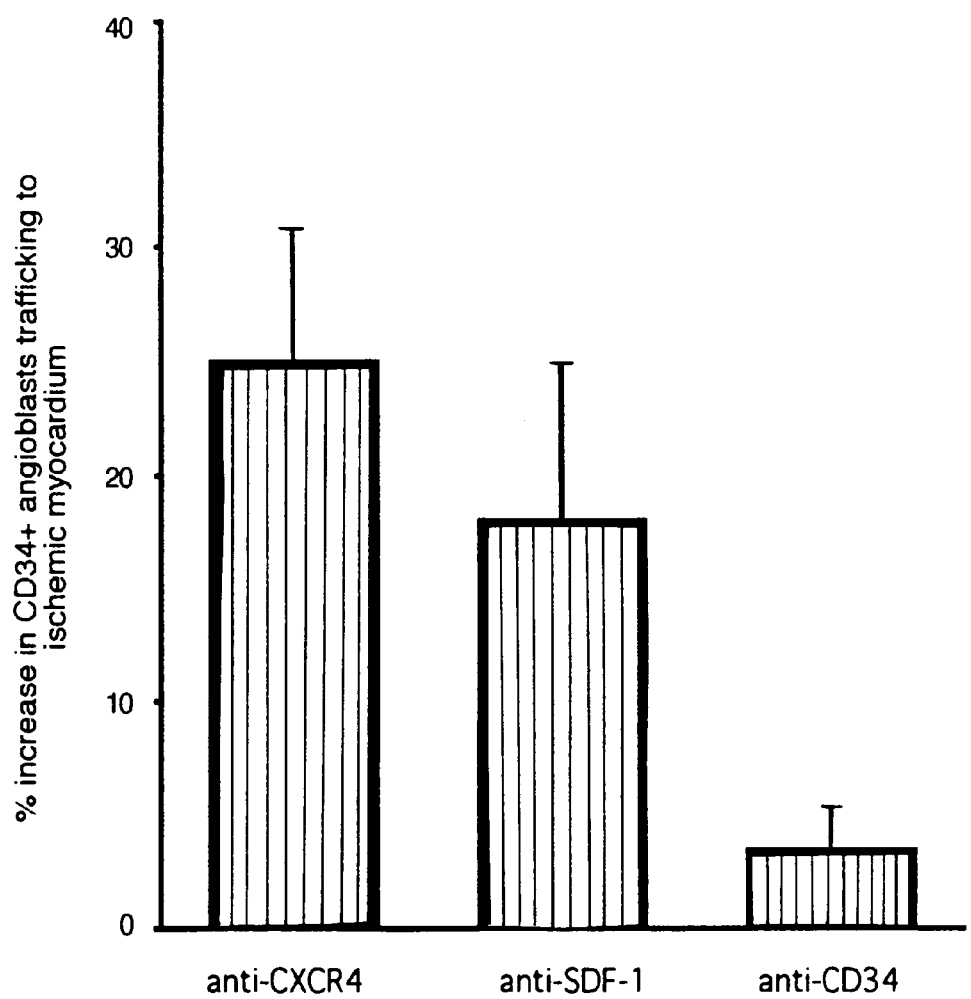
Figure 3A:
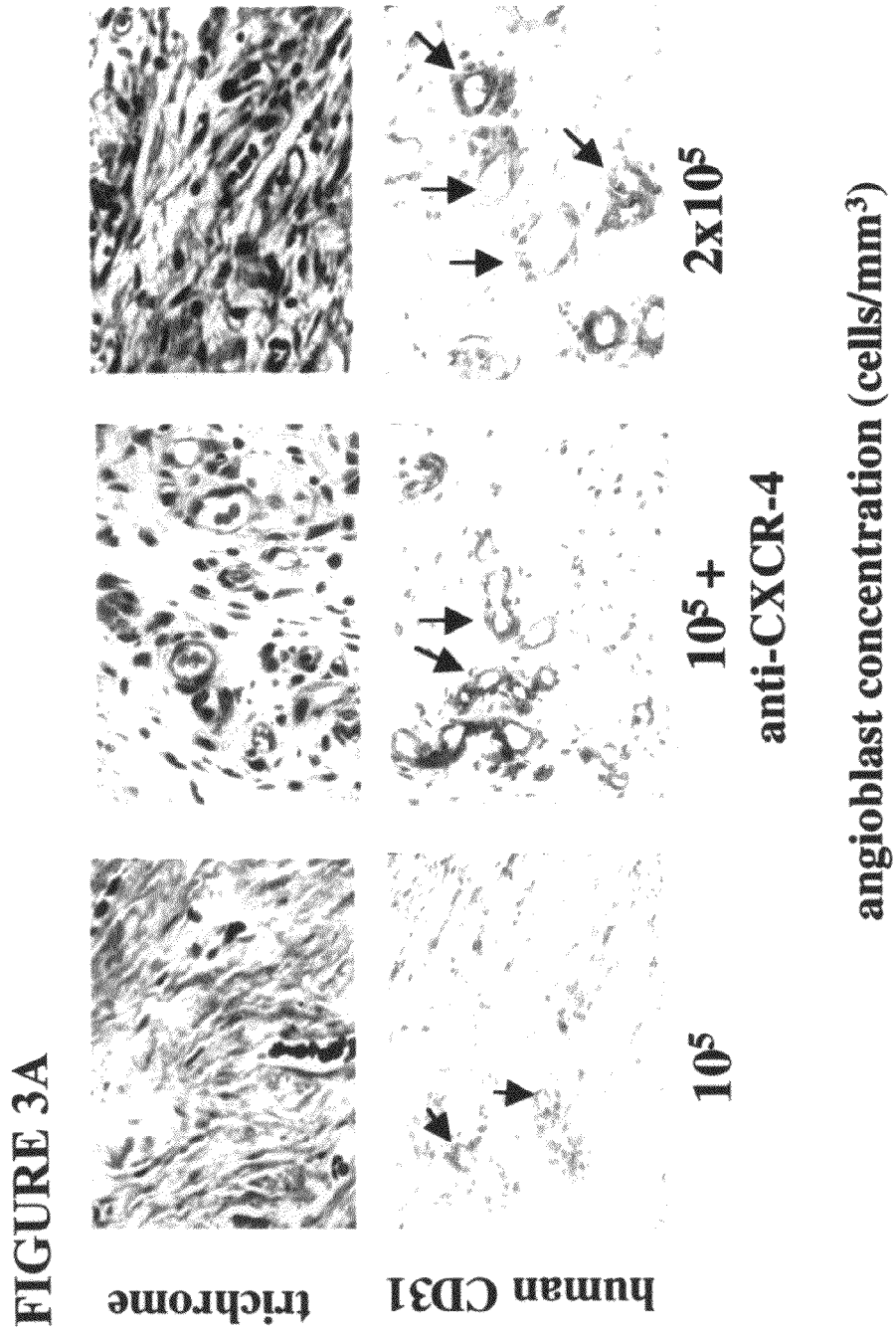
Figure 3B:
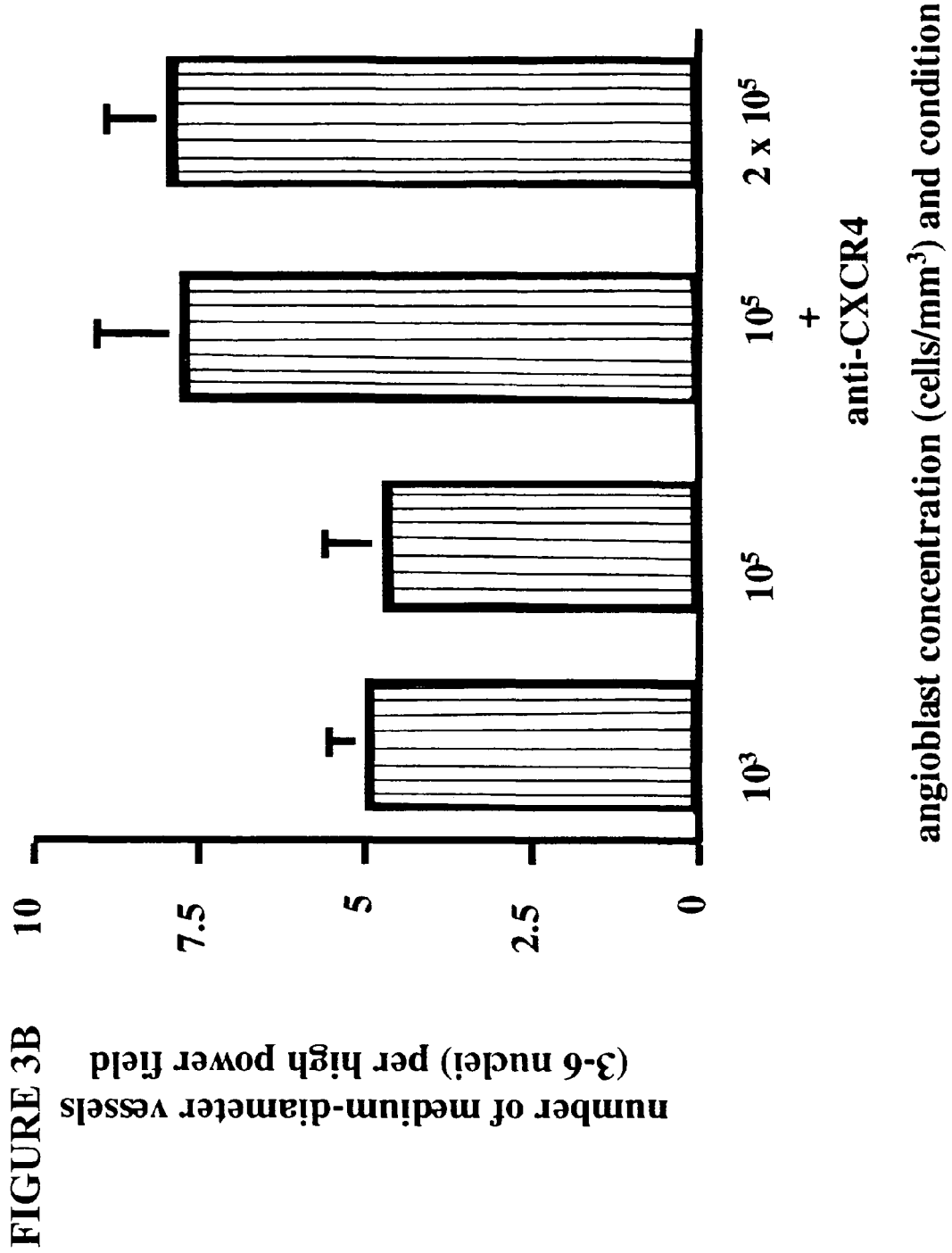
Figure 3C:
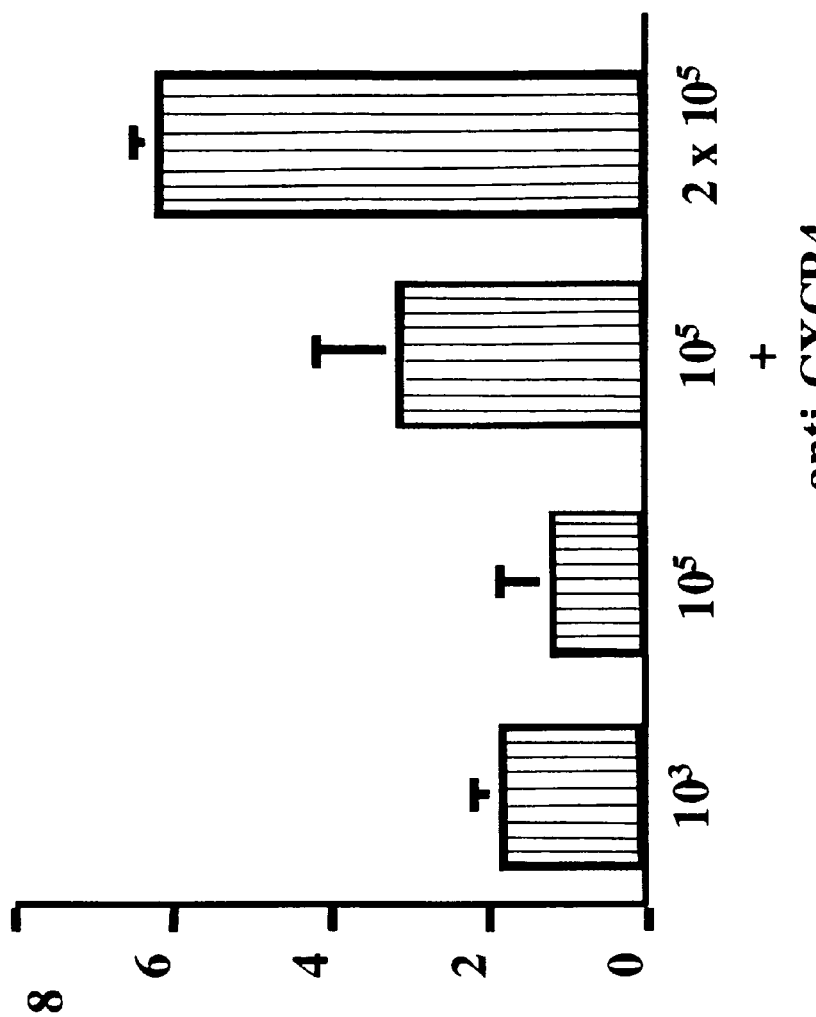
Figure 3D:
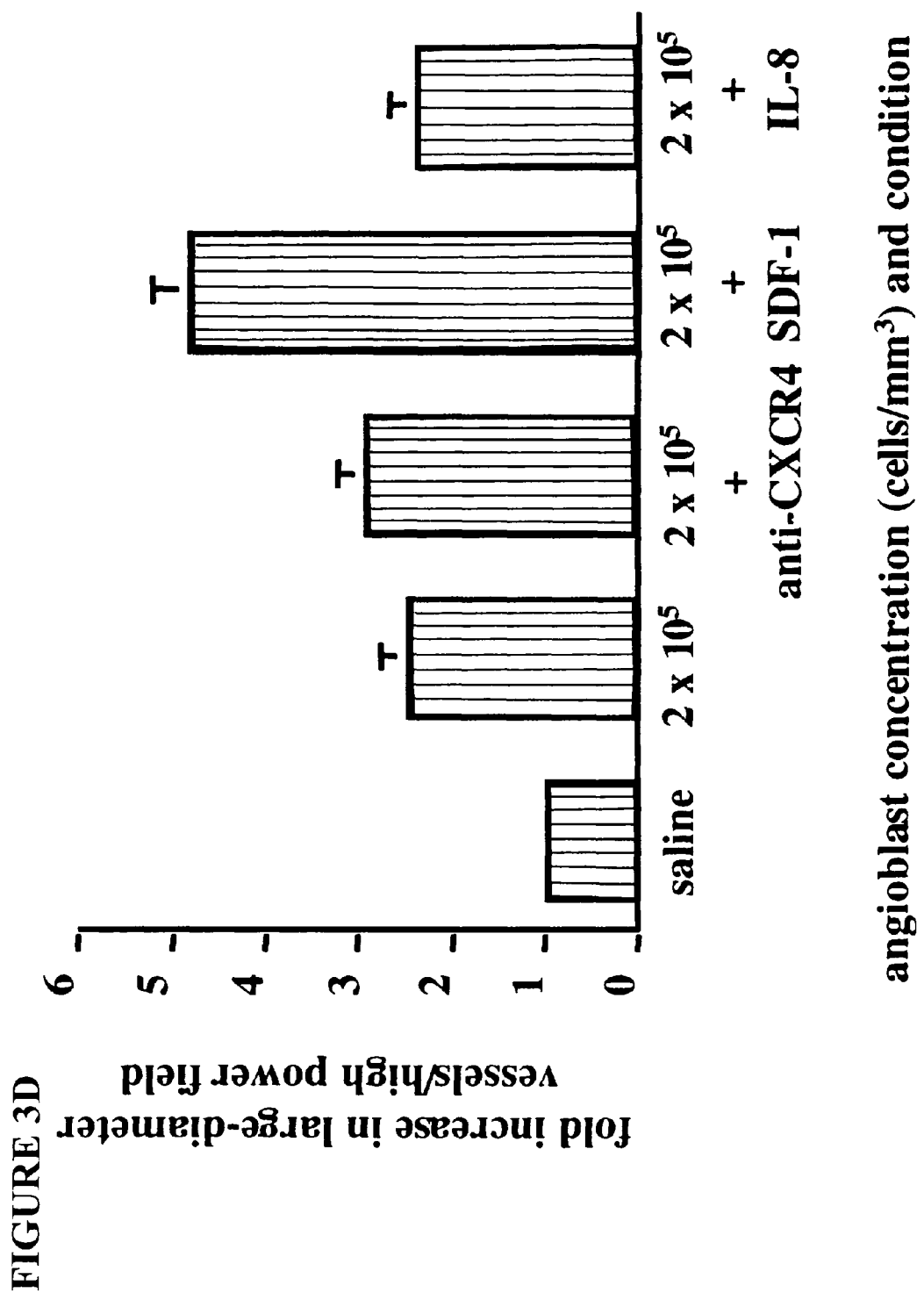
Figure 3E:
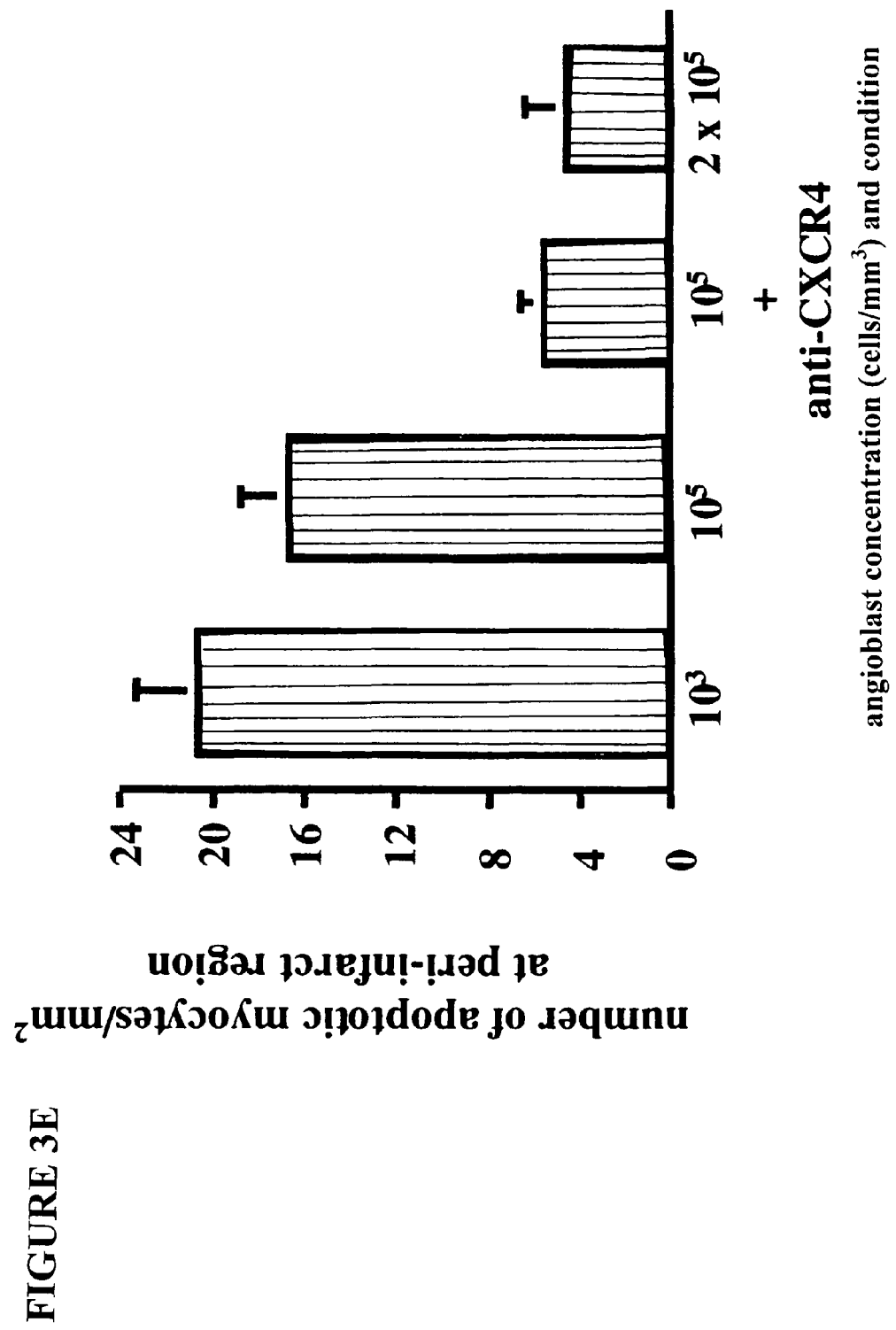
Figure 3F:
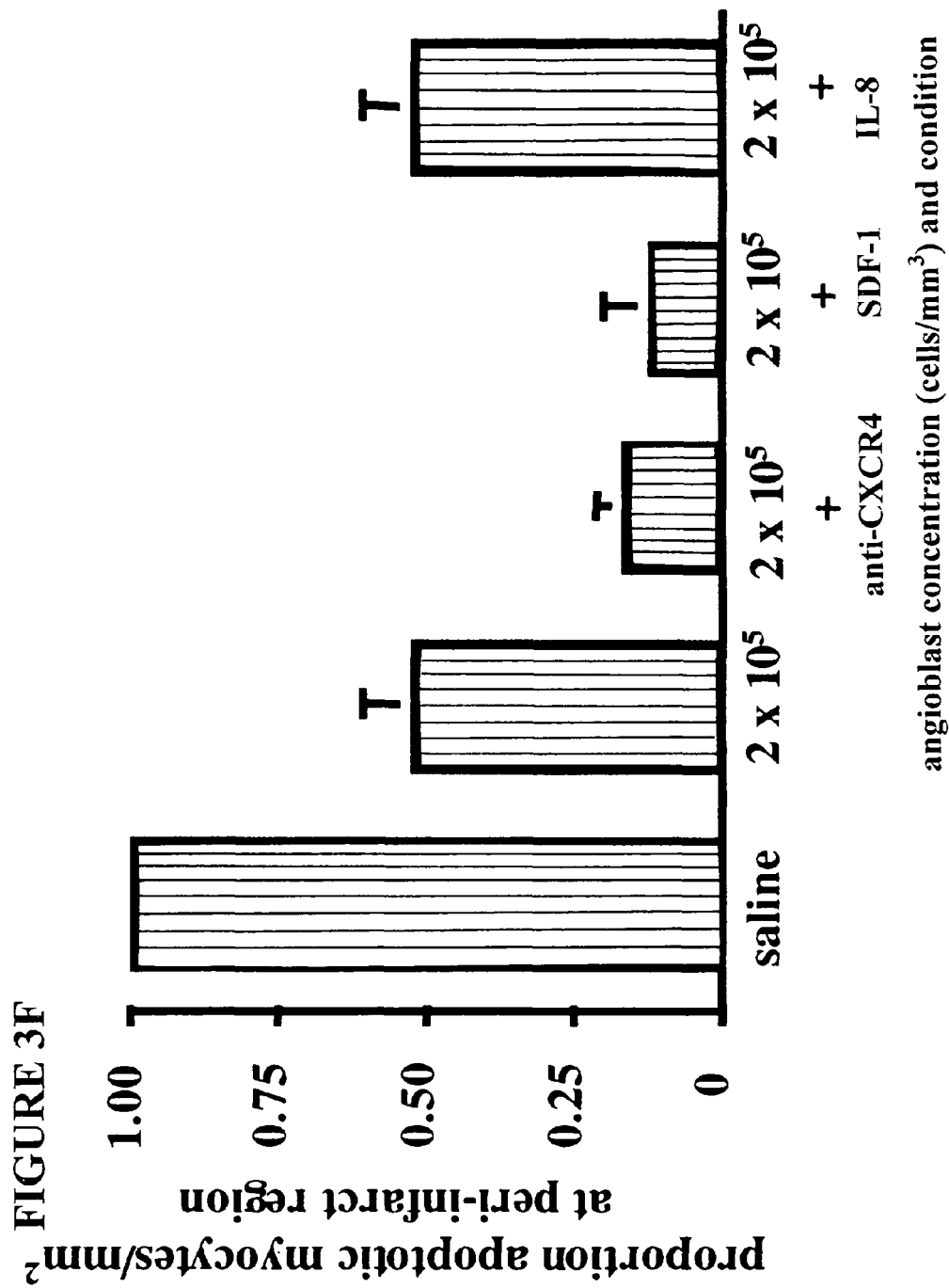

FIGS. 2A-2C: Blocking CXCR4/SDF-1 Interactions Redirects Intravenously Injected Human Endothelial progenitor cells From Bone Marrow To Ischemic Myocardium.

(A) the proportion of human CD34+CD117$^{bright}$ endothelial progenitor cells (angioblasts) in rat bone marrow 2-14 days after intravenous injection is significantly increased following ischemia induced by LAD ligation (results are expressed as mean+sem of bone marrow studies in three animals at each time point).

(B) and (C) depict the effects of mAbs against CXCR4, SDF-1 or CD34 on trafficking of human CD34+ endothelial progenitor cells (angioblasts) to rat bone marrow and myocardium following LAD ligation. Co-administration of anti-CXCR4 or anti-SDF-1 significantly reduced trafficking of intravenously injected human CD34+ cells to rat bone marrow at 48 hours and increased trafficking to ischemic myocardium, whereas anti-CD34 mAb had no effect (results are expressed as mean+sem of bone marrow and cardiac studies performed in three LAD-ligated animals at 48 hours after injection).

FIGS. 3A-3F. Redirected Trafficking Of Human Endothelial Progenitor Cells (angioblasts) To The Site Of Infarction Induces Vasculogenesis And Protects Cardiomyocytes Against Apoptosis.

(A) Myocardial infarct bed two weeks post-LAD ligation from representative animals in each group stained with Masson's trichrome (upper panel) or immunoperoxidase after binding of anti-CD31 mAb (lower panel). The infarct zones of rats receiving either $10^3$ or $10^5$ endothelial progenitor cells (angioblasts) show myocardial scars composed of paucicellular, dense fibrous tissue stained blue by trichrome (×400). In contrast, the infarct zones of rats injected with $10^5$ endothelial progenitor cells plus anti-CXCR4 mAb show significant increase in cellularity of granulation tissue, minimal matrix deposition and fibrosis, and numerous medium-sized capillaries of human origin. The infarct zones of rats injected with $2\times10^5$ endothelial progenitor cells show a similar reduction in fibrous tissue and increase in medium-sized capillaries, and an additional increase in large-sized vessels of human origin.

(B) and (C) show the relationship between the number of human CD117$^{bright}$ endothelial progenitor cells injected intravenously ($10^3$, $10^5$, $10^5$ plus anti-CXCR4 mAb, and $2\times10^5$) and development of rat infarct bed vasculogenesis at two weeks, defined as the mean number of capillaries/high power field (hpf) with medium- or large-sized lumen diameter (respectively, 0.02 mm mean diameter with 3-6 contiguous endothelial lining cells and 0.05 mm mean diameter with >6 contiguous endothelial lining cells). Results are expressed as the mean+sem of at least 15 hpf in three separate experiments.

(B) the groups receiving either $2\times10^5$ endothelial progenitor cells (angioblasts) or $10^5$ endothelial progenitor cells plus anti-CXCR4 mAb demonstrated 1.7-fold higher numbers of medium-sized capillaries compared with the other two groups ($p<0.01$).

(C) the group receiving $2\times10^5$ endothelial progenitor cells (angioblasts) additionally demonstrated 3.3-fold higher numbers of large-lumen capillaries compared with the groups receiving $10^3$ or $10^5$ endothelial progenitor cells ($p<0.01$), and 2-fold higher numbers of large-lumen capillaries compared with the group receiving $10^5$ endothelial progenitor cells plus anti-CXCR4 mAb ($p<0.01$).

(D) shows that co-administration of anti-CXCR4 mAb together with the highest concentration of endothelial progenitor cells (angioblasts), $2\times10^5$, resulted in a further 23% increase in growth of large-lumen capillaries. More strikingly, there was a further 2-fold increase in capillary numbers when $2\times10^5$ endothelial progenitor cells were injected intravenously after direct intracardiac delivery of 1.0 µg/ml SDF-1 into infarcted hearts ($p<0.01$) (results are expressed as mean+sem of three separate experiments).

(E) shows that at 2 weeks the numbers of apoptotic myocytes at the peri-infarct rim, defined by concomitant staining with anti-desmin mAb and DNA end-labeling using TUNEL technique, are significantly reduced in rats receiving either $2.0\times10^5$ endothelial progenitor cells or $10^5$ endothelial progenitor cells together with anti-CXCR4 mAb in comparison to rats receiving $10^3$ or $10^5$ endothelial progenitor cells ($p<0.01$) (results are expressed as mean+sem of three separate experiments).

(F) shows that co-administration of anti-CXCR4 mAb or intracardiac injection of SDF-1 resulted in further reductions in cardiomyocyte apoptosis of 65% and 76%, respectively, at two weeks (both $p<0.001$) (results are expressed as mean+sem of three separate experiments).

FIGS. 4A-4H. Infarct Bed Vasculogenesis Improves Long-Term Myocardial Function Through Mechanisms Involving Both Cardiomyocyte Protection and Proliferation/Regeneration.

(A) and (B) show the relationship between the number of human CD117$^{bright}$ endothelial progenitor cells (angioblasts) injected intravenously ($10^3$, $10^5$, $10^5$ plus anti-CXCR4 mAb, and $2\times10^5$) and improvement in myocardial function at 15 weeks, defined as mean improvement in left ventricular ejection fraction (LVEF) (A) and mean reduction in left ventricular area at end-systole (LVAs) (B). No significant improvement in these parameters was observed in the groups receiving $10^3$ or $10^5$ endothelial progenitor cells in comparison to rats receiving saline alone. In contrast, rats receiving $10^5$ endothelial progenitor cells plus anti-CXCR4 mAb demonstrated significant recovery in LVEF and reduction in LVAs (both $p<0.001$). The group receiving $2\times10^5$ endothelial progenitor cells demonstrated still 50% greater recovery in LVEF and reduction in LVAs (both $p<0.001$).

(C) Section from infarct of representative animal receiving $2\times10^5$ endothelial progenitor cells (angioblasts) showing a high frequency of cardiomyocytes staining positively for both cardiac-specific troponin I and rat-specific Ki-67 (arrows). Note the proximity of Ki-67-positive cardiomyocytes to capillaries (arrowheads).

(D) Section from infarct of representative animal receiving $2\times10^5$ endothelial progenitor cells showing "finger" of cardiomyocytes of rat origin, as determined by expression of rat MHC class I molecules, extending from the peri-infarct region into the infarct zone. These cellular islands contain a high frequency of myocytes staining positively for both cardiac-specific troponin I and rat-specific Ki-67 (arrows). Sections from infarcts of representative animals receiving saline do not show same frequency of dual staining myocytes. Bar graph shows that the group of animals receiving $2\times10^5$ human endothelial progenitor cells has a significantly higher index of cell cycling cardiomyocytes at the peri-infarct region than saline controls or sham operated animals (both p<0.01). No difference between the groups is seen at sites distal to the infarct.

(E) shows that the index of cell-cycling cardiomyocytes at the peri-infarct rim was increased by a further 1.9-fold when $2 \times 10^5$ human endothelial progenitor cells were intravenously co-administered together with SDF-1 injected directly into the ischemic myocardium alone (p<0.01), or an 8-fold cumulative increase in cell-cycling cardiomyocytes at two weeks compared with LAD-ligated controls receiving saline (results are expressed as mean+sem of three separate experiments).

(F) shows that intravenous co-administration of anti-CXCR4 mAb, or intracardiac co-administration of SDF-1, but not IL-8, results in 2.8 to 4-fold greater LVEF improvement, determined by echocardiography, compared with intravenous injection of $2 \times 10^5$ endothelial progenitor cells alone (p<0.01) (results are expressed as mean+sem of three separate experiments).

(G) shows that at 15 weeks the mean proportion of scar/normal left ventricular myocardium in rats receiving either or $10^5$ endothelial progenitor cells together with anti-CXCR4 mAb was significantly reduced in comparison to rats receiving either $10^3$ or $10^5$ endothelial progenitor cells (angioblasts) alone, or saline (p<0.01). The group receiving $2.0 \times 10^5$ endothelial progenitor cells demonstrated still 38% greater reduction in the ratio of scar/muscle tissue (results are expressed as mean+sem of three separate experiments).

(H) Sections of rat hearts stained with Masson's trichrome at 15 weeks after LAD ligation and injection of $2.0 \times 10^6$ G-CSF mobilized human cells containing $10^3$ (left) or $2.0 \times 10^5$ (right) CD117$^{bright}$ endothelial progenitor cells. Hearts of rats receiving $10^3$ endothelial progenitor cells had greater loss of anterior wall mass, collagen deposition (lighter gray), and septal hypertrophy compared with hearts of rats receiving $2.0 \times 10^5$ endothelial progenitor cells.

FIG. 5: This figure shows mRNA expression of three genes in the ischemic rat hearts at various time points. You will see that at 48 hours and 2 weeks after LAD ligation and ischemia, HBP23 (the rat homologue of human PAG/NKEF-A,B,C, all of which are part of the family of peroxiredoxins (Prx)) is decreased, and vitamin D3 upregulated protein VDUP-1 is increased. The early (48 hour) reduction in PRX and increase in VDUP-1 results in a compensatory increase in thiol reductase thioredoxin (TRX). Note that endothelial progenitor cell therapy reverses this pattern of mRNA expression.

FIG. 6: DNA sequence (SEQ ID NO:1) corresponding to mRNA encoding VDUP-1.

FIG. 7: This figure shows catalytic DNA 5'-AT-3' cleavage sites on VDUP-1 DNA (SEQ ID NO:3) corresponding to the coding region of VDUP-1 mRNA. Cleavage site pairs are uppercase.

FIG. 8: This figure shows catalytic DNA 5'-GC-3' cleavage sites on VDUP-1 DNA (SEQ ID NO:3) corresponding to the VDUP-1 mRNA. Cleavage site pairs are uppercase.

FIG. 9: This figure shows catalytic DNA 5'-GT-3' cleavage sites on VDUP-1 DNA (SEQ ID NO:3) corresponding to the VDUP-1 mRNA. Cleavage site pairs are uppercase.

FIG. 10: This figure shows catalytic DNA 5'-AC-3' cleavage sites on VDUP-1 DNA (SEQ ID NO:3) corresponding to the VDUP-1 mRNA. Cleavage site pairs are uppercase.

FIG. 11: This figure shows sites which can be cleaved by a hammerhead ribozyme in VDUP-1 DNA (SEQ ID NO:3) corresponding to the VDUP-1 mRNA coding region. Uppercase "T" represents cleavage site.

FIG. 12: This figure shows that at VDUP-1 enzyme concentrations ranging from 0.05 μM to 5 μM the sequence-specific VDUP1 DNA enzyme cleaved a synthetic rat VDUP1 oligonucleotide in a concentration- and time-dependent manner.

FIG. 13: (a) Shows intramyocardial injection of the rat sequence-specific VDUP1 DNA enzyme at 48 hours after LAD ligation resulted in a 75% mean inhibition of proliferating cardiac fibroblasts in the infarct zone two weeks later in comparison to injection of scrambled DNA enzyme control (p<0.01). (b) Shows injection of VDUP1 DNA enzyme resulted in 20% mean reduction in apoptotic cardiomyocytes at the peri-infarct region relative to injection with the scrambled. DNA enzyme control (p<0.05).

FIG. 14: (a) Shows inhibition of fibroblast proliferation and cardiomyocyte apoptosis resulted in significant reduction of mature scar deposition in the infarct zone, from a mean of 35% for animals receiving control scrambled DNA enzyme to a mean of 20% for those receiving VDUP1 DNA enzyme (p<0.01). (b) Shows animals receiving VDUP1 DNA enzyme demonstrated a 50% mean recovery in cardiac function, as determined by ejection fraction, whereas no improvement was seen in animals receiving scrambled control DNA enzyme (p<0.01)

Figure 15B:
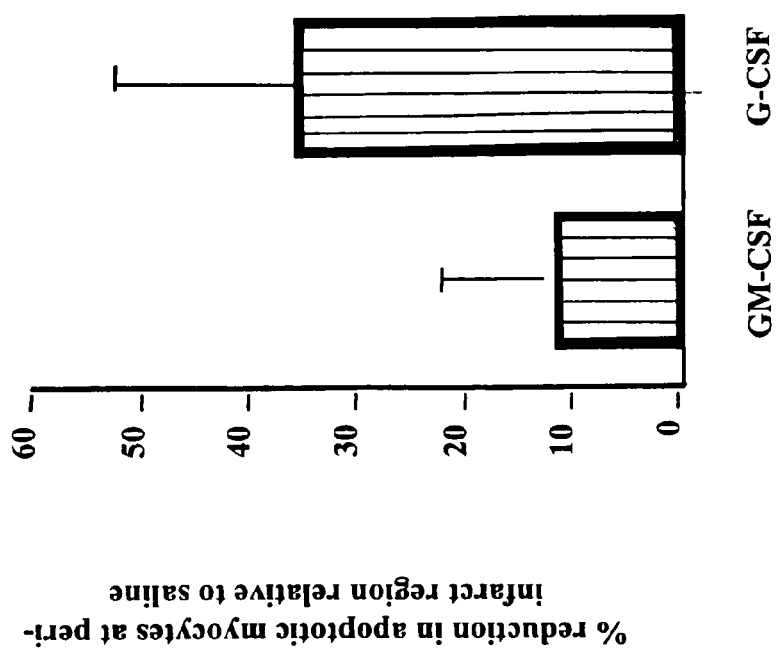

FIG. 15: (a) Shows that G-CSF, when used systematically at the same dosages after myocardial infarction, is a more potent inducer of cardiac neovascularization than GM-CSF. (B) Shows G-CSF is a more potent inhibitor of cardiomyocyte apoptosis than GM-CSF.

FIG. 16: (a) Shows G-CSF is a more potent inducer of cardiomyocyte regeneration than GM-CSF, and (b) shows that G-CSF enables significantly greater recovery of cardiac function after acute myocardial infarction.

FIG. 17: (a) Shows intravenous administration of anti-CXCR4 monoclonal antibody after acute myocardial infarction induces significantly greater numbers of blood vessels at the peri-infarct region. (b) Shows the greater recovery of cardiac/myocardial function than with control antibodies.

Figure 18:
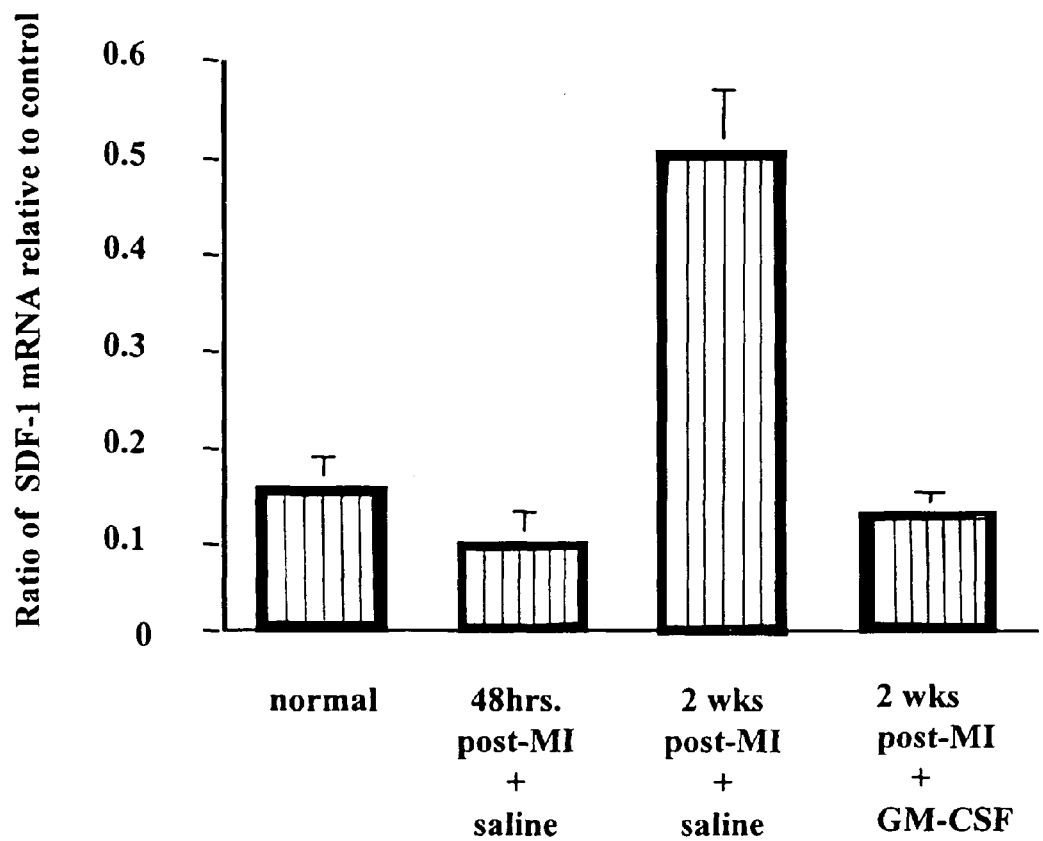

FIG. 18: Shows myocardial expression of SDF-1 mRNA increased by two weeks, but not within the first 48 hours after myocardial infarction, and is inhibited by subcutaneously injecting GM-CSF.

Figure 19B:
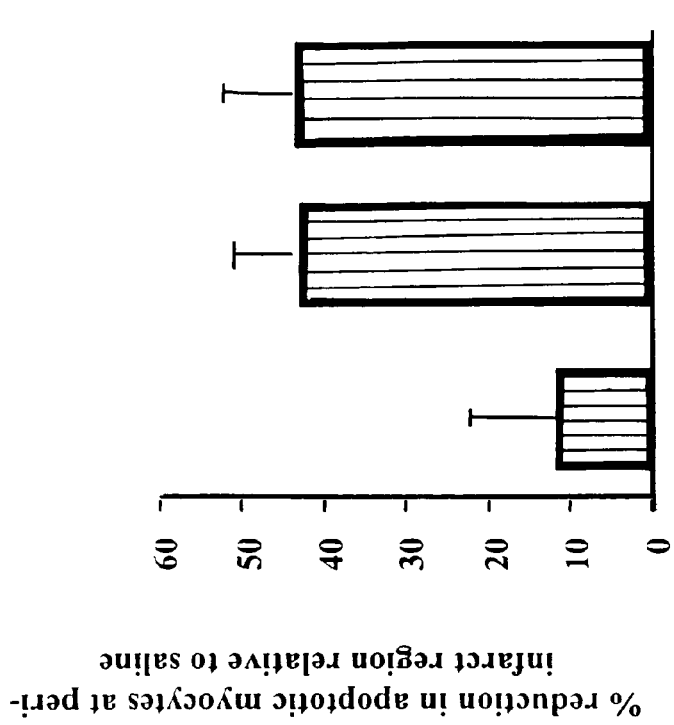
Figure 19A:
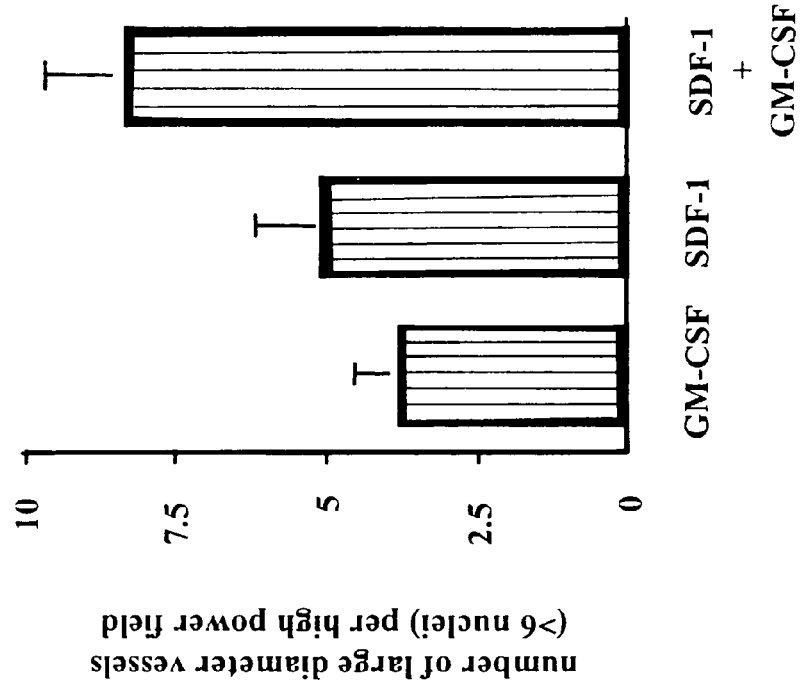

FIG. 19: (a) Shows intramyocardial injection of SDF-1 induces neovascularization at the peri-infarct region and (b) protects cardiomyocytes at the peri-infarct region against apoptosis.

Figure 20B:
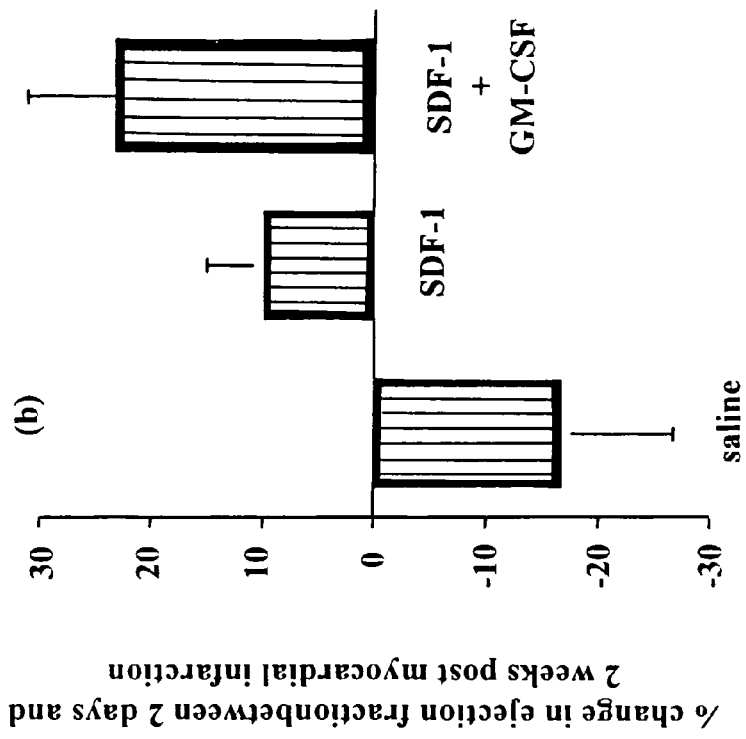

FIG. 20: (a) Shows intramyocardial administration of SDF-1 alone, and synergistically with GM-CSF induces cardiomyocyte regeneration at the peri-infarct region, and (b) improves cardiac function.

Figure 21B:
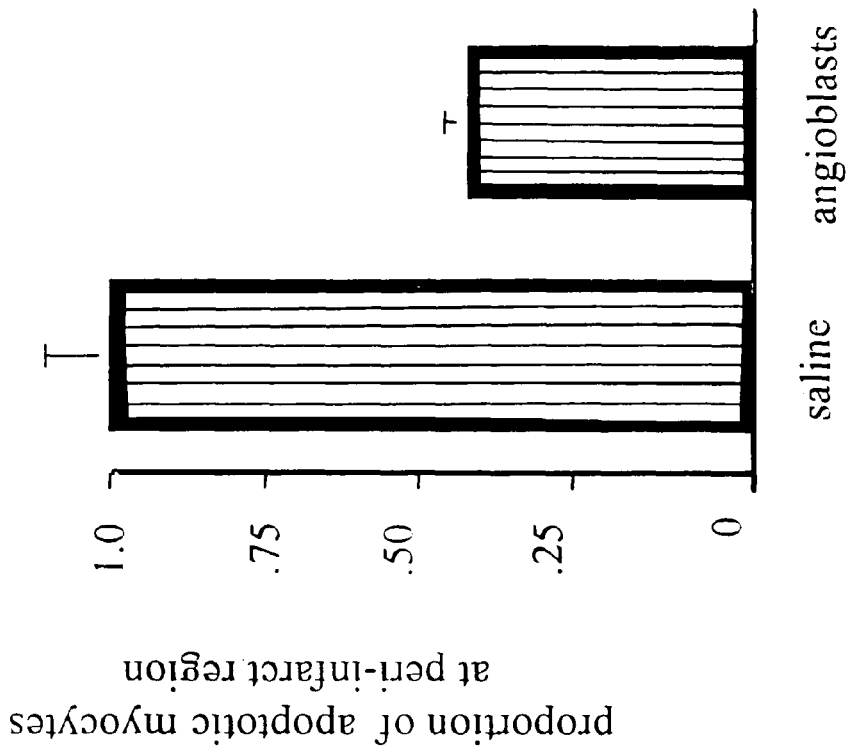
Figure 21A:
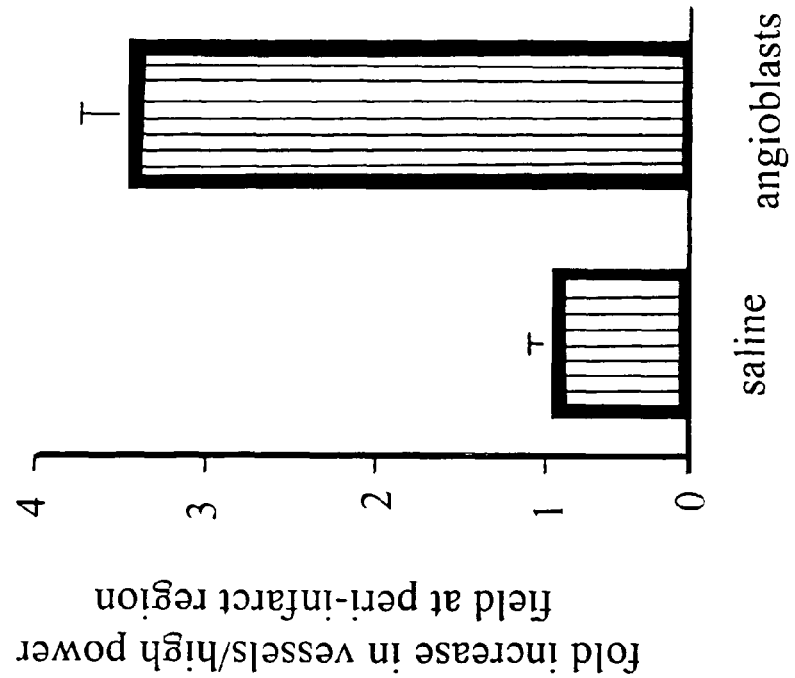

FIG. 21: (a) Shows Human angioblasts, or endothelial progenitor cells, induce neovascularization as early as 5 days post-infarct. (b) Shows Human angioblasts, or endothelial progenitor cells protect peri-infarct cardiomyocytes against apoptosis as early as 5 days post infarct.

Figure 22A:
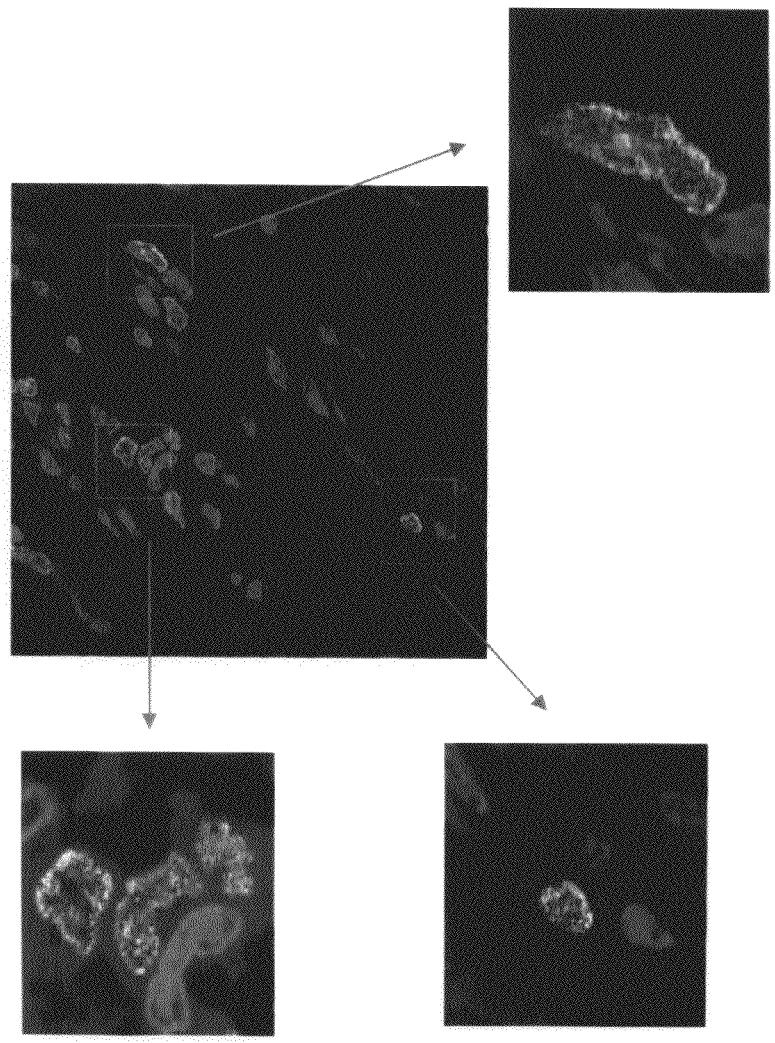
Figure 22B:
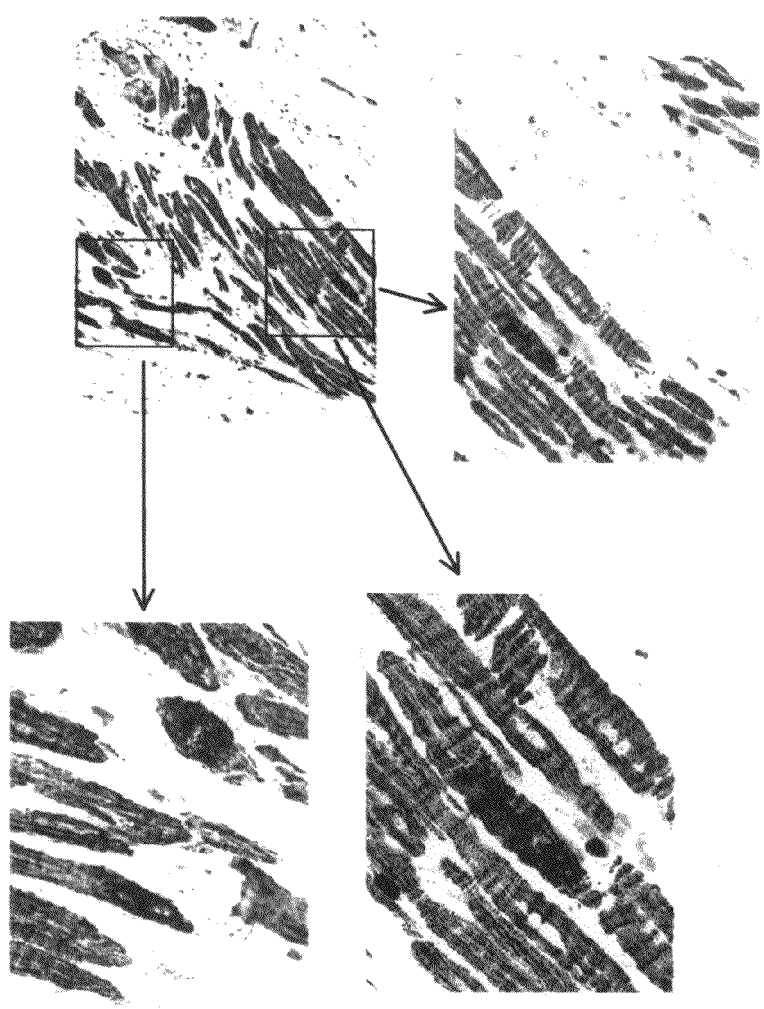
Figure 22C:
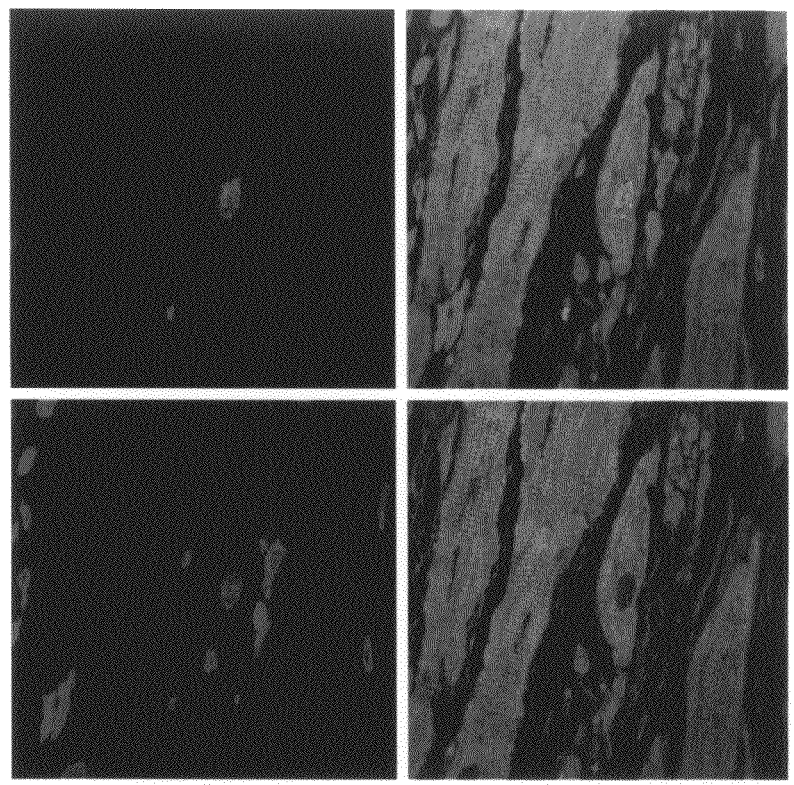

FIG. 22: (a) Shows animals receiving human bone marrow-derived CD34+ cells demonstrated numerous clusters of small, cycling cells at the peri-infarct region that were of rat origin, as defined by a monoclonal antibody specific for rat Ki67. (b) Shows tissues obtained from animals sacrificed at two weeks after human CD34+ administration no longer demonstrated clusters of small, cycling cardiomyocyte progenitors, but instead a high frequency of large, mature rat cardiomyocytes at the peri-infarct region with detectable DNA activity, as determined by dual staining with mAbs reactive against cardiomyocyte-specific troponin I and mAbs reactive against rat Ki67. (c) Shows cycling by the same staining.

Figure 23:
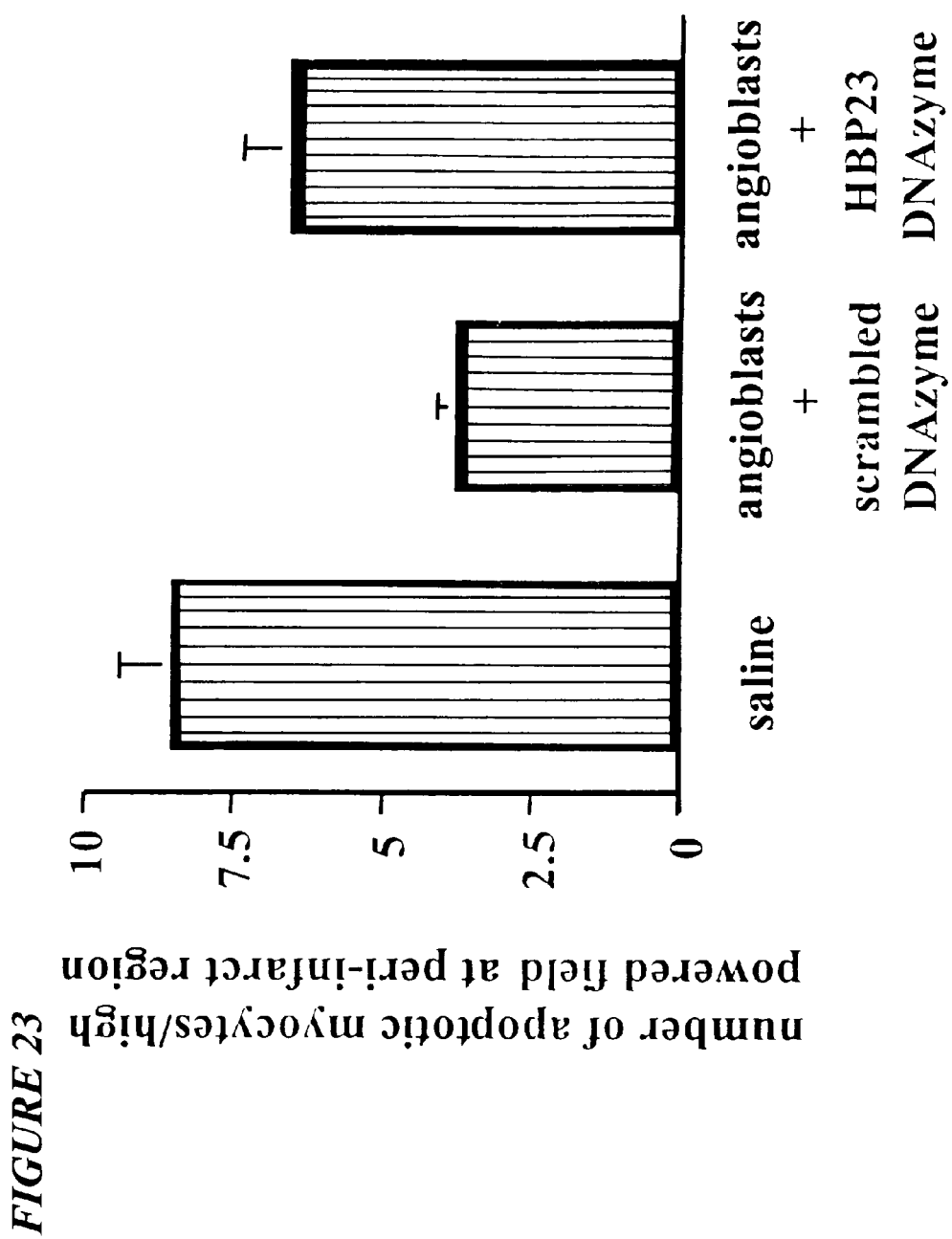

FIG. 23: Shows by RT-PCR, HBP23 mRNA levels in rat hearts decreased at two weeks post-LAD ligation by a mean of 34% compared with normal rat hearts.

FIG. 24: (a) Shows a DNA enzyme against HBP23 cleaved the 23-base oligonucleotide synthesized from the sequence of rat HBP23 mRNA, in a dose- and time-dependent manner. (b) Shows densitometric analysis of RT-PCR products following reverse transcription of cellular mRNA, demonstrating the HBP23 DNA enzyme inhibited steady-state mRNA levels in cultured rat cells by over 80% relative to the scrambled DNA.

Figure 25A:
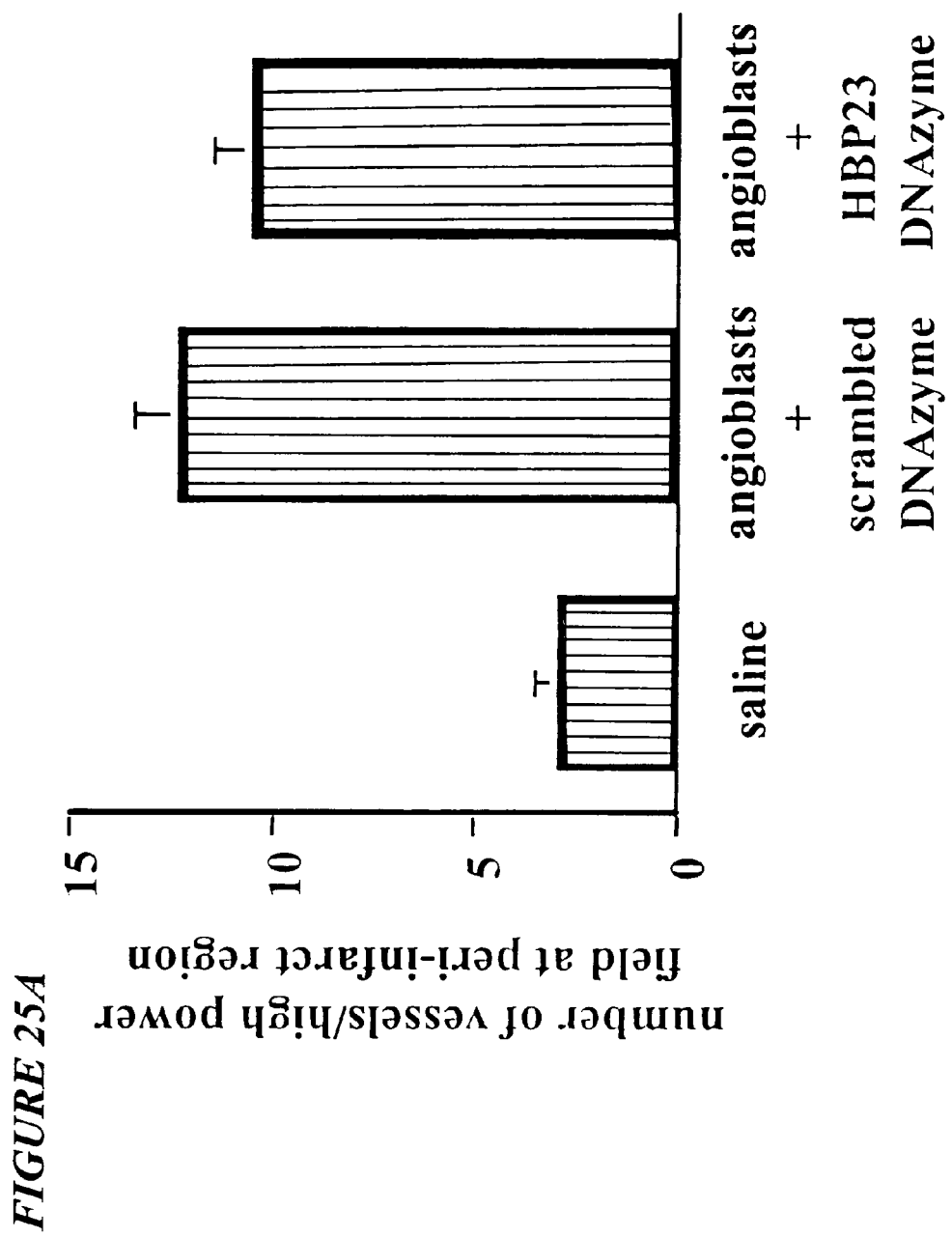
Figure 25B:
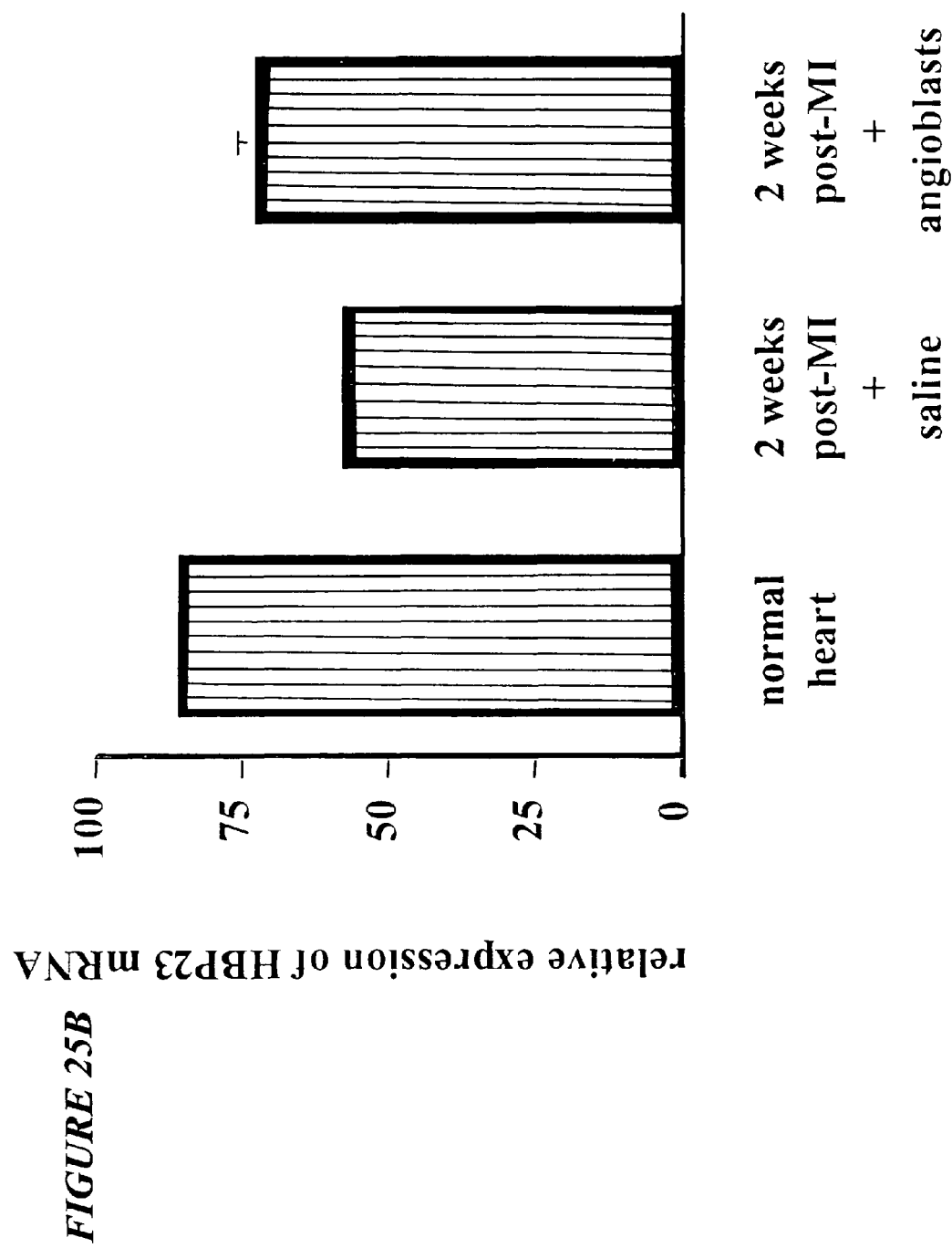
Figure 25C:
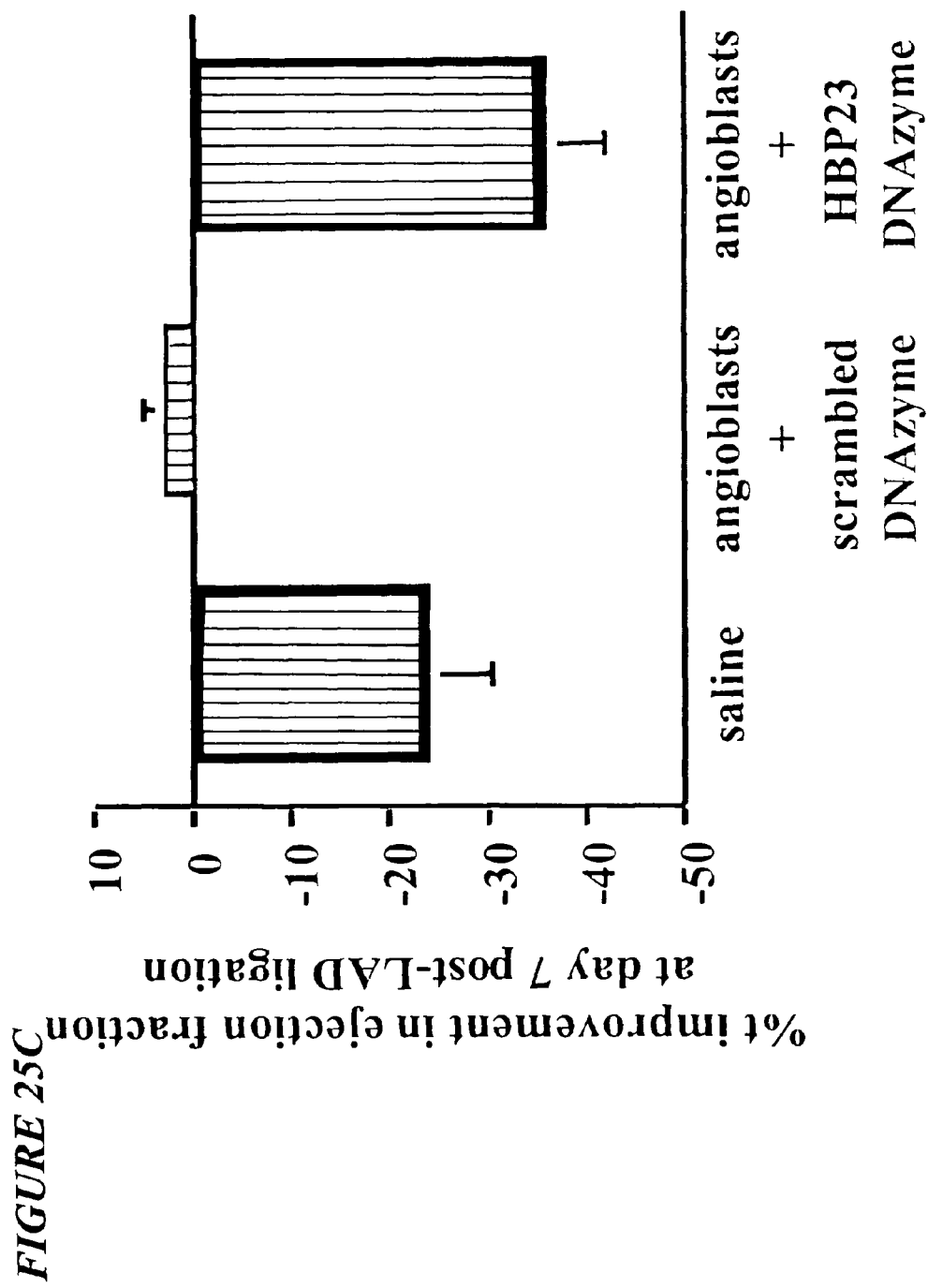

FIG. 25: (a) Shows HBP23 DNA enzyme had no effect on induction of neovascularization by human bone marrow angioblasts, no increased myocardial capillary density in comparison to saline controls is seen. (b) Shows injection of the HBP23 DNA enzyme, but not the scrambled control, abrogated the anti-apoptotic effects of neovascularization. (c) Shows injection of the HBP23 DNA enzyme, but not the scrambled control, abrogated the improvement in cardiac function.

Figure 26:
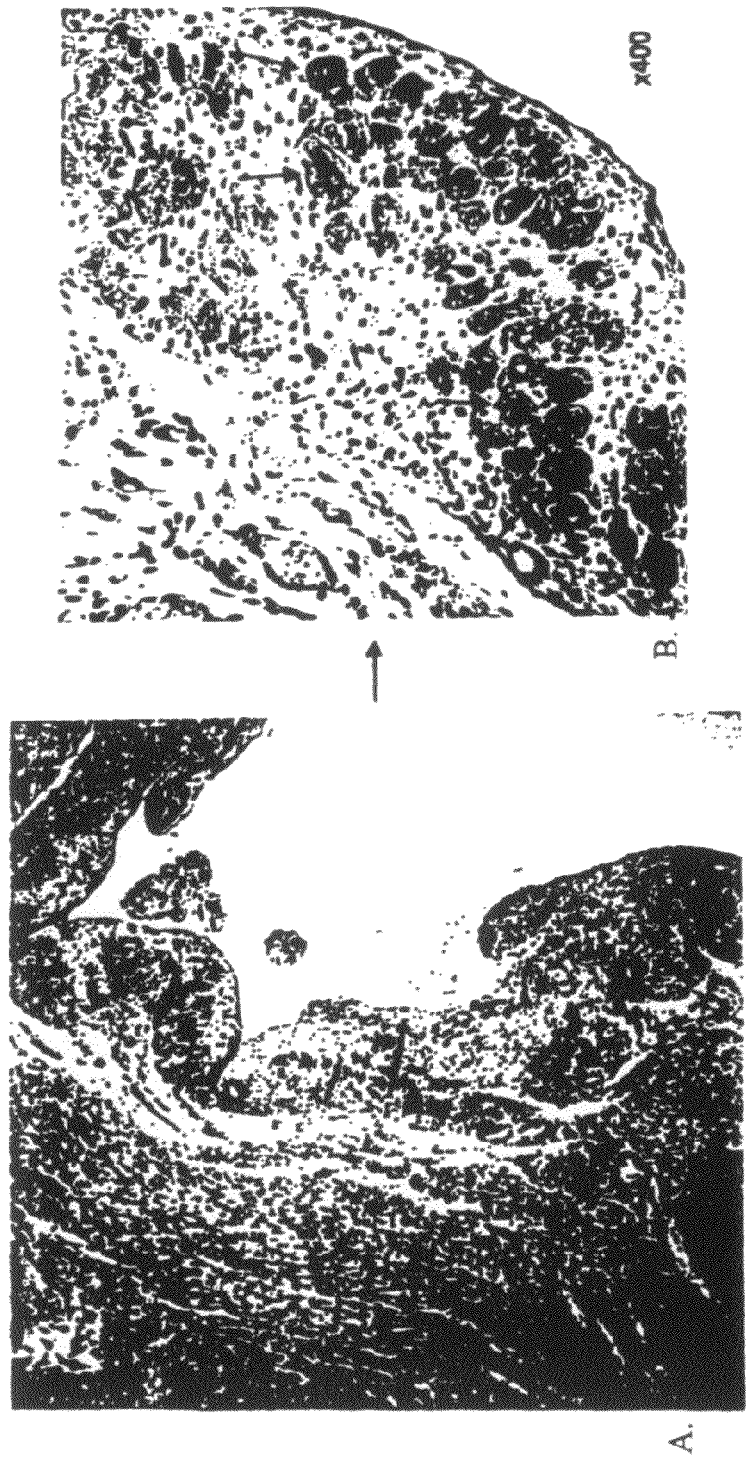

FIG. 26: (a) This figure shows the pattern of CXCR4 expression following acute myocardial ischemia is focal and peri-infarct. (b) Myocardial infarct bed two weeks post myocardial infarction from a representative animal shows CXCR4 staining in dark gray expressed in peri-infarct cardiomyocytes.

Figure 27:
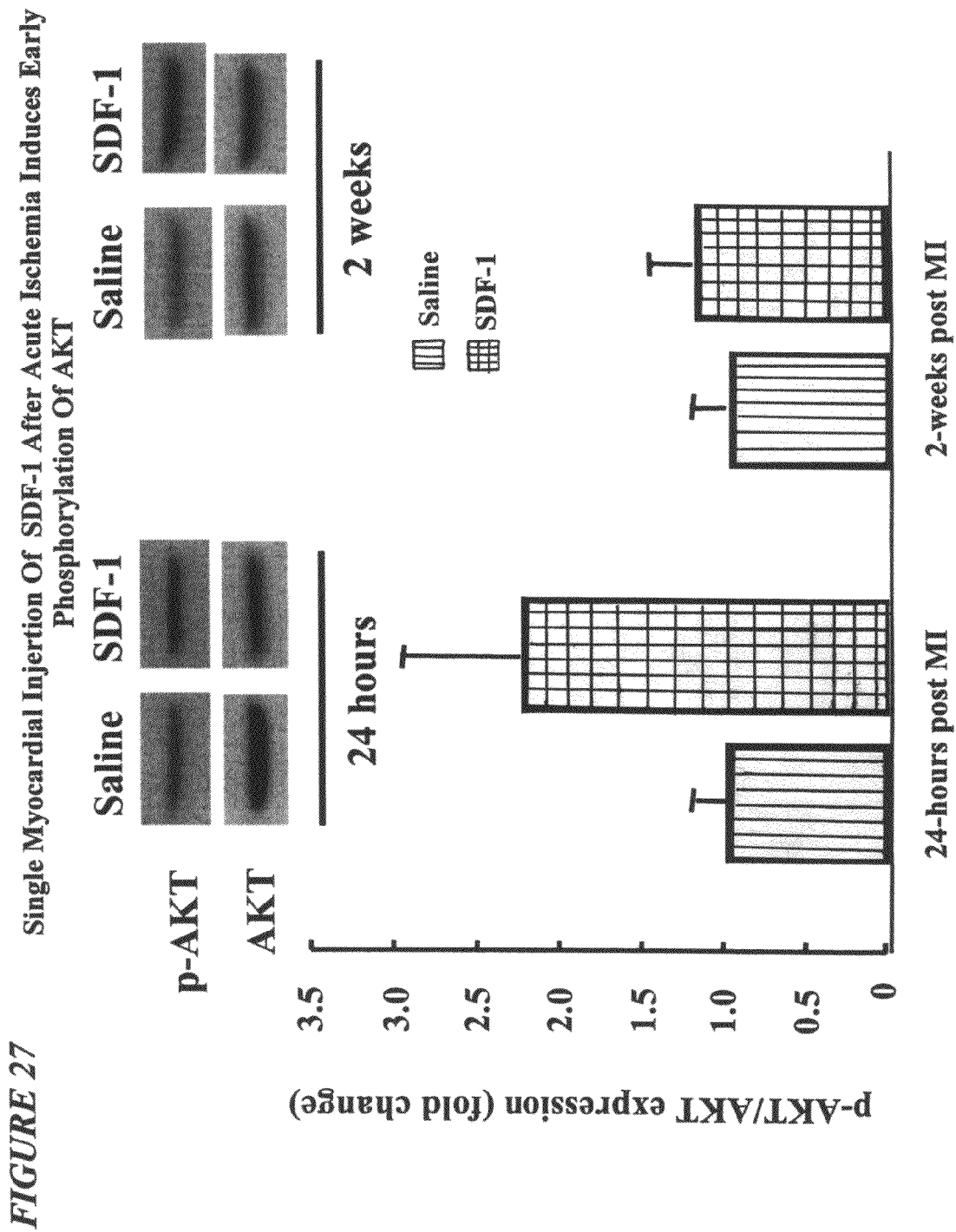

FIG. 27: Single myocardial injection of SDF-1 after acute ischemia induces early phosphorylation of protein kinase B (AKT). SDF-1 intramyocardial administration (4 ug/kg) at time of infarction results in significant early phosphorylation of AKT at 24 hours post-myocardial infarction compared to animals receiving saline controls. This effect was not measurable at two weeks post-myocardial infarction.

Figure 28:
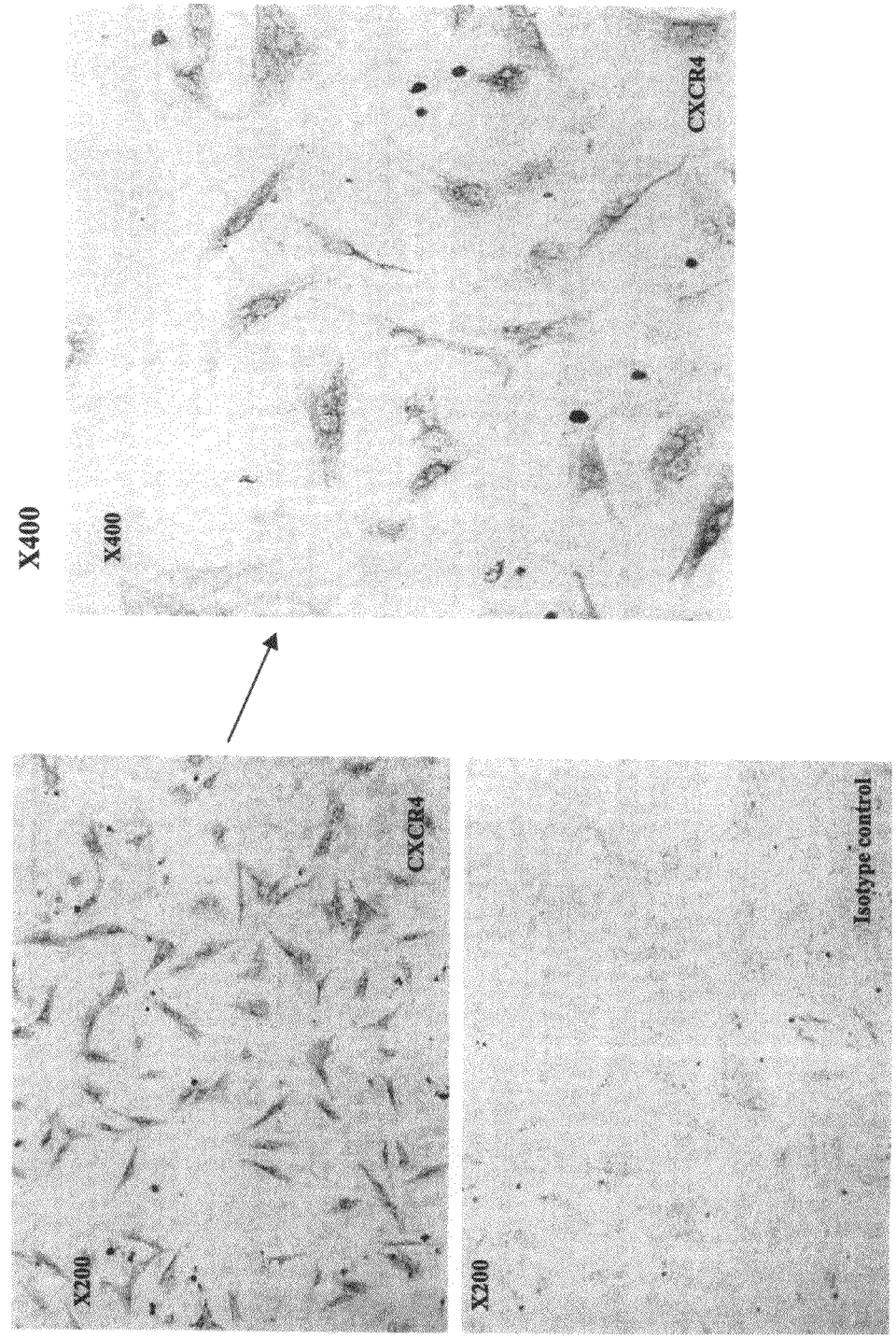

FIG. 28: Cultured rat neonatal cardiomyocytes express CXCR4. Cultured rat neonatal cardiomyocytes in vitro highly express CXCR4 throughout the cytoplasm as defined by immunohistochemical staining using a mAb that cross reacts with rat CXCR4 (dark gray in X200 and X400).

FIG. 29: SDF-1 induces phosphorylation of AKT and ERK in rat neonatal cariomyocytes in time dependent manner. The left hand panel shows optimal phosphorylation of AKT as early as five minutes when cultured rat neonatal cardiomyocytes are cultured with 100 nM of SDF-1. Right hand panel similarly demonstrates maximal ERK phosphorylation at ten minutes as defined by western blot analysis.

Figure 31:
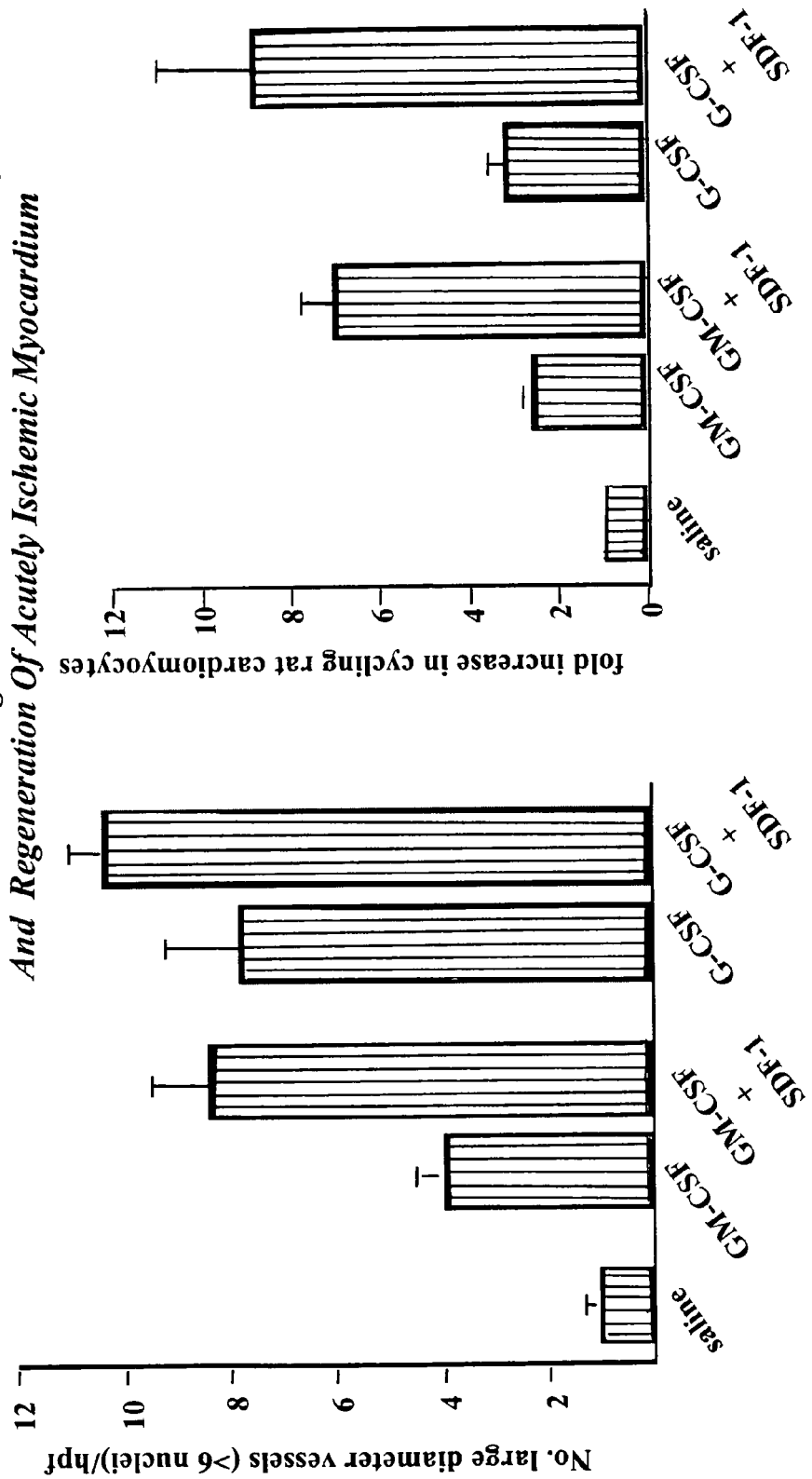

FIG. 31: Intracardiac administration of SDF-1 augments CSF-induced neovascularization and regeneration following acute ischemia. The left hand panel shows that the combination of subcutaneous G-CSF and intracardiac SDF-1 administration results in slightly higher numbers of large diameter blood vessels as defined by having greater than 6 nuclei per high power field. The right hand panel shows similar ratios are observed with the number of cardiomyocytes entering cell cycle as defined by KI67 and troponin I co-staining at two weeks post myocardial infarction.

Figure 32:
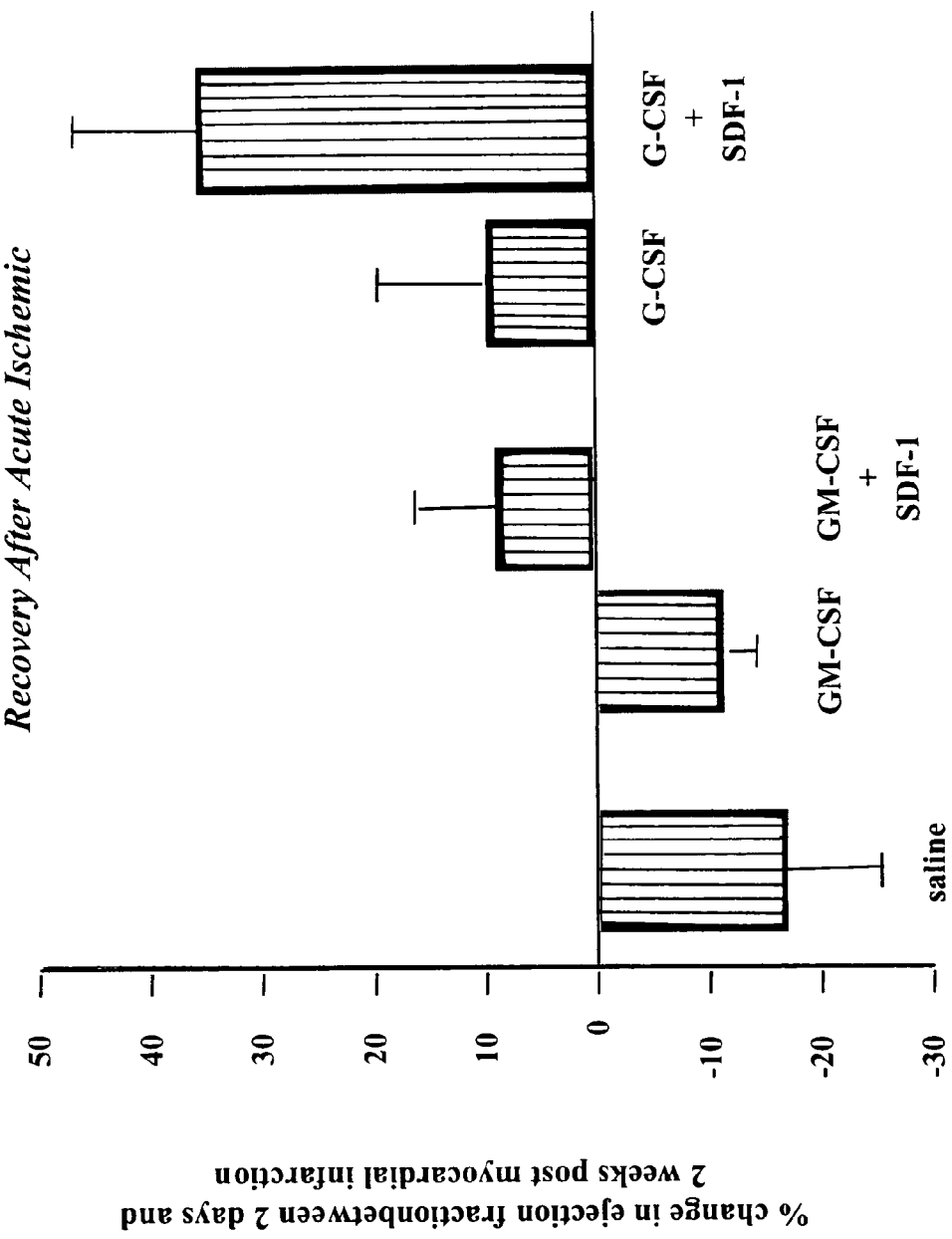

FIG. 32: Intracardiac administration of SDF-1 augments CSF-induced functional myocardial recovery following myocardial ischemia. The combination of subcutaneous G-CSF and intracardiac SDF-1 administration results in over a 35% improvement in ejection fraction as defined by M-mode echocardiography at two weeks post myocardial infarction. In contrast animals receiving saline or only of subcutaneous GM-CSF had an additional regression in cardiac functional capacity.

Figure 30:
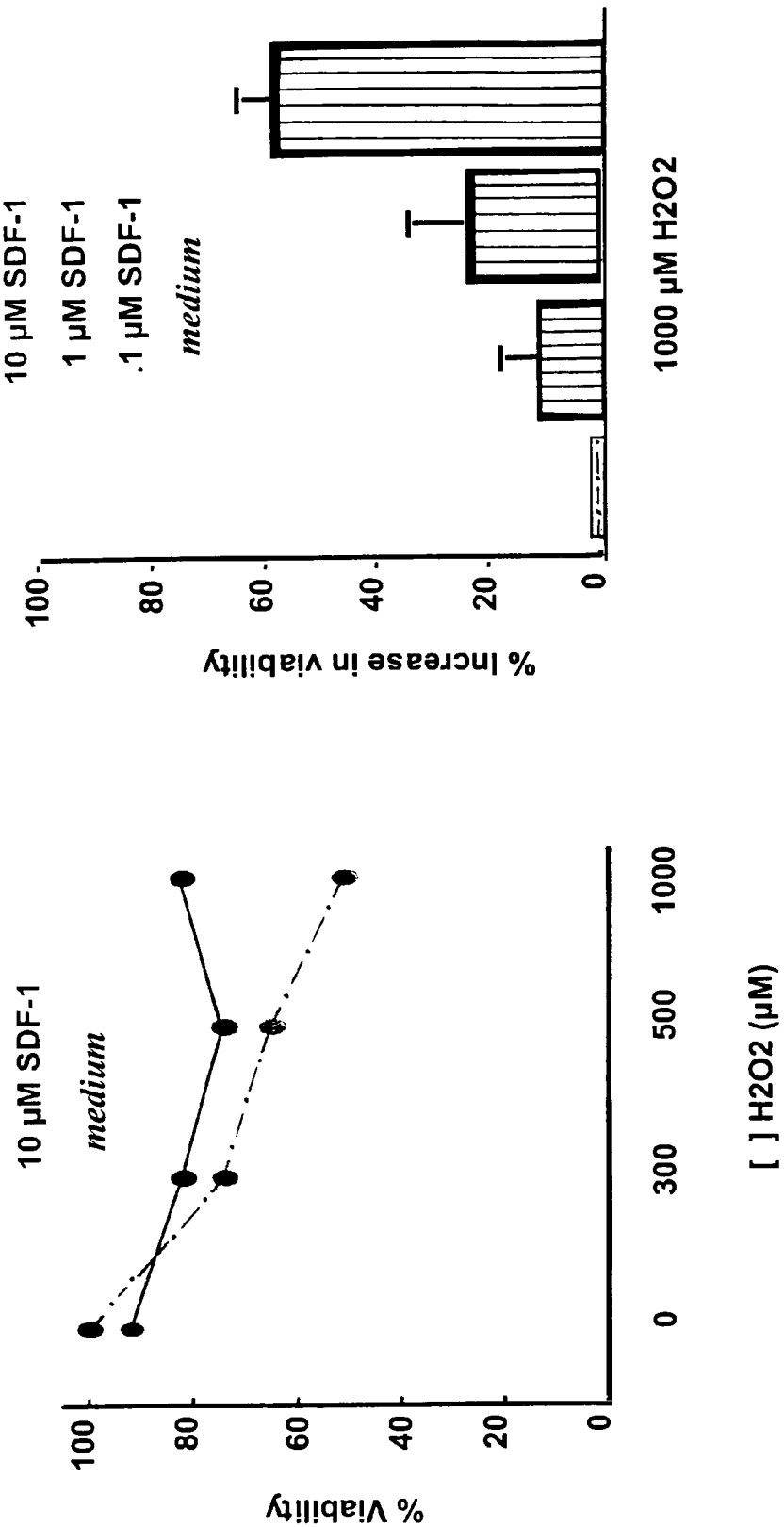

FIG. 30: SDF-1 protects rat neonatal cardiomyocytes against $H_2O_2$-induced apoptosis in a dose dependent manner. The left hand panel demonstrates the protective effect of SDF-1 using the highest concentration (10 μM). The right hand panel demonstrates at the highest concentration of $H_2O_2$ the protective effects of SDF-1 on cardiomyocyte apoptotic death following $H_2O_2$ stimulation is dose dependent with 10 μM having maximal effects. Medium=no SDF.

DETAILED DESCRIPTION

As used herein, "VEGF" is defined as vascular endothelial growth factor. "VEGF-R" is defined as vascular endothelial growth factor receptor. "FGF" is defined as fibroblast growth factor. "IGF" is defined as Insulin-like growth factor. "SCF" is defined as stem cell factor. "G-CSF" is defined as granulocyte colony stimulating factor. "M-CSF" is defined as macrophage colony stimulating factor. "GM-CSF" is defined as granulocyte-macrophage colony stimulating factor. "MAPK" is mitogen-activated protein kinase. "MCP" is defined as monocyte chemoattractant protein. "AKT" is a serine/threonine kinase also known as protein kinase B (PKB). "ERK" is extracellular signal-regulated protein kinase.

As used herein "angioblasts" is synonymous with the term "endothelial progenitor cells".

As used herein, "CXC" chemokine refers to the structure of the chemokine. Each "C" represents a cysteine and "X" represents any amino acid. "CXCR4" refers to CXC receptor 4.

As used herein, "CC" chemokine refers to the structure of the chemokine. Each "C" represents a cysteine.

A "cardiac progenitor cell" refers to a cell that is resident in the heart, or that comes into the heart from elsewhere after acute ischemia, is smaller than mature cardiomyocytes, expresses alpha sarcomeric actin but is negative for troponin, is normally quiescent but can be induced to go into cell cycle as defined by positive Ki67 staining. "Cardiac progenitor cell" may be used synonymously with "cardiomyocyte progenitor cell".

"Catalytic" shall mean the functioning of an agent as a catalyst, i.e. an agent that increases the rate of a chemical reaction without itself undergoing a permanent structural change.

"Nucleic acid" shall include without limitation any nucleic acid, including, without limitation, DNA, RNA, oligonucleotides, or polynucleotides, and analogs or derivatives thereof. The nucleotides that form the nucleic acid may be nucleotide analogs or derivatives thereof. The nucleic acid may incorporate non nucleotides.

"Nucleotides" shall include without limitation nucleotides and analogs or derivatives thereof. For example, nucleotides may comprise the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Proliferation" and "regeneration" are used synonymously when referring to cardiomyocytes in this application. "Proliferation" in respect to cardiomyocytes, shall mean a fold increase in proportion of cardiomyocytes entering the cell cycle relative to untreated rat heart.

"Systemic" administration includes, not is not limited to, intramuscular, sub-cutaneous, intravascular, and intraperitoneal administration. In other forms of administration, each and any of the agents may be administered intracoronarily, intramyocardially, and by stent, scaffold or slow release formation also.

"Tissue" includes heart tissue and, in that embodiment, "cells" include cardiomyocytes. "Tissue" may also include lung, brain, gastrointestinal, liver, kidney and other tissues. "Cells" also includes stem cells which can differentiate into the cell type being lost or progenitors of the cell type being lost in the disorder of the tissue.

"Trafficking" means the blood-borne migration of cells, in particular angioblast/endothelial progenitor cells.

This invention provides a method of treating a disorder of a subject's heart involving loss of cardiomyocytes which comprises administering to the subject a composition comprising an amount of a human stromal-derived factor-1 and an amount of a human granulocyte-colony stimulating factor, the composition being administered in an amount effective to cause proliferation of cardiomyocytes within the subject's heart so as to thereby treat the disorder.

This invention further provides the instant method, wherein the human stromal-derived factor-1 is human stromal-derived factor-1α, human stromal-derived factor-1β, or human stromal-derived factor-1γ.

This invention further provides the instant method, wherein the tissue is heart tissue and the cells are cardiomyocytes. This invention further provides the instant method, wherein the disorder comprises myocardial infarction, congestive heart failure, chronic ischemia, or ischemic disease.

This invention further provides the instant method, further comprising administering to the subject an amount of one or more of a human granulocyte macrophage-colony stimulating factor, a human interleukin-8, a human vascular endothelial growth factor, a human fibroblast growth factor, a human Gro family chemokine, human endothelial progenitor cells, or a pro-angiogenic agent, the amount, or if appropriate amounts, thereof being effective to cause proliferation of cardiomyocytes within the subject's heart so as to thereby treat the disorder.

This invention further provides the instant method, wherein the composition is administered intramyocardially, intracoronarily, via a stent, a scaffold, or a slow-release formulation.

This invention also provides a method of treating a subject suffering from a disorder of a tissue involving loss and/or apoptosis of cells of the tissue which comprises administering to the subject a composition comprising an amount of an agent which induces phosphorylation and/or activation of protein kinase B, the composition being administered in an amount effective to cause proliferation of the cells and/or inhibit apoptosis of the cells of the tissue within the subject so as to thereby treat the disorder.

This invention further provides the instant method, wherein the agent is human human stromal-derived factor-1α, human stromal-derived factor-1β, or human stromal-derived factor-1γ.

This invention further provides the instant method, wherein the tissue is heart tissue and the cells are cardiomyocytes. This invention further provides the instant method, wherein the disorder from which the subject is suffering comprises myocardial infarction, congestive heart failure, chronic ischemia, or ischemic disease.

This invention further provides the instant method, wherein the tissue is heart tissue and the cells are progenitors of cardiomyocytes or stem cells that differentiate to cardiomyocytes.

This invention further provides the instant method, wherein the tissue is striated muscle, liver, kidney, neuronal or gastrointestinal tissue.

This invention further provides the instant method, wherein the agent is insulin, endothelin-1, urocrotin, cardiotropin-1, erythropoietin, leukemia inhibitory factor-1, tumor necrosis factor-alpha.

This invention further provides the instant method, further comprising administering an amount of one or more of a human granulocyte-colony stimulating factor, a human stromal-derived factor-1, a human granulocyte macrophage-colony stimulating factor, a human interleukin-8, a human vascular endothelial growth factor, a human fibroblast growth factor, a human Gro family chemokine, human endothelial progenitor cells, or a pro-angiogenic agent, the amount, or if appropriate amounts, effective to cause proliferation of the cells and/or inhibit apoptosis of the cells of the tissue of the subject so as to thereby treat the disorder.

This invention further provides the instant method, wherein the composition is administered intramyocardially, intracoronarily, via a stent, a scaffold, a slow-release formulation, intramuscularly, intravenously, intra-arterially, or subcutaneously.

This invention also provides a composition comprising a human stromal-derived factor-1 and a human granulocyte-colony stimulating factor.

This invention also provides a method of treating a subject suffering from a disorder of a tissue involving loss and/or apoptosis of cells of the tissue which comprises administering to the subject a composition comprising an amount of an agent which induces phosphorylation and/or activation of an extracellular signal-regulated protein kinase, the composition being administered in an amount effective to inhibit apoptosis and/or cause proliferation of the cells of the tissue within the subject so as to thereby treat the disorder.

This invention further provides the instant method, wherein the agent is human human stromal-derived factor-1α, human stromal-derived factor-1β, or human stromal-derived factor-1γ.

This invention further provides the instant method, wherein the tissue is heart tissue and the cells are cardiomyocytes. This invention further provides the instant method, wherein the disorder from which the subject is suffering comprises myocardial infarction, congestive heart failure, chronic ischemia, or ischemic disease.

This invention further provides the instant method, wherein the tissue is heart tissue and the cells are progenitors of cardiomyocytes or stem cells that differentiate to cardiomyocytes.

This invention further provides the instant method, further comprising administering an amount of one or more of a human granulocyte-colony stimulating factor, a human stromal-derived factor-1, a human granulocyte macrophage-colony stimulating factor, a human interleukin-8, a human vascular endothelial growth factor, a human fibroblast growth factor, a human Gro family chemokine, human endothelial progenitor cells, an activator of protein kinase B, or a pro-angiogenic agent, the amount, or if appropriate amounts, thereof being effective to inhibit apoptosis and/or cause proliferation of the cells of the tissue within the subject so as to thereby treat the disorder.

This invention further provides the instant method, wherein the agent is administered intramyocardially, intracoronarily, via a stent, a scaffold, or a slow-release formulation, intramuscularly, intravenously, intra-arterially, or subcutaneously.

This invention also provides the method of treating a subject suffering from a disorder of a tissue involving loss and/or apoptosis of cells of the tissue which comprises administering to the subject a composition comprising an amount of an agent which induces activation of CXCR4, the composition being administered in an amount effective to cause proliferation of the cells and/or inhibit apoptosis of the cells of the tissue within the subject so as to thereby treat the disorder.

This invention further provides the instant method, wherein the tissue is heart tissue and the cells are cardiomyocytes. This invention further provides the instant method, wherein the agent is administered intramyocardially or intracoronarily via a stent, a scaffold, or a slow-release formulation.

This invention further provides the instant method, wherein the agent is administered systemically.

This invention further provides the use of an amount of a human stromal-derived factor-1 and an amount of a human granulocyte-colony stimulating factor for the manufacture of a composition for treating a disorder of a subject's heart involving loss of cardiomyocytes.

This invention further provides the use of an agent which induces phosphorylation and/or activation of protein kinase B for the manufacture of a composition for treating a disorder of a subject's tissue involving loss of the cells of the tissue.

This invention further provides the use of an amount of an agent which induces phosphorylation and/or activation of extracellular signal regulated protein kinase for the manufacture of a composition for treating a disorder of a subject's tissue involving loss of the cells of the tissue.

This invention further provides the use of an amount of an agent which induces activation of CXCR4 for the manufacture of a composition for treating a disorder of a subject's tissue involving loss of cells of the tissue.

This invention provides a method of treating a disorder of a subject's heart involving loss of cardiomyocytes which comprises administering to the subject an amount of an agent effective to cause cardiomyocyte proliferation within the subject's heart so as to thereby treat the disorder.

In one embodiment the agent is human endothelial progenitor cells. In one embodiment the endothelial progenitor cells are bone marrow-derived. In another they are derived from cord blood, or embryonic or fetal sources. Effective amounts of endothelial progenitor cells sufficient to cause cardiomyocyte proliferation can be done based on animal data using routine computational methods. In one embodiment the effective amount is about $1.5 \times 10^5$ endothelial progenitor cells per kg body mass to about $3 \times 10^5$ per kg body mass. In another embodiment the effective amount is about $3 \times 10^5$ per kg body mass to about $4.5 \times 10^5$ endothelial progenitor cells per kg body mass. In another embodiment the effective amount is about $4.5 \times 10^5$ per kg body mass to about $5.5 \times 10^5$ endothelial progenitor cells per kg body mass. In another embodiment the effective amount is about $5.5 \times 10^5$ per kg body mass to about $7 \times 10^5$ endothelial progenitor cells per kg body mass. In another embodiment the effective amount is about $7 \times 10^5$ per kg body mass to about $1 \times 10^6$ endothelial progenitor cells per kg body mass. In another embodiment the effective amount is about $1 \times 10^6$ per kg body mass to about $1.5 \times 10^6$ endothelial progenitor cells per kg body mass. In one embodiment the effective amount of human endothelial progenitor cells is between about $1.5 \times 10^6$ and $4.5 \times 10^6$ endothelial progenitor cells per kg of the subject's body mass and in a preferred embodiment the effective amount is about $5 \times 10^5$ endothelial progenitor cells per kg of the subject's body mass.

In one embodiment the endothelial progenitor cells are allogeneic with respect to the subject. In differing embodiments the subject is an adult or an embryo or a fetus. In another embodiment the endothelial progenitor cells are derived from cloned autologous embryonic stem cells.

In one embodiment the agent induces expression of a mRNA encoding a peroxiredoxin. The expression of peroxiredoxin mRNA may be increased, for example, by administration of 2(3)-t-butyl-4-hydroxyanisole (BHA) (see 106) which has been shown to increase expression of Peroxiredoxin-1 when administered by diet. Alternatively, local control of $O_2$ can have the same effect (see 107). Peroxiredoxin mRNA expression, such as that of thiol peroxidases, may also be induced by heme, cadmium or cobalt (see 108). Peroxiredoxins include, but are not limited to, PAG, HBP23, MSP23, NKEF.

In another embodiment the agent induces expression of a mRNA encoding NF-E2-related factor 2 (Nrf2). Cytoplasmic NF-E2-related factor 2 (Nrf2) expression can be indirectly increased by raising free Nrf2 levels. Since Nrf2 is tightly bound to keap1 in the cytoplasm then reducing expression of keap1 mRNA is a suitable target e.g. by keap1 antisense oligonucleotides or catalytic nucleic acids (see 109 for keap1). Also, blocking the interaction between Nrf2 and Keap1 by inhibiting the interaction of the Neh2 domain of Nrf2 and the DGR domain of keap1, e.g. by using the entire Neh2 domain of nrf2, amino acids 1-73, or only the hydrophilic region, amino acids 33-73 (see 109) will increase free cytoplasmic Nrf-2. In another embodiment the agent induces dissociation of a Nrf2 protein from a Keap-1. In another embodiment the agent inhibits association of a Nrf2 protein with a Keap-1. In another embodiment the agent inhibits association of a thiol reductase thioredoxin with a VDUP-1 protein. In another embodiment the agent inhibits c-Abl tyrosine kinase activation. In a further embodiment the agent is STI-571.

In one embodiment the agent is a CXC chemokine. In further embodiments the agent is Stromal-Derived Factor-1, Il-8 or Gro-Alpha. In one embodiment the amount of CXC chemokine administered is between 0.2 and 5 μg/ml at a max volume of 10 ml for a 70 kg human subject. In a preferred embodiment the amount is about 1 μg/ml. In one embodiment the agent is an inhibitor of plasminogen activator inhibitor-1. In another embodiment the agent is an antibody directed against an epitope of CXCR4. In one embodiment the amount of antibody directed against an epitope of CXCR4 is between 25 and 75 μg/ml, at a max volume of 10 ml for a 70 kg human subject. A simple calculation is performed for subjects of different mass. In a preferred embodiment the amount is about 50 μg/ml.

In differing embodiments the agent is Stromal-Derived Factor-1 alpha or Stromal-Derived Factor-1 beta. In differing embodiments the chemokine can be administered intramyocardially, intracoronary, and/or via a stent, a scaffold, or as a slow-release formulation.

In differing embodiments the agent is G-CSF, GM-CSF, or a Gro family chemokine. In a further embodiment the agent is Gro alpha.

SDF variants may be employed in the present invention. For example, a mutein, an analog, fusion protein, functional derivative, isoform, allelic variant or effective fragment of SDF. The amino acid sequence of a number of different native mammalian SDF-1 alpha, beta and gamma proteins are known, including human, rat, mouse, and cat. See, e.g., Shirozu et al., Genomics, 28: 495, 1995; Tashiro et al., Science 261: 600, 1993; Nishimura et al., Eur. J. Immunogenet. 25: 303, 1998; and GenBank Accession No. AF189724. A preferred form of SDF-1 protein is a purified native SDF-1 protein that has an amino acid sequence identical to one of the foregoing mammalian SDF-1 proteins. Variants of native mammalian SDF-1 proteins such as fragments, analogs and derivatives of native mammalian SDF-1 proteins may also be used in the invention. Such variants include, e.g., a polypeptide encoded by a naturally occurring allelic variant of native SDF-1 gene (i.e., a naturally occurring nucleic acid that encodes a naturally occurring mammalian SDF-1 protein), a polypeptide encoded by an alternative splice form of a native SDF-1 gene, a polypeptide encoded by a homolog of a native SDF-1 gene, and a polypeptide encoded by a non-naturally occurring variant of a native SDF-1 gene. SDF-1 protein variants have a peptide sequence that differs from a native SDF-1 protein in one or more amino acids. The peptide sequence of such variants can feature a deletion, addition, or substitution of one or more amino acids of a native SDF-1 protein. Amino acid insertions are preferably of about 1 to 4 contiguous amino acids, and deletions are preferably of about 1 to 10 contiguous amino acids. In some applications, variant SDF-1 proteins substantially maintain a native SDF-1 protein functional activity (e.g., the ability to cause cellular chemotaxis). For other applications, variant SDF-1 proteins lack or feature a significant reduction in a SDF-1 protein functional activity. Where it is desired to retain a functional activity of native SDF-1 protein, preferred SDF-1 protein variants can be made by expressing nucleic acid molecules within the invention that feature silent or conservative changes. Variant SDF-1 proteins with substantial changes in functional activity can be made by expressing nucleic acid molecules within the invention that feature less than conservative changes.

SDF-1 protein fragments corresponding to one or more particular motifs and/or domains or to arbitrary sizes, for example, at least 5, 10, 25, 50, or 75 amino acids in length are within the scope of the present invention. Isolated peptidyl portions of SDF-1 proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a SDF-1 protein of the present invention may be arbitrarily divided into fragments of desired length with no overlap, of the fragments, or preferably divided into overlapping fragments of a desired length. The fragments can be produced (recombinantly or by chemical synthesis) and tested to identify those peptidyl fragments which can function as either agonists or antagonists of native SDF-1 protein. Another aspect of the present invention concerns recombinant forms of the SDF-1 proteins. Recombinant polypeptides preferred by the present invention, in addition to a native SDF-1 protein, are encoded by a nucleic acid that has at least 85% sequence identity (e.g., 85, 86, 87, 88, 89, 90, 91, 92, 93, 94, 95, 96, 97, 98, 99, 100%) with the nucleic acid sequence of a gene encoding a mammalian SDF-1 protein. In a preferred embodiment, variant SDF-1 proteins have one or more functional activities of native SDF-1 protein.

SDF-1 protein variants can be generated through various techniques known in the art. For example, SDF-1 protein variants can be made by mutagenesis, such as by introducing discrete point mutation (s), or by truncation. Mutation can give rise to a SDF-1 protein variant having substantially the same, or merely a subset of the functional activity of native SDF-1 protein. Alternatively, antagonistic forms of the protein can be generated which are able to inhibit the function of a naturally occurring form of the protein, such as by competitively binding to another molecule that interacts with a SDF-1 protein. In addition, agonistic forms of the protein may be generated that constitutively express on or more of the functional activities of a native SDF-1 protein. Other SDF-1 protein variants that can be generated include those that are resistant to proteolytic cleavage, as for example, due to mutations which alter protease target sequences. Whether a change in the amino acid sequence of a peptide results in a variant having one or more functional activities of a native SDF-1 protein can be readily determined by testing the variant for a native SDF-1 protein functional activity.

As another example, SDF-1 protein variants can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential SDF-1 protein sequences. The synthesis of degenerate oligonucleotides is well known in the art (see for example, Narang, S A (1983) Tetrahedron 39: 3; Itakura et al. (1981) Recombinant DNA, Proc 3rd Cleveland Sympos. Macromolecules, ed. A G Walton, Amsterdam: Elsevier pp 273-289; Itakura et al.

As used herein "a human stromal-derived factor-1" means a polypeptide which has the same or substantially the same amino acid sequence and biological activity as a naturally occurring human stromal-derived factor-1, including specifically, any of human stromal-derived factor-1$\alpha$, 1$\beta$, or 1$\gamma$. The term "human stromal-derived factor-1" thus encompasses polypeptides which have one or more additional amino acids, typically less than 5 additional amino acids at either the N-terminus or the C-terminus or both so long as the biological activity is retained, and specifically includes a polypeptide having an N-terminal methionine added to the sequence present in a naturally occurring stromal-derived factor-1. The term also encompasses conjugates with other substances, polyethylene glycol conjugates, i.e. so-called pegylated form of the polypeptide.

As used herein "a human granulocyte-colony stimulating factor" means a polypeptide which has the same or substantially the same amino acid sequence and biological activity as a naturally occurring human granulocyte-colony stimulating factor. The term "human granulocyte-colony stimulating factor" thus encompasses polypeptides which have one or more additional amino acids, typically less than 5 additional amino acids at either the N-terminus or the C-terminus or both so long as the biological activity is retained, and specifically includes a polypeptide having an N-terminal methionine added to the sequence present in a naturally occurring granulocyte-colony stimulating factor. The term also encompasses conjugates with other substances, polyethylene glycol conjugates, i.e. so-called pegylated form of the polypeptide.

As used herein "a human granulocyte macrophage-colony stimulating factor" means a polypeptide which has the same or substantially the same amino acid sequence and biological activity as a naturally occurring human granulocyte macrophage-colony stimulating factor. The term "human granulocyte macrophage-colony stimulating factor" thus encompasses polypeptides which have one or more additional amino acids, typically less than 5 additional amino acids at either the N-terminus or the C-terminus or both so long as the biological activity is retained, and specifically includes a polypeptide having an N-terminal methionine added to the sequence present in a naturally occurring granulocyte macrophage-colony stimulating factor. The term also encompasses conjugates with other substances, polyethylene glycol conjugates, i.e. so-called pegylated form of the polypeptide.

As used herein "a human interleukin 8" means a polypeptide which has the same or substantially the same amino acid sequence and biological activity as a naturally occurring human interleukin 8. The term "human interleukin 8" thus encompasses polypeptides which have one or more additional amino acids, typically less than 5 additional amino acids at either the N-terminus or the C-terminus or both so long as the biological activity is retained, and specifically includes a polypeptide having an N-terminal methionine added to the sequence present in a naturally occurring interleukin 8. The term also encompasses conjugates with other substances, polyethylene glycol conjugates, i.e. so-called pegylated form of the polypeptide.

As used herein "a human vascular endothelial growth factor" means a polypeptide which has the same or substantially the same amino acid sequence and biological activity as a naturally occurring human vascular endothelial growth factor. The term "human vascular endothelial growth factor" thus encompasses polypeptides which have one or more additional amino acids, typically less than 5 additional amino acids at either the N-terminus or the C-terminus or both so long as the biological activity is retained, and specifically includes a polypeptide having an N-terminal methionine added to the sequence present in a naturally occurring vascular endothelial growth factor. The term also encompasses conjugates with other substances, polyethylene glycol conjugates, i.e. so-called pegylated form of the polypeptide.

As used herein "a human fibroblast growth factor" means a polypeptide which has the same or substantially the same amino acid sequence and biological activity as a naturally occurring human fibroblast growth factor. The term "human fibroblast growth factor" thus encompasses polypeptides which have one or more additional amino acids, typically less than 5 additional amino acids at either the N-terminus or the C-terminus or both so long as the biological activity is retained, and specifically includes a polypeptide having an N-terminal methionine added to the sequence present in a naturally occurring fibroblast growth factor. The term also encompasses conjugates with other substances, polyethylene glycol conjugates, i.e. so-called pegylated form of the polypeptide.

In a further embodiment the instant method further comprises administering an effective amount of a second agent that increases the cardiomyocyte proliferation caused by the human endothelial progenitor cells. Effective amounts of the second agent are amounts sufficient to enhance or accelerate cardiomyocyte proliferation in the presence of administered endothelial progenitor cells. In further embodiments the endothelial progenitor cells express CD117, CD34, AC133 or a high level of intracellular GATA-2 activity. In one embodiment the administering comprises injecting directly into the subject's peripheral circulation, heart muscle, left ventricle, right ventricle, coronary artery, cerebro-spinal fluid, neural tissue, ischemic tissue, or post-ischemic tissue.

In one embodiment the second agent is an antisense oligonucleotide which specifically inhibits translation of Vitamin D3 Up-Regulated Protein-1 (VDUP-1) mRNA.

Therapeutically useful targeted inhibition of VDUP-1 protein (SEQ ID NO:2) expression can be achieved through the use of antisense oligonucleotides. Antisense oligonucleotides are small fragments of DNA and derivatives thereof complementary to a defined sequence on a specified mRNA. A VDUP-1 antisense oligonucleotide specifically binds to targets on the VDUP-1 mRNA (SEQ ID NO:1) molecule and in doing so inhibits the translation thereof into VDUP-1 protein (SEQ ID NO:2).

Antisense oligonucleotide molecules synthesized with a phosphorothioate backbone have proven particularly resistant to exonuclease damage compared to standard deoxyribonucleic acids, and so they are used in preference. A phosphorothioate antisense oligonucleotide for VDUP-1 mRNA can be synthesized on an Applied Biosystems (Foster City, Calif.) model 380B DNA synthesizer by standard methods. E.g. Sulfurization can be performed using tetraethylthiuram disulfide/acetonitrile. Following cleavage from controlled pore glass support, oligodeoxynucleotides can be base deblocked in ammonium hydroxide at 60° C. for 8 h and purified by reversed-phase HPLC [0.1M triethylammonium bicarbonate/acetonitrile; PRP-1 support]. Oligomers can be detritylated in 3% acetic acid and precipitated with 2% lithiumperchlorate/acetone, dissolved in sterile water and re-precipitated as the sodium salt from 1 M NaCl/ethanol. Concentrations of the full length species can be determined by UV spectroscopy.

Any other means for such synthesis known in the art may additionally or alternatively be employed. It is well known to use similar techniques to prepare oligonucleotides such as the phosphorothioates and alkylated derivatives.

Hybridization of antisense oligonucleotides with VDUP-1 mRNA interferes with one or more of the normal functions of VDUP-1 1 mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Also, oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof) are included. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, antisense oligonucleotides or the catalytic nucleic acids described below may be formulated in accordance with this invention which are targeted wholly or in part to these associated ribonucleotides as well as to the informational ribonucleotides. The antisense oligonucleotides may therefore be specifically hybridizable with a transcription initiation site region, a translation initiation codon region, a 5' cap region, an intron/exon junction, coding sequences, a translation termination codon region or sequences in the 5'- or 3'-untranslated region. Similarly, the catalytic nucleic acids may specifically cleave a transcription initiation site region, a translation initiation codon region, a 5' cap region, an intron/exon junction, coding sequences, a translation termination codon region or sequences in the 5'- or 3'-untranslated region. As is known in the art, the translation initiation codon is typically 5'-AUG (in transcribed mRNA molecules; 5'-ATG in the corresponding DNA molecule). A minority of genes have a translation initiation codon having the RNA sequence 5'-GUG, 5'UUG or 5'-CUG, and 5'-AUA, 5'-ACG and 5'-CUG have been shown to function in vivo. Thus, the term "translation initiation codon" can encompass many codon sequences, even though the initiator amino acid in each instance is typically methionine in eukaryotes. It is also known in the art that eukaryotic genes may have two or more alternative translation initiation codons, any one of which may be preferentially utilized for translation initiation in a particular cell type or tissue, or under a particular set of conditions. In the context of the invention, "translation initiation codon" refers to the codon or codons that are used in vivo to initiate translation of an mRNA molecule transcribed from a gene encoding VDUP-1, regardless of the sequence(s) of such codons. It is also known in the art that a translation termination codon of a gene may have one of three sequences, i.e., 5'-UAA, 5'-UAG and 5'-UGA (the corresponding DNA sequences are 5'-TAA, 5'-TAG and 5'-TGA, respectively). The term "translation initiation codon region" refers to a portion of such an mRNA or gene that encompasses from about 25 to about 50 contiguous nucleotides in either direction (i.e., 5' or 3') from a translation initiation codon. This region is one preferred target region. Similarly, the term "translation termination codon region" refers to a portion of such an mRNA or gene that encompasses from about 25 to about 50 contiguous nucleotides in either direction (i.e., 5' or 3') from a translation termination codon. This region is also one preferred target region. The open reading frame or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. mRNA splice sites may also be preferred target regions, and are particularly useful in situations where aberrant splicing is implicated in disease, or where an overproduction of a particular mRNA splice product is implicated in disease. Aberrant fusion junctions due to rearrangements or deletions may also be preferred targets.

Once the target site or sites have been identified, antisense oligonucleotides can be chosen which are sufficiently complementary to the target, i.e., hybridize sufficiently well and with sufficient specificity, to give the desired disruption of the function of the molecule. "Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the catalytic nucleic acids. Similarly, catalytic nucleic acids are synthesized once cleavage target sites on the VDUP-1 mRNA molecule.

It is preferred to administer antisense oligonucleotides or catalytic nucleic acids or analogs thereof or other agents to mammals suffering from cardiovascular disease, in either native form or suspended in a carrier medium in amounts and upon treatment schedules which are effective to therapeutically treat the mammals to reduce the detrimental effects of cardiovascular disease. One or more different catalytic nucleic acids or antisense oligonucleotides or analogs thereof targeting different sections of the nucleic acid sequence of VDUP-1 mRNA may be administered together in a single dose or in different doses and at different amounts and times depending upon the desired therapy. The catalytic nucleic acids or antisense oligonucleotides can be administered to mammals in a manner capable of getting the oligonucleotides initially into the blood stream and subsequently into cells, or alternatively in a manner so as to directly introduce the catalytic nucleic acids or antisense oligonucleotides into the cells or groups of cells, for example cardiomyocytes, by such means by electroporation or by direct injection into the heart. Antisense oligonucleotides whose presence in cells can inhibit transcription or protein synthesis can be administered by intravenous injection, intravenous drip, subcutaneous, intraperitoneal or intramuscular injection, orally or rectally. Human pharmacokinetics of certain antisense oligonucleotides have been studied. See (105) incorporated by reference in its entirety. It is within the scale of a person's skill in the art to determine optimum dosages and treatment schedules for such treatment regimens.

Any of the agents employed in this invention can be administered intracoronary or intramyocardially, for example by injection. The agents can be delivered in various means as otherwise discussed, including by stents, such as drug-eluting stents, and in time-release formats such as slow-release. Where the agents are proteins, including but not limited to SDF-1, G-CSF, GM-CSF, and VEGF, the agents can be administered directly or indirectly, or may be administered via induction of gene expression, through gene therapy, adenoviral delivery and other such methods familiar to those skilled in the art.

Doses of the oligonucleotides or analogs thereof of the present invention in a pharmaceutical dosage unit will be an efficacious, nontoxic quantity administered to a human patient in need of cardiomyocyte regeneration (or inhibition of VDUP-1 expression) from 1-6 or more times daily or every other day. Dosage is dependent on severity and responsiveness of the effects of abnormal cardiovascular disease to be treated, with course of treatment lasting from several days to months or until a cure is effected or a reduction of the effects is achieved. Oral dosage units for human administration generally use lower doses. The actual dosage administered may take into account the size and weight of the patient, whether the nature of the treatment is prophylactic or therapeutic in nature, the age, weight, health and sex of the patient, the route of administration, and other factors.

In another embodiment the second agent is a pro-angiogenic agent. In further embodiments the pro-angiogenic agent is vascular endothelial growth factor, fibroblast growth factor or angiopoietin. In another embodiment the second agent induces expression of a pro-angiogenic factor. In a further embodiment the second agent is Hypoxia Inducible Factor-1.

In another embodiment the second agent is a catalytic nucleic acid which specifically inhibits translation of Vitamin D3 Up-Regulated Protein-1 mRNA. In a further embodiment the catalytic nucleic acid comprises deoxyribonucleotides. In another embodiment the catalytic nucleic acid comprises ribonucleotides.

Catalytic nucleic acid molecules can cleave Vitamin D3 Up-Regulated Protein-1 (VDUP-1) mRNA (corresponding DNA shown in SEQ ID NO:1, FIG. 5) at each and any of the consensus sequences therein. Since catalytic ribo- and deoxyribo-nucleic acid consensus sequences are known, and the VDUP-1 Protein mRNA sequence is known, one of ordinary skill could readily construct a catalytic ribo- or deoxyribo nucleic acid molecule directed to any of the VDUP-1 protein mRNA consensus sequences based on the instant specification. In preferred embodiments of this invention the catalytic deoxyribonucleic acids include the 10-23 structure. Examples of catalytic ribonucleic acids include hairpin and hammerhead ribozymes. In preferred embodiments of this invention, the catalytic ribonucleic acid molecule is formed in a hammerhead (50) or hairpin motif (51,52,53), but may also be formed in the motif of a hepatitis delta virus (54), group I intron (60), RNaseP RNA (in association with an RNA guide sequence) (55,56) or *Neurospora* VS RNA (57,58,59).

To target the VDUP-1 mRNA (SEQ ID NO:1), catalytic nucleic acids can be designed based on the consensus cleavage sites 5'-purine:pyrimidine-3' in the VDUP-1 mRNA sequence (104) (see FIGS. 6-10) for cleavage sites on DNA corresponding to the mRNA encoding VDUP-1 (SEQ ID NO:2). Those potential cleavage sites located on an open loop of the mRNA according to RNA folding software e.g. RNADRaw 2.1 are particularly preferred as targets (61). The DNA based catalytic nucleic acids can utilize the structure where two sequence-specific arms are attached to a catalytic core based on the VDUP-1 mRNA sequence. Further examples of catalytic DNA structure are detailed in (62) and (63). Commercially available mouse brain polyA-RNA (Ambion) can serve as a template in the in vitro cleavage reaction to test the efficiency of the catalytic deoxyribonucleic acids. Catalytic RNA, is described above, is designed similarly. Hammerhead ribozymes can cleave any 5'-NUH-3' triplets of a mRNA, where U is conserved and N is any nucleotide and H can be C,U,A, but not G. For example, the sites which can be cleaved by a hammerhead ribozyme in human VDUP-1 mRNA coding region are shown in FIG. 10.

Cleaving of VDUP-1 mRNA with catalytic nucleic acids interferes with one or more of the normal functions of VDUP-1 mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA.

The nucleotides may comprise other bases such as inosine, deoxyinosine, hypoxanthine may be used. In addition, isoteric purine 2'deoxy-furanoside analogs, 2'-deoxynebularine or 2'deoxyxanthosine, or other purine or pyrimidine analogs may also be used. By carefully selecting the bases and base analogs, one may fine tune the hybridization properties of the oligonucleotide. For example, inosine may be used to reduce hybridization specificity, while diaminopurines may be used to increase hybridization specificity.

Adenine and guanine may be modified at positions N3, N7, N9, C2, C4, C5, C6, or C8 and still maintain their hydrogen bonding abilities. Cytosine, thymine and uracil may be modified at positions N1, C2, C4, C5, or C6 and still maintain their hydrogen bonding abilities. Some base analogs have different hydrogen bonding attributes than the naturally occurring bases. For example, 2-amino-2'-dA forms three (3), instead of the usual two (2), hydrogen bonds to thymine (T). Examples of base analogs that have been shown to increase duplex stability include, but are not limited to, 5-fluoro-2'-dU, 5-bromo-2'-dU, 5-methyl-2'-dC, 5-propynyl-2'-dC, 5-propynyl-2'-dU, 2-amino-2'-dA, 7-deazaguanosine, 7-deazadenosine, and N2-Imidazoylpropyl-2'-dG.

Nucleotide analogs may be created by modifying and/or replacing a sugar moiety. The sugar moieties of the nucleotides may also be modified by the addition of one or more substituents. For example, one or more of the sugar moieties may contain one or more of the following substituents: amino, alkylamino, araalkyl, heteroalkyl, heterocycloalkyl, aminoalkylamino, O, H, an alkyl, polyalkylamino, substituted silyl, F, Cl, Br, CN, $CF_3$, $OCF_3$, OCN, O-alkyl, S-alkyl, SOMe, $SO_2Me$, $ONO_2$, NH-alkyl, $OCH_2CH=CH_2$, $OCH_2CCH$, OCCHO, allyl, O-allyl, $NO_2$, $N_3$, and $NH_2$. For example, the 2' position of the sugar may be modified to contain one of the following groups: H, OH, OCN, O-alkyl, F, CN, $CF_3$, allyl, O-allyl, $OCF_3$, S-alkyl, SOMe, $SO_2Me$, $ONO_2$, $NO_2$, $N_3$, $NH_2$, NH-alkyl, or $OCH=CH_2$, OCCH, wherein the alkyl may be straight, branched, saturated, or unsaturated. In addition, the nucleotide may have one or more of its sugars modified and/or replaced so as to be a ribose or hexose (i.e. glucose, galactose) or have one or more anomeric sugars. The nucleotide may also have one or more L-sugars.

Representative United States patents that teach the preparation of such modified bases/nucleosides/nucleotides include, but are not limited to, U.S. Pat. Nos. 6,248,878, and 6,251,666 which are herein incorporated by reference.

The sugar may be modified to contain one or more linkers for attachment to other chemicals such as fluorescent labels. In an embodiment, the sugar is linked to one or more aminoalkyloxy linkers. In another embodiment, the sugar contains one or more alkylamino linkers. Aminoalkyloxy and alkylamino linkers may be attached to biotin, cholic acid, fluorescein, or other chemical moieties through their amino group.

Nucleotide analogs or derivatives may have pendant groups attached. Pendant groups serve a variety of purposes which include, but are not limited to, increasing cellular uptake of the oligonucleotide, enhancing degradation of the target nucleic acid, and increasing hybridization affinity. Pendant groups can be linked to any portion of the oligonucleotide but are commonly linked to the end(s) of the oligonucleotide chain. Examples of pendant groups include, but are not limited to: acridine derivatives (i.e. 2-methoxy-6-chloro-9-aminoacridine); cross-linkers such as psoralen derivatives, azidophenacyl, proflavin, and azidoproflavin; artificial endonucleases; metal complexes such as EDTA-Fe(II), o-phenanthroline-Cu(I), and porphyrin-Fe(II); alkylating moieties; nucleases such as amino-1-hexanolstaphylococcal nuclease and alkaline phosphatase; terminal transferases; abzymes; cholesteryl moieties; lipophilic carriers; peptide conjugates; long chain alcohols; phosphate esters; amino; mercapto groups; radioactive markers; nonradioactive markers such as dyes; and polylysine or other polyamines. In one example, the nucleic acid comprises an oligonucleotide conjugated to a carbohydrate, sulfated carbohydrate, or gylcan. Conjugates may be regarded as a way as to introduce a specificity into otherwise unspecific DNA binding molecules by covalently linking them to a selectively hybridizing oligonucleotide.

The catalytic nucleic acid binding domains (i.e. the non-catalytic domains) or antisense oligonucleotide may comprise modified bonds. For example internucleosides bonds of the oligonucleotide may comprise phosphorothioate linkages. The nucleic acid may comprise nucleotides having moiety may be modified by replacing one or both of the two bridging oxygen atoms of the linkage with analogues such as —NH, —CH$_2$, or —S. Other oxygen analogues known in the art may also be used. The phosphorothioate bonds may be stereo regular or stereo random.

The oligonucleotide moiety may have one or more of its sugars modified or replaced so as to be ribose, glucose, sucrose, or galactose, or any other sugar. Alternatively, the phosphorothioate oligonucleotide may have one or more of its sugars substituted or modified in its 2' position, i.e. 2' allyl or 2'-O-allyl. An example of a 2'-O-allyl sugar is a 2'-O-methylribonucleotide. Further, the phosphorothioate oligonucleotide may have one or more of its sugars substituted or modified to form an α-anomeric sugar.

A catalytic nucleic acid may include non-nucleotide substitution. The non-nucleotide substitution includes either abasic nucleotide, polyether, polyamine, polyamide, peptide, carbohydrate, lipid or polyhydrocarbon compounds. The term "abasic" or "abasic nucleotide" as used herein encompasses sugar moieties lacking a base or having other chemical groups in place of base at the 1' position.

Determining the effective amount of the instant nucleic acid molecules can be done based on animal data using routine computational methods. In one embodiment, the effective amount contains between about 10 ng and about 100 µg of the instant nucleic acid molecules per kg body mass. In another embodiment, the effective amount contains between about 100 ng and about 10 µg of the nucleic acid molecules per kg body mass. In a further embodiment, the effective amount contains between about 1 µg and about 5 µg, and in a further embodiment about 2 µg, of the nucleic acid molecules per kg body mass.

In an embodiment the second agent promotes trafficking and is a CC chemokine. In further embodiments the CC chemokine is RANTES, EOTAXIN, monocyte chemoattractant protein-1 (MCP-1), MCP-2, MCP-3, or MCP.

In an embodiment the second agent promotes trafficking and is a CXC chemokine. In further embodiments the CXC chemokine is Interleukin-8, Gro-Alpha, or Stromal-Derived Factor-1.

In an embodiment the second agent promotes mobilization of angioblasts into the subject's bloodstream.

In an embodiment the cardiac progenitor cell is resident in the heart, or that comes into the heart from elsewhere after acute ischemia, is smaller than mature cardiomyocytes, expresses alpha sarcomeric actin but is negative for troponin, is normally quiescent but can be induced to go into cell cycle as defined by positive Ki67 staining.

This invention further provides a method of improving cardiac function in a subject comprising administering to the subject an amount of an agent effective to induce proliferation of cardiomyocytes in the heart tissue in the subject so as to thereby improve cardiac function in the subject.

Cardiac function, or myocardial function, can be determined by any combination of improvement in ejection fraction, perfusion, reduction in anginal symptoms, improvement in quality of life, increased walking ability, longevity of life, reduction in heart medication, and/or prevention of heart failure, as this terms are normally understood in the art. An improvement in cardiac function in a subject is measured by determining any of these factors in a subject before and after treatment by any of the instant methods.

In one embodiment of the instant methods, the subject has suffered myocardial ischemia or myocardial infarct. In different embodiments the agent is G-CSF, GM-CSF, IL-8, a Gro family chemokine, an inhibitor of CXCR4, or an inhibitor of SDF-1. In further embodiments the inhibitor of CXCR4 is a small molecule or a monoclonal antibody, the inhibitor of CXCR4 is a small molecule and is AMD 3100, the inhibitor of SDF-1 is a small molecule or a monoclonal antibody, and the Gro family chemokine is Gro alpha. In another embodiment the inhibitor is AMD 070. In differing embodiments the inhibitor of CXCR4 is a catalytic nucleic acid, an oligonucleotide, RNAi, (RNA interference) or a small molecule.

This invention further provides a method of inducing apoptosis in a cell comprising inhibiting expression of a peroxiredoxin in the cell. In one embodiment the cell is a tumor cell. In different embodiments the peroxiredoxin is peroxiredoxin I, II, II, IV, or V. In one embodiment the inhibition of expression of peroxiredoxin is effected by contacting the cell with a catalytic nucleic acid which binds mRNA encoding peroxiredoxin, thereby inhibiting the expression thereof. In different embodiments the inhibition of expression of peroxiredoxin is effected by contacting the cell with an antisense oligonucleotide, a monoclonal antibody, RNA interference or a small molecule.

This invention further provides a method of treating a disorder of a tissue of a subject involving loss of tissue cells which comprises administering to the subject an amount of an agent effective to cause tissue cell proliferation within the tissue of the subject so as to thereby treat the disorder. In differing embodiments the tissue is cardiac tissue, brain tissue, peripheral vascular tissue, hepatic tissue, renal tissue, gastrointestinal tissue, lung tissue, smooth muscle tissue, or striated muscle tissue. In differing embodiments the agent is G-CSF, SDF-1, GM-CSF, IL-8, VEGF. In one embodiment the agent is an inhibitor of CXCR4/SDF-1 interaction. In further embodiments the inhibitor is a catalytic nucleic acid, a monoclonal antibody, a antisense oligonucleotide, a small molecule, or RNAi. In one embodiment the agent is an inducer of peroxiredoxin expression. In further embodiments the peroxiredoxin is peroxiredoxin I, II, III, IV, or V.

In any of the instant methods wherein the agent is G-CSF, the G-CSF may be a covalent conjugate of recombinant methionyl human G-CSF (Filgrastim) and monomethoxypolyethylene glycol, such as Neulasta. Filgrastim is a water-soluble 175 amino acid protein with a molecular weight of approximately 19 kilodaltons (kd). Filgrastim is obtained from the bacterial fermentation of a strain of *Escherichia coli* transformed with a genetically engineered plasmid containing the human G-CSF gene. To produce pegfilgrastim, a 20 kd monomethoxypolyethylene glycol molecule is covalently bound to the N-terminal methionyl residue of Filgrastim. The average molecular weight of pegfilgrastim is approximately 39 kd. Neulasta is supplied in 0.6 mL prefilled syringes for subcutaneous (SC) injection. Each syringe contains 6 mg pegfilgrastim (based on protein weight), in a sterile, clear, colorless, preservative-free solution (pH 4.0) containing acetate (0.35 mg), sorbitol (30.0 mg), polysorbate 20 (0.02 mg), and sodium (0.02 mg) in water for injection, USP.

This invention provides a method of treating a disorder of a tissue of a subject involving apoptosis of cells in the tissue which comprises administering to the subject an amount of an agent effective to inhibit apoptosis of cells in the tissue within the subject so as to thereby treat the disorder. In one embodiment the agent is an inhibitor of VDUP-1 expression. In further embodiments the inhibitor of VDUP-1 expression is catalytic nucleic acid, a monoclonal antibody, an antisense oligonucleotide, a small molecule, or an RNAi. In differing embodiments the tissue is cardiac tissue, cerebrovascular tissue, or cerebral tissue.

This invention also provides a method of inhibiting proliferation of fibroblasts or inflammatory cells in a tissue and thereby inhibiting collagen formation comprising contacting the tissue with an inhibitor of VDUP-1 expression. In one embodiment the inhibitor of VDUP-1 expression is a catalytic nucleic acid, a monoclonal antibody, an antisense oligonucleotide, a small molecule, or an RNAi.

In one embodiment the subject of any of the above methods is a mammal and in a preferred further embodiment the mammal is a human being. In one embodiment the subject has a cardiovascular disease. In further embodiments the subject has congestive heart failure, has suffered a myocardial infarct, has suffered myocardial ischemia, has angina, or has a cardiomyopathy.

This invention will be better understood by reference to the Experimental Details which follow, but those skilled in the art will readily appreciate that the specific experiments detailed are only illustrative of the invention as described more fully in the claims which follow thereafter.

Experimental Results (I)

CXC Chemokines Regulate Endothelial Progenitor Cell Migration to the Heart.

Figure 1B:
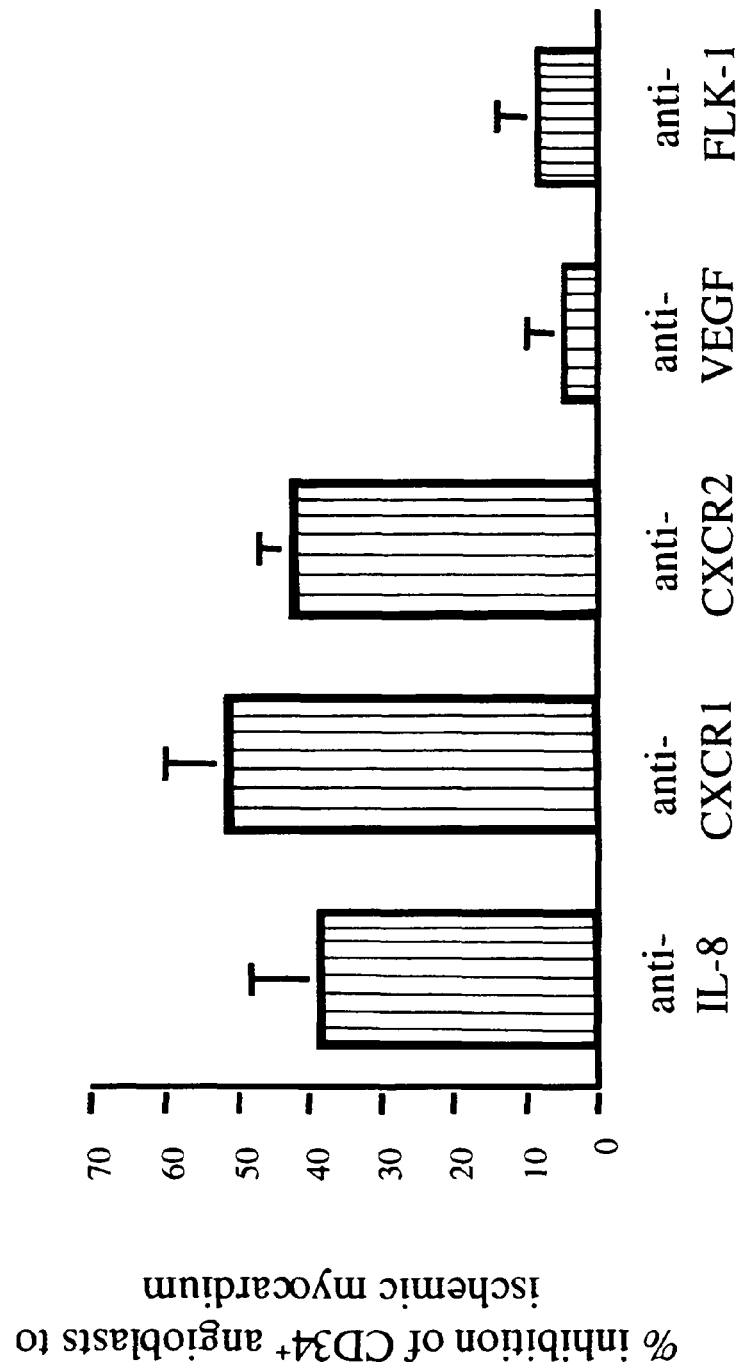
Figure 1C:
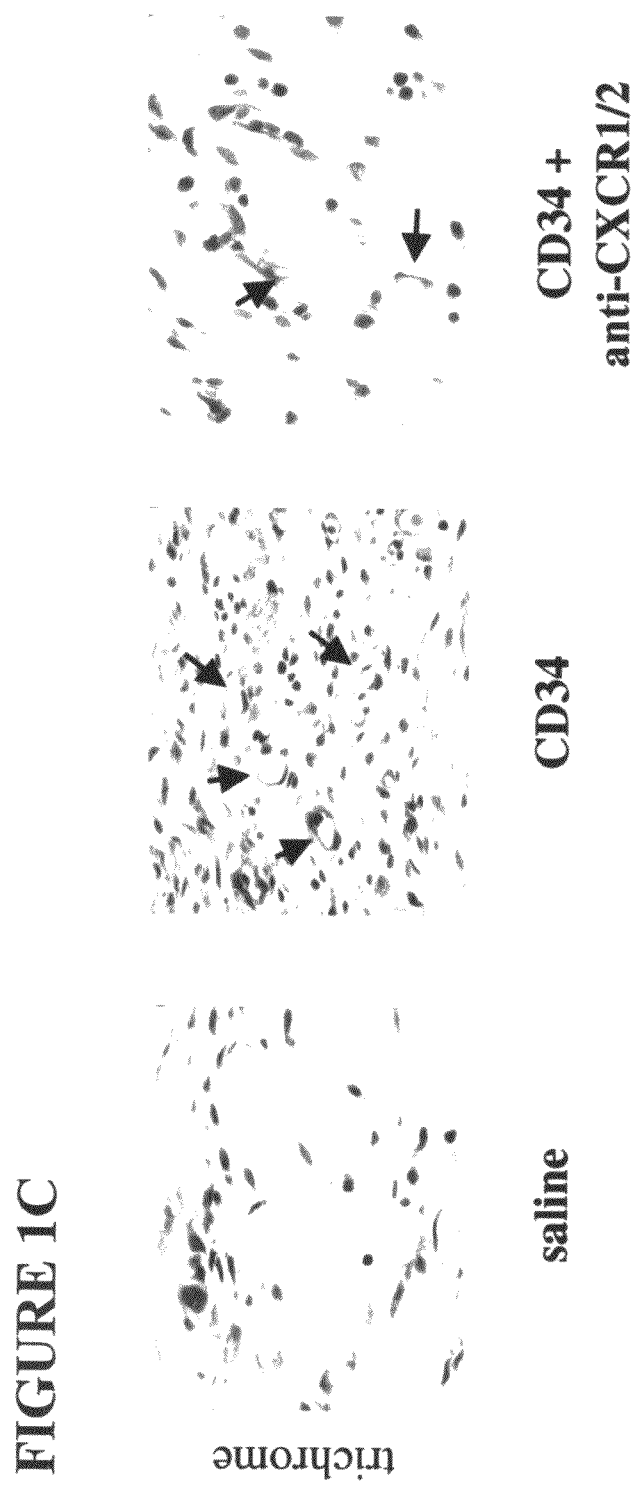
Figure 1D:
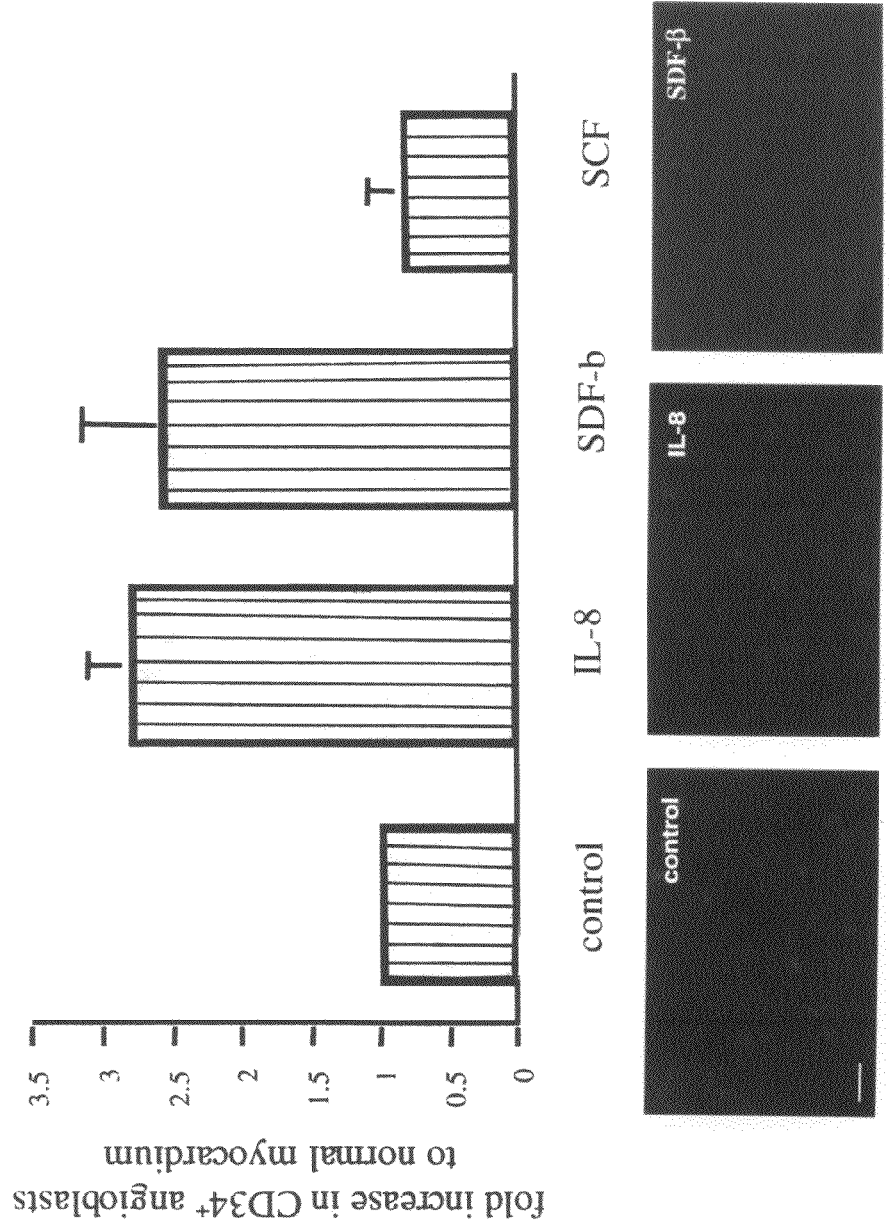

We investigated the in vivo role of CXC receptor-ligand interactions in mediating chemotaxis of human Endothelial progenitor cell to ischemic tissue and subsequent induction of vasculogenesis, using myocardial infarction in the LAD-ligated nude rat model. As shown in FIG. 1$a$, DiI-labelled human CD34+ cells obtained by G-CSF mobilization (>98% CD34 purity, containing 6-12% CD117$^{bright}$ endothelial progenitor cells) were selectively detected in infarcted myocardium after intravenous injection, but not in myocardium from sham-operated rats. Co-administration of blocking mAbs against rat Cinc (the rat homologue of human IL-8 and Gro-alpha), or against the human surface receptors for these pro-angiogenic chemokines, CXCR1 or CXCR2, reduced myocardial trafficking of human bone marrow-derived CD34+ cells at 48 hours by 40-60% relative to control antibodies ($p<0.01$), FIG. 1$b$. By two weeks, rats receiving human CD34+ cells demonstrated significantly increased infarct bed microvascularity in comparison to rats receiving saline, FIG. 1$c$, and this was reduced by 50% when anti-CXCR1/2 mAbs were co-administered. Since we have previously shown that the vasculogenic properties of CD34+ cells are abolished after depletion of the minor CD117$^{bright}$ angioblast fraction (7), these results indicate that by regulating angioblast migration to ischemic tissues CXC chemokines influence the development of vasculogenesis at these sites. In contrast, although direct intracardiac injection of IL-8 or SDF-1 at 1.0 µg/ml into non-infarcted hearts resulted in 2.3 and 2.5-fold increases in myocardial infiltration by human CD34+ cells at 48 hours (both $p<0.01$), FIG. 1$d$, no vasculogenesis was observed at two weeks under these conditions. Together, these results indicate that following chemokine-induced migration to the infarct zone, differentiation of endothelial progenitor cell to mature endothelial cells and induction of vasculogenesis require additional factors, as yet undefined, which are produced under ischemic conditions.

Inhibiting CXCR4/SDF-1 Interactions Redirects Endothelial Progenitor Cells to the Heart.

Although LAD coronary artery ligation resulted in trafficking of intravenously injected human endothelial progenitor cells to the site of ischemic myocardium, it was also accompanied by increased distribution of human cells to rat bone marrow. As shown in FIG. 2$a$, at 2-14 days after intravenous injection of 2×10$^6$ human CD34+ cells bone marrow from LAD-ligated rats contained 5-8 fold higher levels of human CD117$^{bright}$ endothelial progenitor cells compared with bone marrow from normal rats, $p<0.001$. This was presumably due to the proliferative effects of factors in ischemic serum since we have previously shown that culture for 2 days with ischemic serum increases proliferation of CD34+ CD117$^{bright}$ human endothelial progenitor cells by 4-5 fold (7). Because the migration of actively cycling CD34+ cells to bone marrow is promoted by SDF-1 produced constitutively by marrow stromal cells (31), we investigated whether the distribution of human CD34+CD117$^{bright}$ endothelial progenitor cells to ischemic rat bone marrow involved SDF-1/CXCR4 interactions. As shown in FIG. 2$b$, co-administration of mAbs against either human CXCR4 or rat SDF-1 significantly inhibited migration of intravenously administered human endothelial progenitor cells to ischemic rat bone marrow compared with anti-CD34 control antibody (both $p<0.001$). Moreover, co-administration of mAbs against either human CXCR4 or rat SDF-1 increased trafficking of CD34+ human endothelial progenitor cells to ischemic rat myocardium by means of 24% and 17%, respectively (both $p<0.001$), FIG. 2$c$.

Capillary Lumen Size is Dependent on Absolute Angioblast Numbers.

We next examined the relationship between angioblast number, myocardial neovascularization, and protection against myocyte apoptosis. Two days following LAD ligation animals were intravenously injected with G-CSF mobilized CD34+ human cells reconstituted with varying proportions of CD117$^{bright}$ endothelial progenitor cells (10$^3$, 10$^5$, 10$^5$ plus anti-CXCR4 mAb, 2×10$^5$, and 2×10$^5$ plus anti-CXCR4 mAb). Similar numbers of DiI-labelled human cells were detected in the infarct zone 48 hours after injecting each cellular population, data not shown. Induction of neovascularization at two weeks was measured by performing quantitative analysis of medium- and large-sized capillaries, defined, respectively, as having 3-6 or >6 contiguous endothelial lining cells. Medium-sized capillaries had mean lumen diameter of 0.020 mm+0.002, while large-sized capillaries had mean lumen diameter of 0.053 mm+0.004 ($p<0.001$). Notably, large-lumen capillaries overlapped in size with arterioles which could be distinguished by a thin layer containing 2-3 smooth muscle cells of rat origin, as determined by positive staining with desmin and rat MHC class I mAbs. As shown in FIGS. 3$a$-$c$, both the group receiving 2×10$^5$ endothelial progenitor cells and the one receiving 10$^5$ endothelial progenitor cells plus anti-CXCR4 mAb demonstrated 1.7-fold higher numbers of medium-sized capillaries compared with the other two groups ($p<0.01$). The group receiving 2×10$^5$ endothelial progenitor cells additionally demonstrated 3.3-fold higher numbers of large-lumen capillaries compared with the groups receiving 10$^3$ or 10$^5$ endothelial progenitor cells ($p<0.01$), and 2-fold higher numbers of large-lumen capillaries compared with the group receiving 10$^5$ endothelial progenitor cells plus anti-CXCR4 mAb ($p<0.01$). As shown in FIG. 3$d$, co-administration of anti-CXCR4 mAb together with the highest concentration of endothelial progenitor cells, 2×10$^5$, resulted in a further 23% increase in growth of large-lumen capillaries. More strikingly, there was a further 2-fold increase in capillary numbers when 2×10$^5$ endothelial progenitor cells were injected intravenously after direct intracardiac delivery of 1.0 µg/ml SDF-1 into infarcted hearts ($p<0.01$). Since no similar increase in peri-infarct capillary numbers was seen after intracardiac delivery of IL-8, we interpret these results to indicate that the endogenous IL-8 concentrations in ischemic rat hearts were sufficient to saturate angioblast CXCR1/2 receptors in vivo, whereas intracardiac injection of SDF-1 resulted in a shift in the balance of SDF-1 expression between bone marrow and heart, and consequently resulted in redirected angioblast trafficking to the ischemic heart.

As shown in FIG. 3$e$, the number of apoptotic cardiomyocytes at the infarct rim was significantly reduced in both rats receiving 10$^5$ endothelial progenitor cells plus anti-CXCR4 mAb and those receiving $2 \times 10^5$ endothelial progenitor cells compared with the groups receiving either $10^3$ or $10^5$ endothelial progenitor cells alone (both p<0.001). Moreover, co-administration of anti-CXCR4 mAb or intracardiac injection of SDF-1 resulted in further reductions in cardiomyocyte apoptosis of 65% and 76%, respectively, FIG. 3f (both p<0.001). Together, these data indicate that post-infarct cardioprotection against myocyte apoptosis is dependent on myocardial neovascularization induced by a critical number of intravenously injected endothelial progenitor cells. This threshold can apparently be lowered by strategies that prevent endothelial progenitor cell redistribution to the bone marrow, such as interrupting CXCR4/SDF-1 interactions, or enhanced SDF-1 expression in the ischemic myocardium.

Capillary Lumen Size as Determinant of Improvement in Cardiac Function.

Figure 4A:
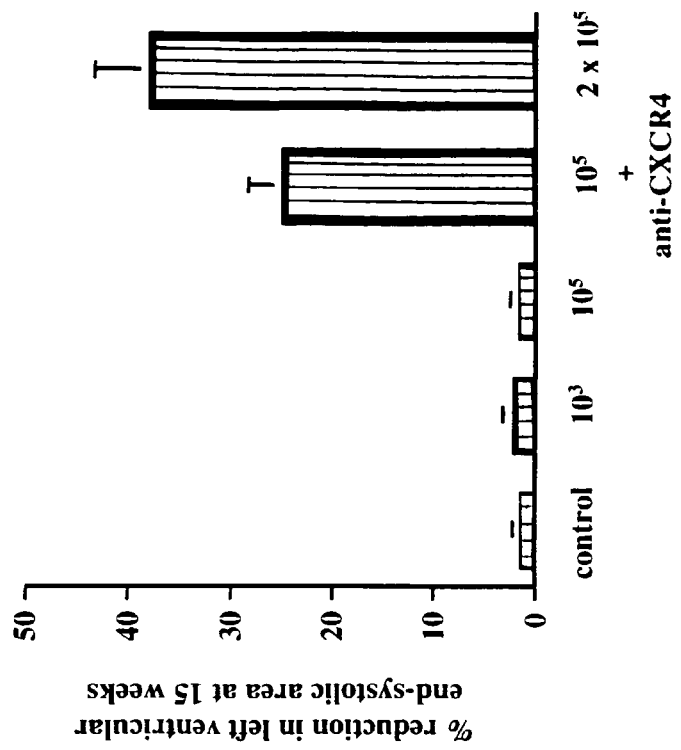
Figure 4B:
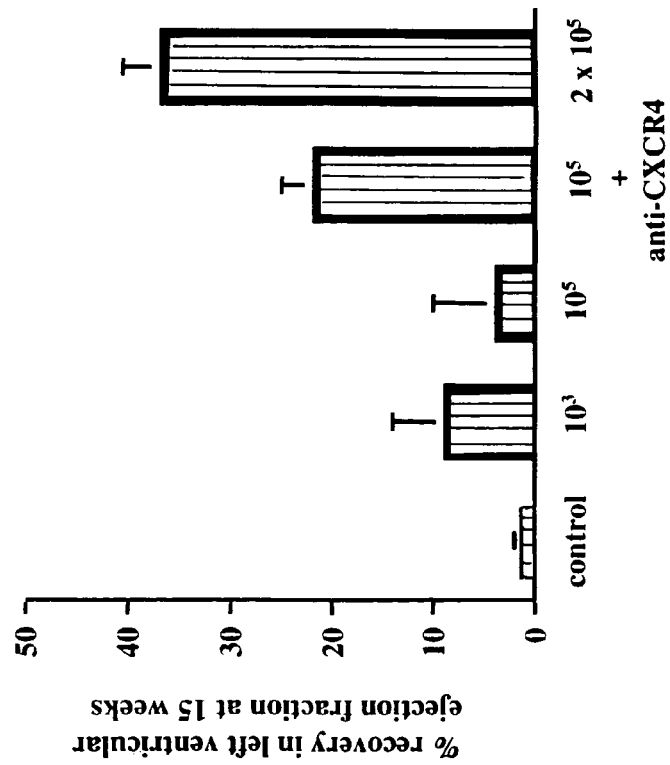

We next examined the effect of increasing the number of human endothelial progenitor cells trafficking to ischemic myocardium on long-term myocardial function, defined as the degree of improvement in left ventricular ejection fraction (LVEF) and reduction in left ventricular end-systolic area (LVAs) at 15 weeks after intravenous injection, FIGS. 4a and b. No improvement in these parameters was observed in the groups receiving $10^3$ or $10^5$ endothelial progenitor cells in comparison to rats receiving saline alone. In contrast, rats receiving $10^5$ endothelial progenitor cells plus anti-CXCR4 mAb demonstrated significant improvement in these parameters, 22+2% mean recovery in LVEF and 24+4% mean reduction in LVAs (both p<0.001). Even more strikingly, the group receiving $2 \times 10^5$ endothelial progenitor cells had a mean recovery in LVEF of 34+4% and a mean reduction in LVAs of 37+6% (both p<0.001), or 50% further improvement in both parameters. These results were very surprising to us since both groups of animals had demonstrated the same degree of neovascularization involving medium-sized capillaries at two weeks together with similar levels of protection against early apoptosis of cardiomyocytes. This suggested that the additional functional long-term improvement in rats receiving $2 \times 10^5$ human endothelial progenitor cells was related to the early development of large-sized capillaries and was mediated through a different mechanism than protection against myocyte apoptosis.

Large Capillaries Induce Sustained Regeneration of Endogenous Myocytes.

Figure 4D:
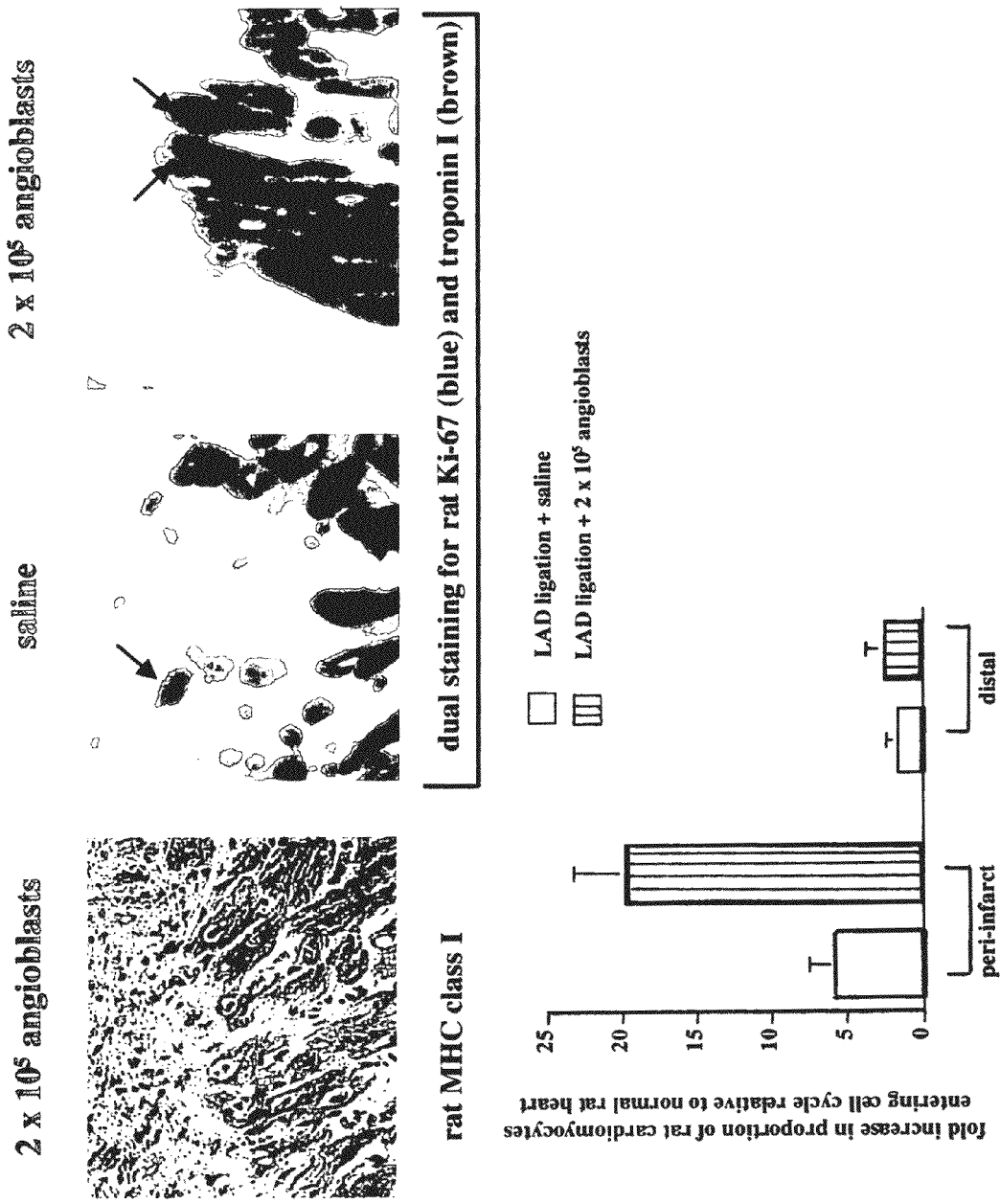

Although myocyte hypertrophy and increase in nuclear ploidy have generally been considered the primary mammalian cardiac responses to ischemia, damage, and overload (1,2) recent observations have suggested that human cardiomyocytes have the capacity to proliferate and regenerate in response to injury (18,19). Therefore, we investigated whether the additive improvement in cardiac function observed after injection of $2 \times 10^5$ human endothelial progenitor cells involved induction of cardiomyocyte proliferation and/or regeneration. At two weeks after LAD ligation rats receiving $2 \times 10^5$ human endothelial progenitor cells demonstrated numerous "fingers" of cardiomyocytes of rat origin, as determined by expression of rat MHC class I molecules, extending from the peri-infarct region into the infarct zone. Similar extensions were seen less frequently in animals receiving $10^3$ and $10^5$ endothelial progenitor cells, and very rarely in those receiving saline. As shown in FIG. 4c, the islands of cardiomyocytes at the peri-infarct rim in animals receiving $2 \times 10^5$ human endothelial progenitor cells contained a high frequency of rat myocytes with DNA activity, as determined by dual staining with mAbs reactive against cardiomyocyte-specific troponin I and rat Ki-67. In contrast, in animals receiving saline there was a high frequency of cells with fibroblast morphology and reactivity with rat Ki-67, but not troponin I, within the infarct zone. The number of cardiomyocytes progressing through cell cycle at the peri-infarct region of rats receiving $2 \times 10^5$ human endothelial progenitor cells was 40-fold higher than that at sites distal to the infarct, where myocyte DNA activity was no different than in sham-operated rats. As shown in FIG. 4d, animals receiving $2 \times 10^5$ human endothelial progenitor cells had a 20-fold higher number of cell-cycling cardiomyocytes at the peri-infarct rim than that found in non-infarcted hearts (1.19+0.2% vs 0.06+0.03%, p<0.01) and 3.5-fold higher than in the same region in LAD-ligated controls receiving saline (1.19+0.2% vs 0.344+0.1%, p<0.01). When $2 \times 10^5$ human endothelial progenitor cells were intravenously injected after direct intracardiac delivery of 1.0 μg/ml SDF-1 into infarcted hearts, the number of cell-cycling cardiomyocytes at the peri-infarct rim was increased by a further 1.9-fold compared with intravenous injection of $2 \times 10^5$ human endothelial progenitor cells alone (FIG. 4e, p<0.01). Thus, intracardiac injection of SDF-1 in combination with intravenous injection of $2 \times 10^5$ human endothelial progenitor cells resulted in approximately an 8-fold cumulative increase in cell-cycling cardiomyocytes at two weeks compared with LAD-ligated controls receiving saline, and translated into over 4-fold greater LVEF improvement, determined by echocardiography, compared with intravenous injection of $2 \times 10^5$ endothelial progenitor cells alone (FIG. 4f, p<0.01). Co-administration of anti-CXCR4 mAb augmented LVEF improvement by 2.8-fold (p<0.01) while intracardiac injection of IL-8 conferred no additive benefit.

Figure 4G:
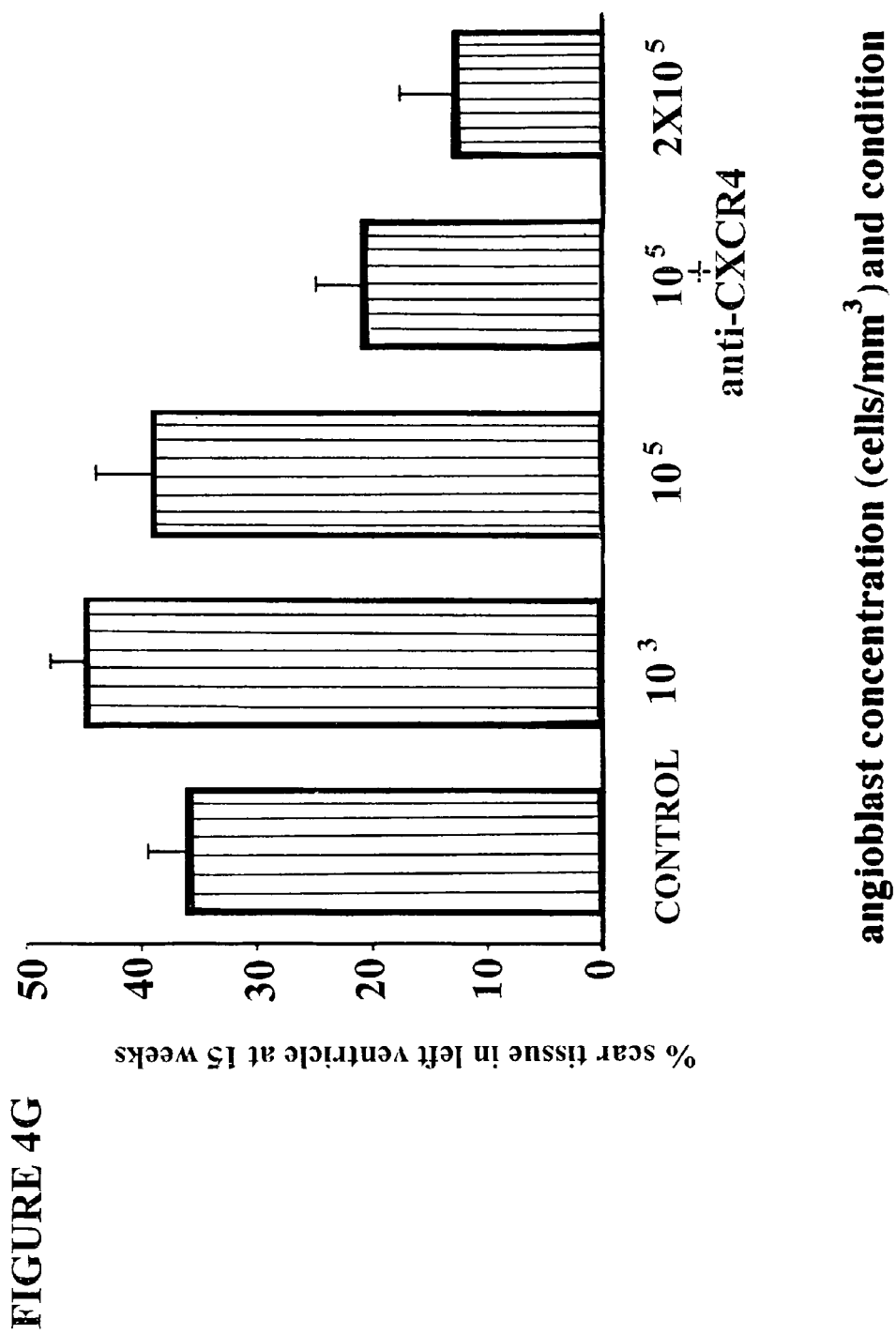
Figure 4H:
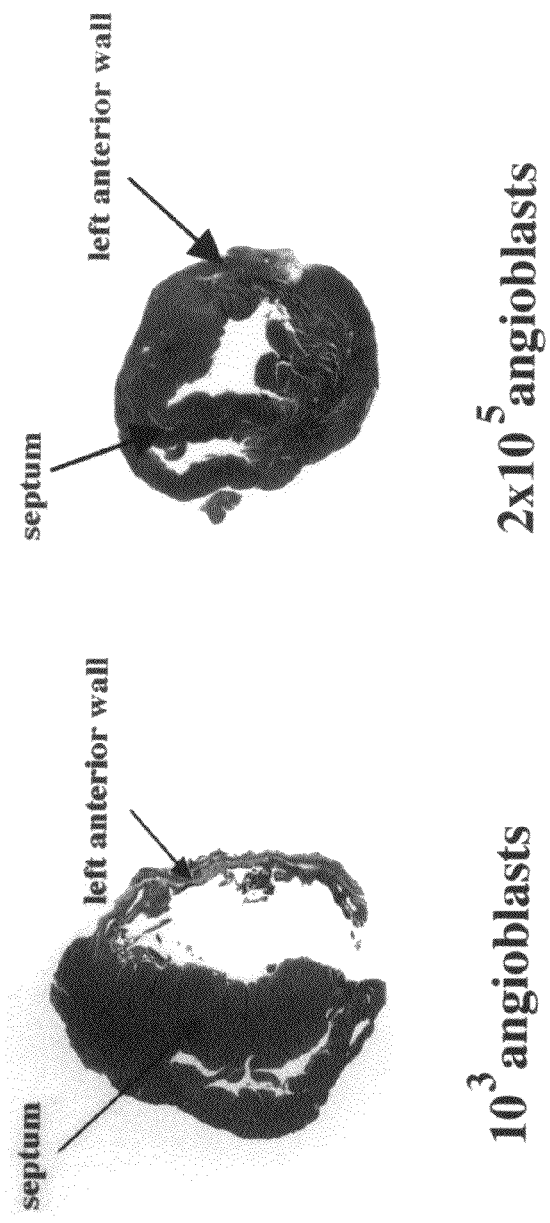

Quantitation of the ratio of fibrous tissue to myocytes at 15 weeks demonstrated significantly reduced proportions of scar/normal left ventricular myocardium in both the group receiving $2 \times 10^5$ endothelial progenitor cells and the one receiving $10^5$ endothelial progenitor cells plus anti-CXCR4 mAb, respectively 13% and 21% compared with 37-46% for each of the other groups (p<0.01), FIG. 4g. Since both groups had nearly identical levels of protection against early cardiomyocyte apoptosis, we infer that the additional 38% reduction in scar/myocyte ratio seen in the group injected with $2 \times 10^5$ endothelial progenitor cells actually reflects proliferation/regeneration of endogenous rat cardiomyocytes induced by nutrient supply from large-vessel neovascularization. This presumably accounts for the increase in functional improvement seen in this group. We conclude that the ratio of scar size to left ventricular muscle mass reflects, in part, positive effects imparted by the ability of the residual myocardium to proliferate and regenerate, in addition to negative effects of the initial infarct size and positive effects of anti-apoptotic, cardioprotective mechanisms. The overall effects of medium- and large-size neovasculature combining to both protect against myocyte apoptosis and induce myocyte proliferation/regeneration are shown dramatically in FIG. 4h where, in contrast to saline controls, injection with $2 \times 10^5$ endothelial progenitor cells resulted in almost complete salvage of the anterior myocardium, normal septal size and minimal collagen deposition.

Effecting Regeneration

PAI-1-Inhibiting Catalytic Nucleic Acid Augments Human Angioblast-Dependent Cardiomyocyte Regeneration.

We investigated whether possible neovascularization induced by a catalytic nucleic acid (designated E2) capable of inhibiting expression of PAI-1 was associated with cardiomyocyte regeneration. Injection of E2 alone did not induce cardiomyocyte regeneration despite the increase in neovascularization. Combining E2 injection with intravenously delivered human endothelial progenitor cells strikingly increased the degree of cardiomyocyte regeneration, to levels 7.5-fold higher than in saline controls (p<0.01). A scrambled DNA control enzyme (E0) had no such effect. Moreover, whereas E2 alone did not improve myocardial function, as determined by recovery in left ventricular ejection fraction at two weeks combining E2 with human endothelial progenitor cells resulted in almost doubling of the positive effect of endothelial progenitor cells alone on cardiac functional recovery. These results emphasize the importance of cardiomyocyte regeneration as the primary mechanism by which cardiac function is improved after infarction. Since combining E2 with human endothelial progenitor cells resulted in 62% greater numbers of large capillaries at the peri-infarct rim than use of either approach alone, these results indicate that angioblast-induced cardiomyocyte regeneration and improvement in cardiac function can be optimized by use of synergistic approaches, such as strategies that inhibit PAI-1 expression, which augment neovascularization either directly or through angioblast-dependent processes.

We further discovered that intravenous injection of human CD34+CD117bright angioblasts resulted in a four-fold increase in proliferation/regeneration of rat cardiomyocytes at the peri-infarct region relative to saline controls, as determined by dual staining for troponin and Ki67 (p<0.01). Combining E2 injection with intravenously delivered human angioblasts strikingly increased the degree of cardiomyocyte regeneration, to levels 7.5-fold higher than in saline controls (p<0.01). The scrambled DNA enzyme E0 had no such effect.

Gene Effects on Myocyte Proliferation

We hypothesized that myocardial neovascularization induces the signals required to elicit myocyte proliferation, and therapeutic intervention mimicking this could have striking implications for repair and regeneration of hearts damaged by episodes of ischemia or other insults.

To begin approaching this complex problem, we have employed the technique of cDNA Subtractive Hybridization. This technique enables comparison of the pattern of gene expression between two different sets of conditions. Our initial approach was to compare which genes are differentially expressed between hearts from normal rats and rats who have undergone left anterior descending (LAD) coronary artery ligation 48 hours earlier. We hypothesized that whatever the altered pattern of gene over- or underexpression after 48 hours of ischemia, neovascularization would result in a reversal in the pattern towards that seen in the non-ischemic rat heart.

Using cDNA subtractive hybridization we observed a striking reciprocal change in expression of a group of genes whose function is linked through their regulation of cellular apoptosis and cell cycle progression following oxidative stress and other inducers of DNA damage. Whereas expression of certain antioxidant genes such as superoxide dismutase was upregulated in ischemic tissue, the antioxidant stress responsive genes induced by hemin, notably heme binding protein 23 (HBP23) and glutathione-S-transferase, were downregulated. Moreover, a recently-identified protein, Vitamin D3 Up-Regulated Protein1 (VDUP1), whose mRNA expression is induced by hydrogen peroxide ($H_2O_2$) following oxidative stress and whose function counterbalances that of HBP23, was upregulated in ischemic hearts. These findings are particularly striking when considered in the context of previous observations that the presence of deficits in antioxidants and increased oxidative stress accompanying myocardial infarction appear to be directly implicated in the pathogenesis of post-infarct heart failure (74,75).

As shown in FIG. 5, using RT-PCR, the reciprocal changes in mRNA expression of HBP23 and VDUP1 in ischemic vs normal rat hearts were confirmed. Moreover, mRNA expression of these two genes returned to normal in rat tissue two weeks after intravenous injection of human adult bone marrow-derived progenitors and infarct zone neovascularization. In contrast, in LAD-ligated rat hearts receiving saline, no change in mRNA expression of these genes was observed at two weeks in comparison to the pattern observed at 48 hours. To comprehend the relationship between the effects of neovascularization on these altered expression patterns of HBP23 and VDUP1 following ischemia, and the observed protection against cardiomyocyte apoptosis together with induction of cardiomyocyte proliferation/regeneration, it is important to understand in detail the molecular effects of the products encoded by these genes on cellular apoptosis and cell cycle progression.

When cells proliferate, the mitotic cycle progression is tightly regulated by an intricate network of positive and negative signals. Progress from one phase of the cell cycle to the next is controlled by the transduction of mitogenic signals to cyclically expressed proteins known as cyclins and subsequent activation or inactivation of several members of a conserved family of serine/threonine protein kinases known as the cyclin-dependent kinases (cdks) (67). Growth arrest observed with such diverse processes as DNA damage, terminal differentiation, and replicative senescence is due to negative regulation of cell cycle progression by two functionally distinct families of Cdk inhibitors, the Ink4 and Cip/Kip families (64). The cell cycle inhibitory activity of p21Cip1/WAF1 is intimately correlated with its nuclear localization and participation in quaternary complexes of cell cycle regulators by binding to G1 cyclin-CDK through its N-terminal domain and to proliferating cell nuclear antigen (PCNA) through its C-terminal domain (68-71). The latter interaction blocks the ability of PCNA to activate DNA polymerase, the principal replicative DNA polymerase (72). For a growth-arrested cell to subsequently enter an apoptotic pathway requires signals provided by specific apoptotic stimuli in concert with cell-cycle regulators. For example, caspase-mediated cleavage of p21, together with upregulation of cyclin A-associated cdk2 activity, have been shown to be critical steps for induction of cellular apoptosis by either deprivation of growth factors (73) or hypoxia of cardiomyocytes (74).

The apoptosis signal-regulating kinase 1 (ASK1) is a pivotal component in the mechanism of cytokine- and stress-induced apoptosis (75,76). Under basal conditions, resistance to ASK1-mediated apoptosis appears to be the result of complex formation between ASK1, cytoplasmic p21Cip1/WAF1 (77), and the thiol reductase thioredoxin (TRX) (78). Intact cytoplasmic expression of p21Cip1/WAF1 appears to be important for both prevention of apoptosis in response to ASK1 (75) and in maintaining a state of terminal differentiation (77). Moreover, the reduced form of TRX, but not the oxidized form, binds to the N-terminal portion of ASK1 and is a physiologic inhibitor of ASK1-mediated cellular apoptosis (78). The recently-identified protein VDUP1 has been shown to compete with ASK1 for binding of the reduced form of TRX (78,79), resulting in augmention of ASK1-mediated apoptosis (80). This indicates that ASK1-mediated cellular apoptosis is increased by processes that result in a net dissociation of TRX from ASK1, such as either generation of TRX-VDUP1 complexes or generation of oxidised TRX by changes in cellular redox status accompanying oxidative stress.

TRX and glutathione constitute the major cellular reducing systems that maintain the thiol-disulfide status of the cytosol (81). The redox-active/dithiol active site of TRX is highly conserved across all species, Trp-Cys-Gly-Pro-Cys-Lys. The two cysteine residues at the active site, Cys-32 and Cys-35, undergo reversible oxidation-reduction reactions catalyzed by a NADPH-dependent enzyme TRX reductase. These reactions involve electron transfer via disulfide bridges formed with members of a family of antioxidant enzymes known as peroxiredoxins (Prxs), which show peroxidase activity (82, 83). Prxs are distinct from other peroxidases in that they have no cofactors, such as metals or prosthetic groups. Prxs generally have two conserved cysteines at the N- and C-terminal regions (84), and their antioxidant effects are coupled with the physiological electron donor activity of the TRX system (82, 85, 86). Prxs with 95-97% sequence homology have been identified in rats (Heme-binding protein 23, HBP23) (87), mice (mouse macrophage stress protein 23, MSP23) (88) and humans (proliferation-associated gene product, PAG (89) and human natural killer cell-enhancing factor A (90)).

Prxs are members of a repertoire of oxidative stress responsive genes whose expression is regulated by NF-E2-related factor 2 (Nrf2) which binds to an anti-oxidant responsive element (ARE) present in the promoter of each (91). These include glutathione-S-transferase, heme oxygenase-1, and TRX. Under basal conditions, Nrf2 is bound to a specific protein, Keap1, in the cytosol (92). However, under conditions of oxidative stress Nrf2 dissociates from Keap1 and translocates to the nucleus where it induces transcriptional activation of the anti-oxidant genes containing ARE motifs. Although the precise extracellular signalling pathways have not been elucidated, nuclear translocation of Nrf2 and subsequent ARE activation appear to be dependent on pathways activated by phosphatidylinositol 3-kinase (PI3 kinase) (93). In addition, hemin is a potent inducer of Nrf2 dissociation from Keap1, resulting in TRX gene transcription through the ARE (94).

During periods of rapid changes in cellular redox Prxs presumably serve to maintain the cytosolic levels of reduced TRX by accepting electrons from the oxidized form of TRX. This homeostatic mechanism likely enables maintenance of sufficient levels of reduced TRX to ensure adequate binding to ASK1 and prevention of cellular apoptosis. If the endogenous Prx system is overloaded, as might occur during changes in cellular redox when excess oxidized TRX is generated, cellular apoptosis will occur through the unopposed effects of ASK1. To counteract this, transcriptional activation of Prxs must occur following oxidative stress via nuclear translocation of Nrf2. This can be achieved either by Nrf2 dissociation from Keap1 via hemin- and PI3 kinase-dependent mechanisms (93,94), or by increasing Nrf2 mRNA and protein expression as occurs following increase in oxygen tension (95,96).

In addition to directly interacting with TRX, the Prx gene products (PAG, HBP23, MSP23, NKEF, etc) specifically bind the SH3 domain of c-Abl, a non-receptor tyrosine kinase, inhibiting its activation by various stimuli, including agents that damage DNA (97). c-Abl activation through the SH3 domain induces either arrest of the cell cycle in phase G1 or cellular apoptosis (98). Cell cycle arrest is dependent on the kinase activity of c-Abl (96) and is mediated by the ability of c-Abl to downregulate the activity of the cyclin-dependent kinase Cdk2 and induce the expression of p21 (99). The apoptotic effects of c-Abl are dependent on the ability of nuclear c-Abl to phosphorylate p73, a member of the p53 family of tumor-suppressor proteins which can induce apoptosis (100,101). Recently, it has been shown that cytoplasmic, rather than nuclear, forms of c-Abl are activated by $H_2O_2$ and that this results in mitochondrial localization of c-Abl, c-Abl dependent cytochrome c release, and cellular apoptosis following oxidative stress (102,103). By associating with c-Abl in vivo, the PAG gene product (and presumably the other Prxs) can inhibit tyrosine phosphorylation induced by c-Abl overexpression and rescue cells from both the cytostatic and pro-apoptotic effects of the activated c-Abl gene product (97).

Our finding that Nrf2-dependent oxidative stress responsive genes are downregulated following myocardial ischemia likely reflects direct effects of hemin and oxygen deprivation. The end result of Prx downregulation in the ischemic heart would be augmentation in ASK1-dependent cellular apoptosis as well as Abl-dependent apoptosis and cell cycle arrest. The observed parallel increase in VDUP1 expression would further augment ASK1-dependent cellular apoptosis. Thus, the ratio in expression of PAG or other Prx mRNA or protein to VDUP1 mRNA or protein can form the basis of a diagnostic assay to predict the degree of risk for cardiomyocyte apoptosis and cell cycle arrest after ischemia, as well as enable monitoring of the response to specific therapy after myocardial ischemia that protects cardiomyocytes against apototic death and enhances myocardial proliferation/regeneration.

Reversing the reduced expression of the Prxs following myocardial ischemia would increase Prxs in the heart in order to protect the ischemic myocardium against apoptosis through both c-Abl inhibition and reduction of oxidised TRX, and to enable cardiomyocyte proliferation/regeneration by inhibiting the effects of c-Abl on cell cycle progression from G1 to S phase.

Increasing Nrf2 mRNA or causing dissociation of Nrf2 protein from Keap1, or preferably cause both to occur simultaneously, in the setting of myocardial ischemia in order to increase transcription and activity of members of a repertoire of oxidative stress responsive genes whose expression is regulated by binding of Nrf2 to an anti-oxidant responsive element (ARE) in their promoters, including the Prxs, TRX and glutathione-S-transferase would result in both protection of cardiomyocytes against apoptosis as well as induce cardiomyocyte cell cycle progression following oxidative stress.

Reducing the expression of VDUP1 following myocardial ischemia would protect the ischemic myocardium against apoptosis by reducing binding of TRX to VDUP1, and consequently increasing TRX-ASK1 interactions.

Neovascularization of the myocardium, by either bone marrow-derived endothelial progenitors or any other process, is an example of one method which causes induction of Prx expression and reduction in VDUP1 expression after myocardial ischemia, and results in both protection against redox-mediated apoptosis and induction of myocardial proliferation/regeneration.

Small molecules which specifically inhibit binding of Nrf2 to Keap1 would be expected to have similar protective effects against cardiomyocyte apoptosis and to induce myocardial proliferation/regeneration after ischemia. Similarly, small molecules that specifically inhibit binding of TRX to VDUP1, would be expected to have similar protective effects against cardiomyocyte apoptosis after ischemia.

Use of small molecules to specifically inhibit c-Abl tyrosine kinase activation after myocardial ischemia would be expected to have similar protective effects against cardiomyocyte apoptosis and to induce myocardial proliferation/regeneration after ischemia. A specific example of a small molecule to inhibit c-Abl tyrosine kinase activation is STI-571. Use of this or related molecules after myocardial infarction would protect against cardiomyocyte apoptosis and induce myocardial proliferation/regeneration.

DNA Enzyme Specific for VDUP-1 Cleaves Synthetic Rat VDUP-1 Oligonucleotide

By subtractive hybridization, we found that mRNA expression of the protein VDUP1 is significantly increased in the heart after acute ischemia. VDUP1 has been shown to bind the cytosolic protein thioredoxin, TRX, which functions to maintain the thiol-disulfide status of the cytosol. By binding to reduced forms of TRX, VDUP1 prevents the ability of reduced TRX to undergo reversible oxidation-reduction reactions catalyzed by a NADPH-dependent enzyme, TRX reductase. This results in cellular apoptosis due to excessive cytosolic and mitochondrial production of oxygen radicals.

VDUP1 competes for TRX binding with another cytosolic protein that is normally bound to reduced TRX, the apoptosis signal-regulating kinase 1 (ASK1). ASK-1 is a pivotal component in the mechanism of cytokine- and stress-induced apoptosis. Its activation results in excessive phosphorylation and activation of p38 MAP kinase, a principal mediator of cellular apoptosis. The reduced form of TRX, but not the oxidised form, binds to the N-terminal portion of ASK1 and is a physiologic inhibitor of ASK1-mediated cellular apoptosis. Binding of VDUP1 to TRX results in a net dissociation of ASK1 from TRX, potentially resulting in augmentation of ASK1-mediated apoptosis via p38 MAP kinase-dependent pathways.

With respect to cardiac overexpression of VDUP1, the anticipated effects would be those due to excessive p38 MAP kinase activation and oxidative redox damage, including cardiomyocyte apoptosis, fibroblast proliferation, collagen secretion and scar formation. Similar effects would be expected to be the consequence of VDUP1 overexpression in other tissues undergoing acute or chronic ischemic injury, for example the brain following cerebrovascular ischemia/stroke.

We have developed a DNA enzyme targeting the VDUP1 mRNA. The DNA enzyme, once delivered to the ischemic myocardium (or other ischemic tissues such as the brain) can inhibit local VDUP1 mRNA and protein expression, thus reducing p38 MAP kinase activation and oxidative damage.

As shown in FIG. 12, at enzyme concentrations ranging from 0.05 uM to 5 uM the sequence-specific VDUP1 DNA enzyme cleaved a synthetic rat VDUP1 oligonucleotide in a concentration- and time-dependent manner.

Figure 13B:
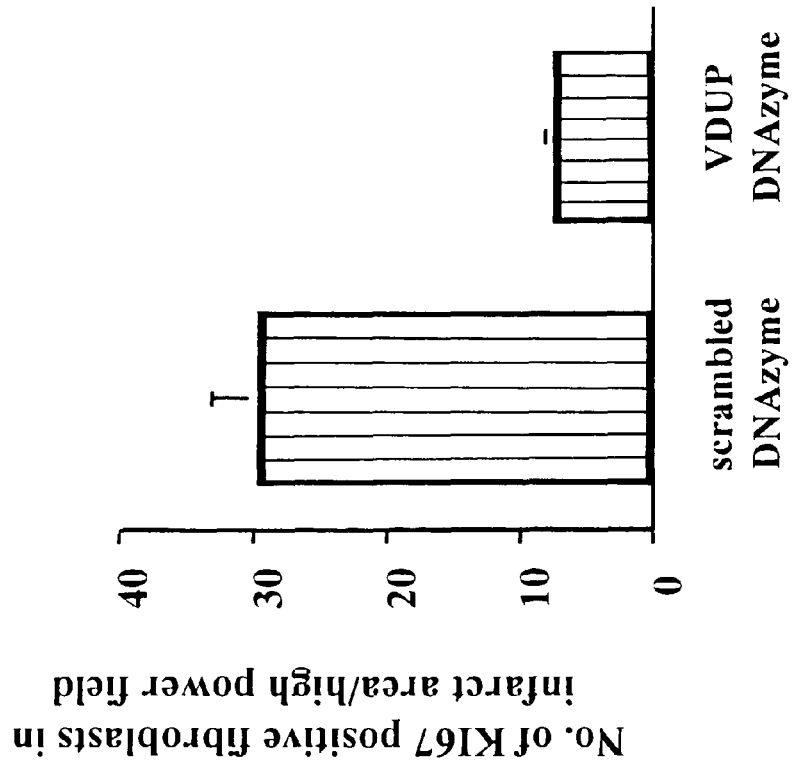
Figure 13A:
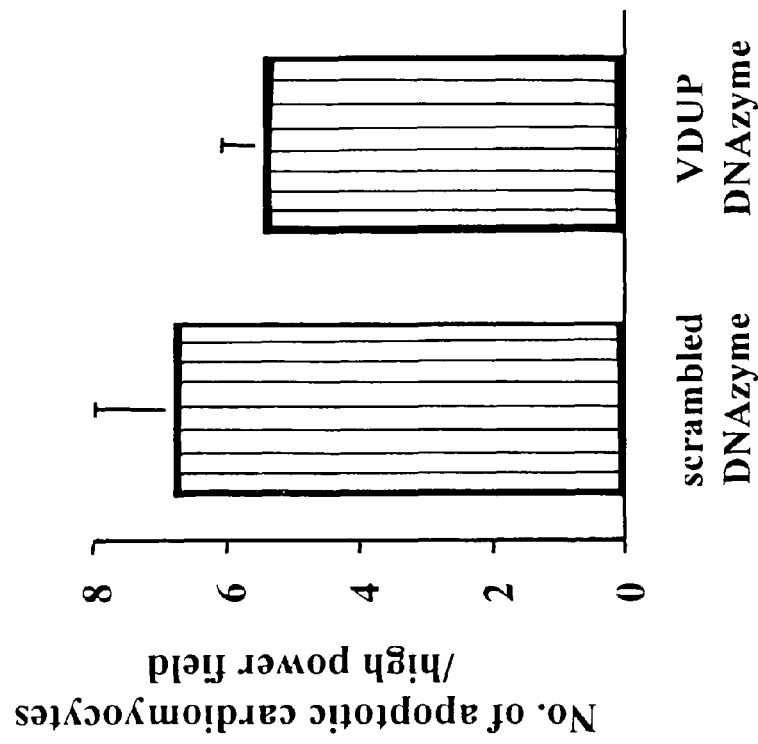

VDUP-1 DNAzyme Reduces Fibroblast Proliferation And Protects Against Cardiomyocyte Apoptosis. As shown in FIG. 13(a), intramyocardial injection of the rat sequence-specific VDUP1 DNA enzyme at 48 hours after LAD ligation resulted in a 75% mean inhibition of proliferating cardiac fibroblasts in the infarct zone two weeks later in comparison to injection of scrambled DNA enzyme control (p<0.01). In addition, as seen in FIG. 13(b), injection of VDUP1 DNA enzyme resulted in 20% mean reduction in apoptotic cardiomyocytes at the peri-infarct region relative to injection with the scrambled DNA enzyme control (p<0.05).

Figure 14B:
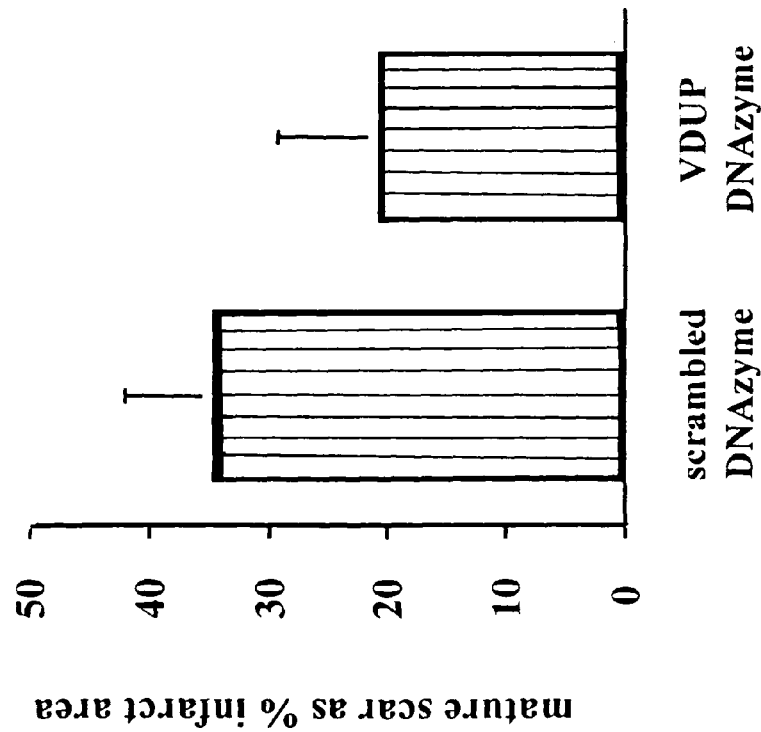
Figure 14A:
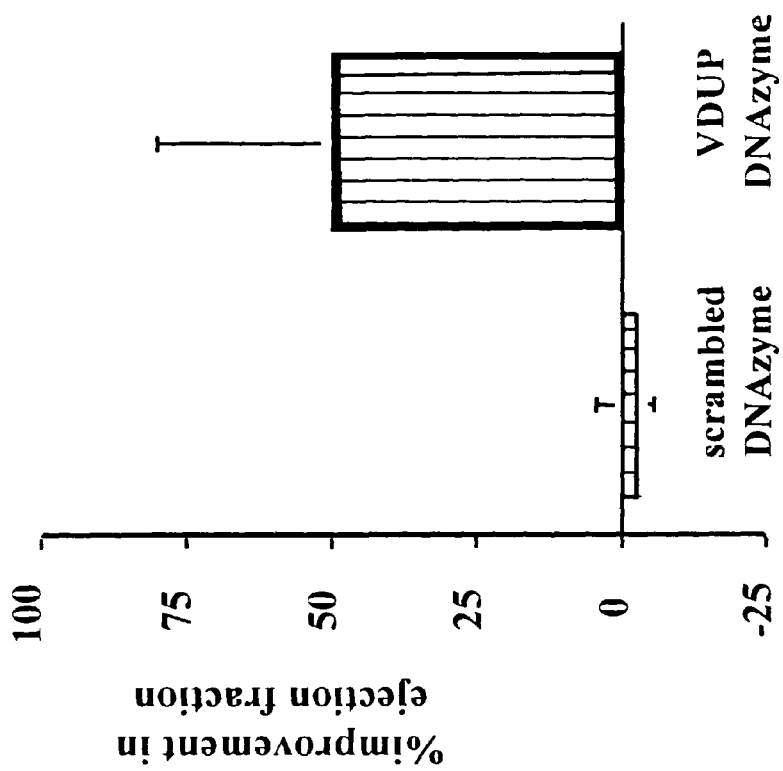

VDUP-1 DNAzyme Reduces Myocardial Scar And Improves Cardiac Function After Acute Infarction. Inhibition of fibroblast proliferation and cardiomyocyte apoptosis resulted in significant reduction of mature scar deposition in the infarct zone, from a mean of 35% for animals receiving control scrambled DNA enzyme to a mean of 20% for those receiving VDUP1 DNA enzyme, FIG. 14(a) (p<0.01). Most dramatic was the effect on cardiac function. As shown in FIG. 14(b), animals receiving VDUP1 DNA enzyme demonstrated a 50% mean recovery in cardiac function, as determined by ejection fraction, whereas no improvement was seen in animals receiving scrambled control DNA enzyme (p<0.01).

Clearly, VDUP1 DNA enzyme prevents cardiomyocyte apoptosis, cardiac fibroblast proliferation and scar formation, resulting in significant improvement in cardiac function after acute ischemia. These effects are presumably due to prevention of p38 MAP kinase activation and protection against redox damage. Similar results might be obtained by administering the VDUP1 DNA enzyme to other tissue sites of reduced blood flow such as the brain after cerebrovascular ischemia.

G-CSF

Figure 15A:
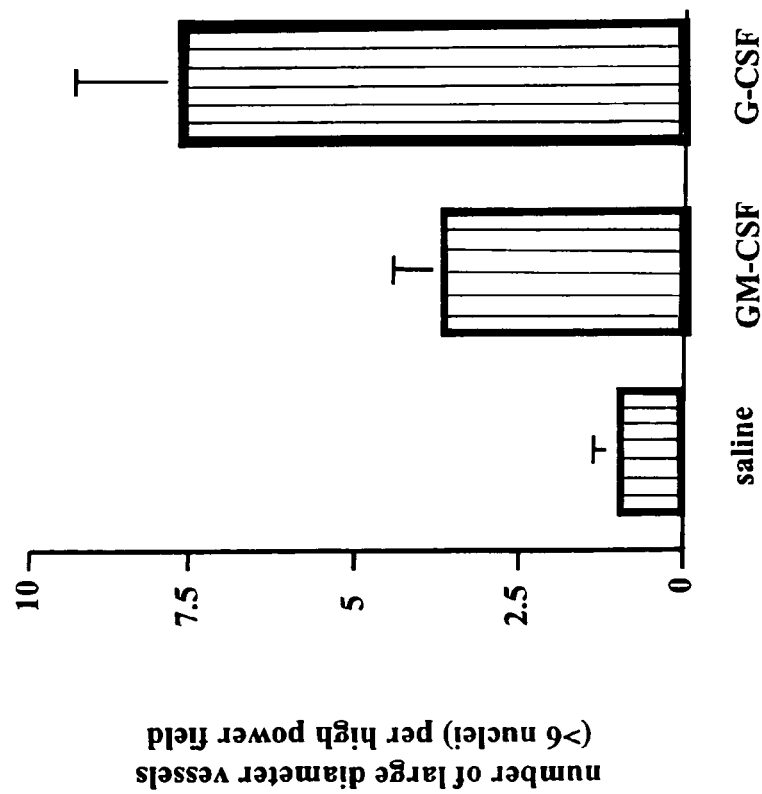

G-CSF is a more potent inducer of neovascularization after myocardial infarction than GM-CSF. As shown in FIG. 15(a), rats injected subcutaneously with human G-CSF at 10 ug/kg for four days starting at two days after myocardial infarction induced by left anterior descending (LAD) coronary artery ligation demonstrated approximately 7.5-fold greater numbers of large-diameter blood vessels at the peri-infarct region two weeks later relative to saline-treated controls (p<0.01). Rat GM-CSF administered at the same dosage regimen was less effective, though still inducing 4-fold greater numbers of large-lumen vessels than in control animals.

Additionally, G-CSF is a more potent inhibitor of cardiomyocyte apoptosis after myocardial infarction than GM-CSF. G-CSF injection was a more potent agent for protecting against cardiomyocyte apoptosis than GM-CSF used at the same dosage regimen, FIG. 15(b). G-CSF administration resulted in 36+16% reduction in the numbers of apoptotic cardiomyocytes at the peri-infarct region by two weeks relative to saline-treated controls (p<0.01), whereas GM-CSF only reduced apoptotic cardiomyocyte numbers by 12+9%.

Figure 16B:
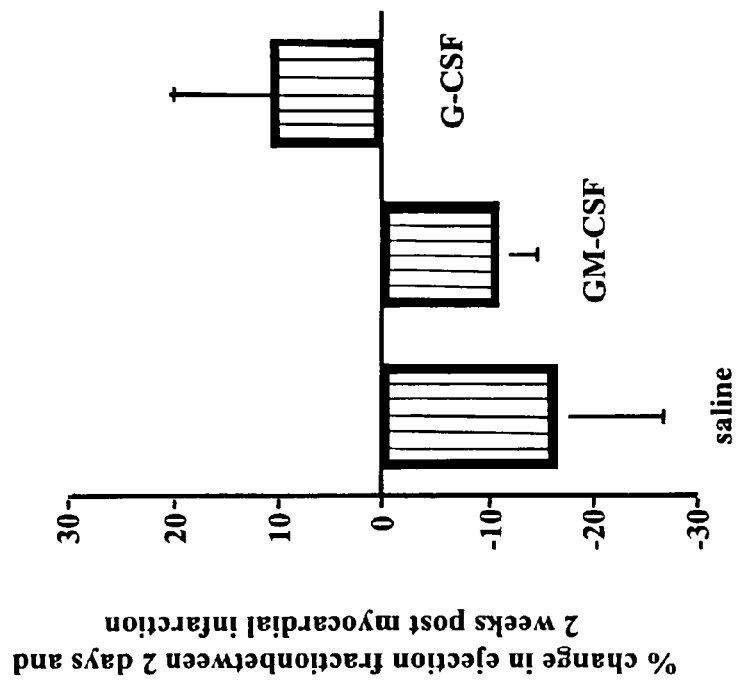
Figure 16A:
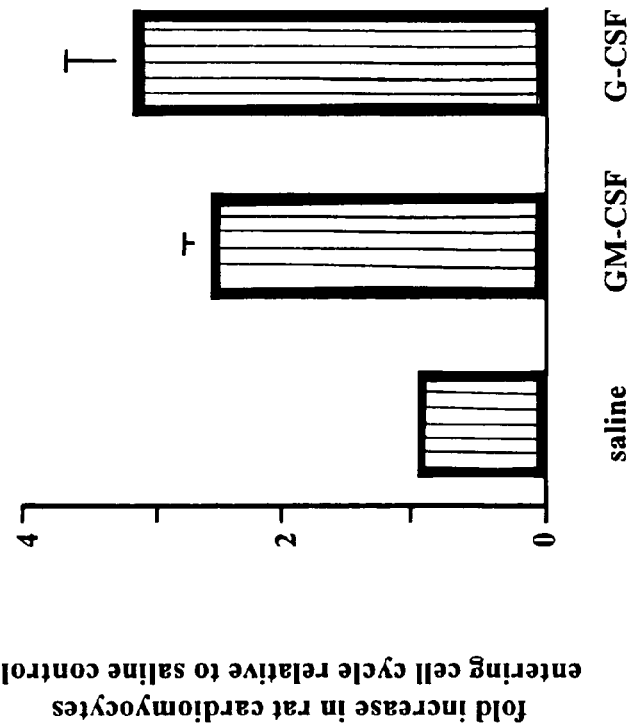

G-CSF is a more potent inducer of cardiomyocyte regeneration and functional cardiac recovery after myocardial infarction than GM-CSF. Next we examined the effects of bone marrow mobilization on cardiomyocyte cell cycling/regeneration and on functional cardiac recovery. As shown in FIG. 16(a), rats injected subcutaneously with human G-CSF at 10 ug/kg for four days starting at two days after myocardial infarction demonstrated 3.2-fold greater numbers of cycling cardiomyocytes two weeks later at the peri-infarct region relative to saline-treated controls (p<0.05). Rat GM-CSF administered at the same dosage regimen was less effective, resulting in 2.6-fold greater numbers of cycling cardiomyocytes. As shown in FIG. 16(b), this correlated with functional cardiac recovery. Whereas saline-treated animals had a 17% mean loss in cardiac function from day 2 to day 14 after infarction as measured by ejection fraction, GM-CSF treated animals had a loss of only 10% in cardiac function, and G-CSF treated animals actually had a 10% mean improvement in cardiac function (P<0.01). We interpret these functional data to reflect the superior effects of G-CSF bone marrow mobilization on myocardial neovascularization, protection against cardiomyocyte apoptosis and induction of cardiomyocyte cell cycling.

Anti-CXCR4 Antibodies

Figure 17B:
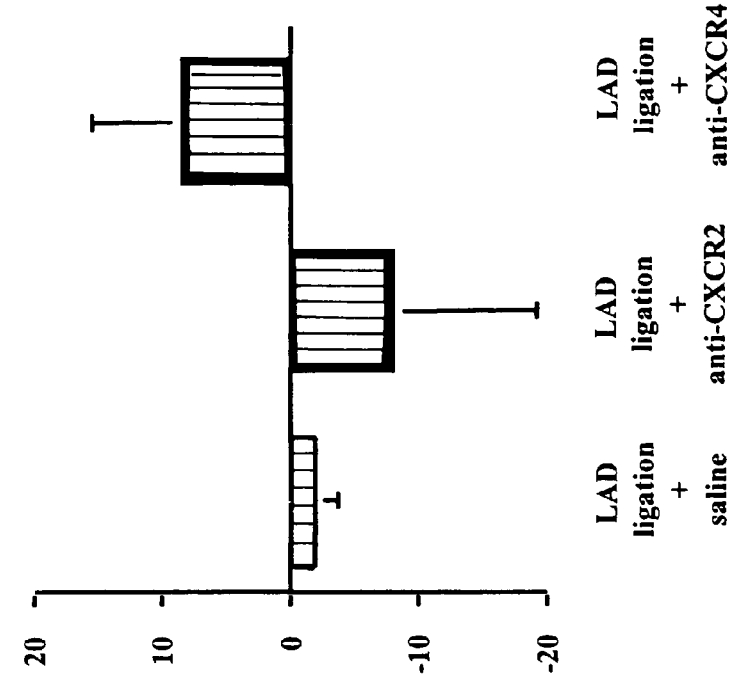
Figure 17A:
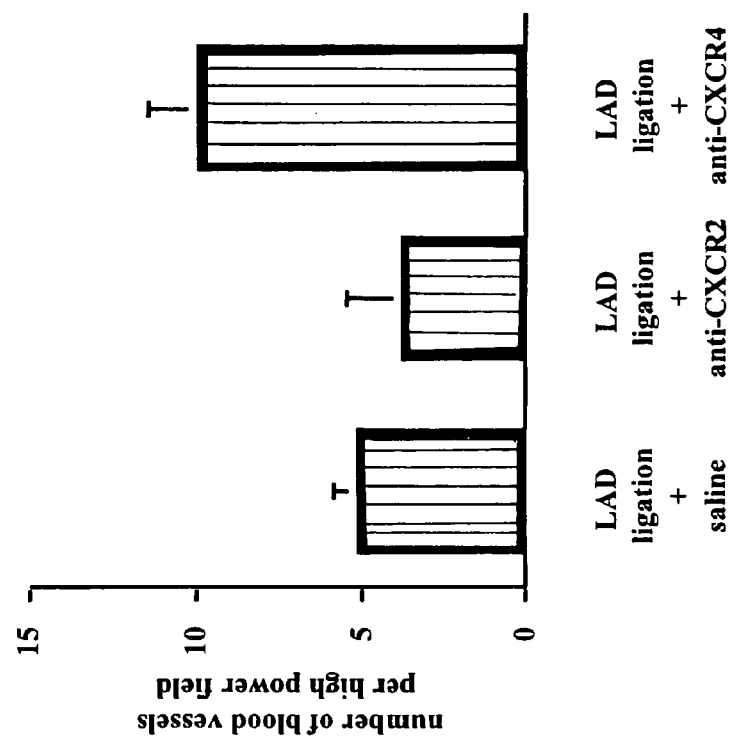

Intravenous administration of anti-CXCR4 antibody increases myocardial neovascularization and improves cardiac function after acute infarction. The major mechanism by which G-CSF causes mobilization of bone marrow elements is through interruption of interactions between the chemokine receptor CXCR4 on bone marrow resident stem cells and its ligand SDF-1. G-CSF induces both cleavage of the N-terminus of CXCR4 and accumulation of serine proteases which directly cleave and inactivate SDF-1. To examine whether similar mechanisms were responsible for the effects of G-CSF administration on myocardial neovascularization and improvement in cardiac function, we investigated the effect of interrupting CXCR4-SDF1 interactions by intravenously administering a monoclonal anti-CXCR4 antibody 48 hours after LAD ligation. As shown in FIG. 17(a) at two weeks after antibody administration animals receiving anti-CXCR4 mAb demonstrated a two-fold increase in neovascularization at the peri-infarct region compared with control animals receiving either saline or anti-CXCR2 mAb. Moreover, as seen in FIG. 17(b) anti-CXCR4 treated animals demonstrated a mean recovery in ejection fraction of 10% at two weeks whereas those receiving anti-CXCR2 mAb had a mean loss in cardiac function of 8% (p<0.05). These data support the concept that the observed effects of G-CSF administration result from interrupting CXCR4 interactions in the bone marrow, enabling endothelial progenitor cells to be mobilized to the peripheral circulation, and to home to ischemic myocardium where the resultant neovascularization results in improvement in cardiac function.

SDF-1

SDF-1 mRNA expression is not induced early in acutely ischemic myocardium, and its late induction is inhibited by GM-CSF. Next, we sought to identify a strategy by which the effects of GM-CSF could be augmented to approach those seen with G-CSF treatment alone, such as increasing chemotactic signals in the acutely ischemic myocardium. Since chemotaxis of CD34+ bone marrow stem cells is regulated by interactions between CXCR4 receptors on the CD34+ cells and the CXC chemokine SDF-1, we investigated whether SDF-1 mRNA expression was induced in the acutely ischemic myocardium. As shown in FIG. 18, no difference in myocardial SDF-1 mRNA was observed at 48 hours after LAD ligation in experimental animals relative to non-ischemic controls. By two weeks after infarction, myocardial SDF-1 mRNA expression had increased by 3.3-fold compared with saline-treated controls (p<0.01). We interpreted this delayed production of SDF-1 as most likely reflecting elaboration by infiltrating cells such as macrophages. In contrast, systemic GM-CSF administration was accompanied by approximately 4.5-fold inhibition in SDF-1 mRNA expression at two weeks, to levels actually lower than in non-ischemic controls. Since SDF-1 is a potent chemotactic factor for endothelial progenitor cells, these data suggested that systemic GM-CSF administration may result in suboptimal myocardial homing of endothelial progenitors due to decreased myocardial expression of chemotactic ligands such as SDF-1.

Intramyocardial injection of SDF-1 after acute myocardial infarction results in neovascularization and protection against cardiomyocyte apoptosis. To determine whether altered SDF-1 expression in the acutely ischemic heart affects endothelial progenitor cell chemotaxis and cardiomyocyte function, we examined the effects of direct intramyocardial injection of SDF-1 protein at 48 hours after LAD ligation. As shown in FIGS. 19 (a) and (b), intramyocardial injection of 4 ug/kg human recombinant SDF-1 in a total volume of 0.2 ml at 5 peri-infarct sites two days post-LAD ligation resulted by two weeks in a 5-fold increase in neovascularization and a 44+9% reduction in apoptotic cardiomyocytes at the peri-infarct region relative to control animals receiving intramyocardial saline injections (both p<0.05). The effects of intramyocardial SDF-1 injection on neovascularization and on extent of protection against cardiomyocyte apoptosis were in strikingly close parallel to the results obtained with systemic administration of G-CSF. Although addition of subcutaneously administered GM-CSF resulted in a synergistic increase in myocardial neovascularization, no further benefit in protection against cardiomyocyte apoptosis was observed. These results suggest that there is a finite amount of protection against cardiomyocyte apoptosis that can be induced by neovascularization, and that this cannot be improved upon by further by induction of additional new blood vessels.

Figure 20A:
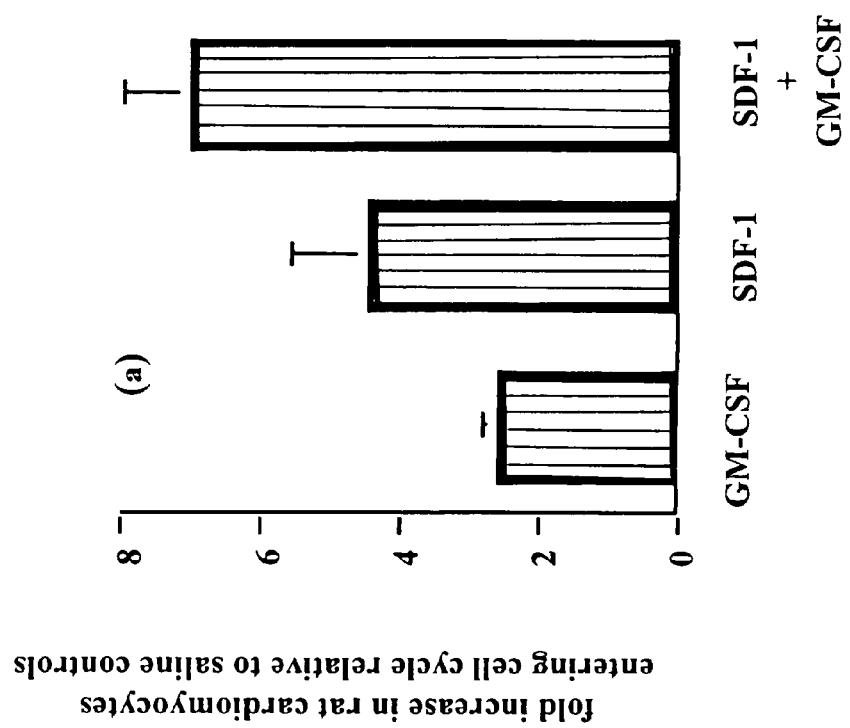

Intramyocardial injection of SDF-1 induces cardiomyocyte regeneration. As shown in FIG. 20(a), intramyocardial injection of 4 ug/kg human recombinant SDF-1 in a total volume of 0.2 ml at 5 peri-infarct sites two days post-LAD ligation resulted in a 4.5-fold increase in the number of cycling cardiomyocytes at the peri-infarct region relative to saline-injected controls (p<0.01). Addition of systemic GM-CSF administration resulted in synergistic effects on cardiomyocyte regeneration. Notably, the numbers of cycling cardiomyocytes at the peri-infarct region in animals receiving combined therapy with SDF-1 and GM-CSF significantly exceeded those seen in animals receiving G-CSF alone (7-fold versus 3.2-fold above saline treated controls, p<0.01). Since mean numbers of large-lumen vessels at the peri-infarct region were similar in animals receiving combined therapy with SDF-1 and GM-CSF and in those receiving G-CSF alone (8.0 vs 7.5/high power field), these data suggest that SDF-1 enhanced cardiomyocyte cycling/regeneration by an alternative mechanism in addition to induction of neovascularization.

Intramyocardial injection of SDF-1 improves cardiac function and is synergistic with bone marrow mobilization. Intramyocardial injection of SDF-1 resulted in a similar degree of functional myocardial recovery as was seen with systemic G-CSF administration (10% mean improvement in ejection fraction between days 2 and 14 post-LAD ligation compared with 10% mean improvement for G-CSF treated animals and 17% mean loss for saline-treated controls, p<0.01 for both treatment arms). Most strikingly, combining SDF-1 injection with bone marrow mobilization by GM-CSF resulted in significant augmentation in functional recovery (21% mean improvement in ejection fraction, p<0.01), FIG. 20(b). These data indicate that intramyocardial administration of SDF-1 causes improvement in cardiac function after acute ischemia through two separate mechanisms, a direct mechanism which involves induction of cardiomyocyte cycling and regeneration and an indirect mechanism operating through enhanced chemotaxis of mobilized bone marrow-derived endothelial progenitors and cardiac neovascularization.

We further investigated the role of SDF as an agent for inducing cardiac regeneration. We found that CXCR4 expression occurs following acute induced myocardial ischemia in focal and peri-infarct areas (see FIG. 26). In separate experiments, we found that intramyocardial injection of SDF-1 induced early phosphorylation of AKT (see FIG. 27). Furthermore, in cultured rat neonatal cardiomyocytes (which also express CXCR4, see FIG. 28), SDF administration induced phosphorylation of both AKT and ERK in a time-dependent manner. FIG. 29 shows rapid phosphorylation of AKT in cultured myocytes in the presence of SDF-1. Consistent with these results, further investigation demonstrated that intracardiac administration of SDF-1 augments G-CSF-induced neovascularization and regeneration of acutely ischemic myocardium (see FIG. 30). In addition, intracardiac administration of SDF-1 was also found to augment G-CSF-induced functional myocardial recovery following myocardial ischemia in rats (see FIG. 31), as well as protect rat neonatal cardiac myocytes against $H_2O_2$ apopotsis in a dose dependent manner (FIG. 32).

Discussion

Exogenous SDF may induce tissue repair via trophic effects on local or bone-marrow derived progenitors. In addition, increasing SDF-1 in the heart after ischemic insult may result in trophic effects on cardiomyocyte progenitors and induce cardiac repair and regeneration.

Methods and Materials

Purification and Characterization of Cytokine-Mobilized Human CD34+ Cells:

Single-donor leukopheresis products were obtained from humans treated with recombinant G-CSF 10 mg/kg (Amgen, CA) sc daily for four days. Donors were healthy individuals undergoing standard institutional procedures of bone marrow mobilization, harvesting and isolation for allogeneic stem cell transplants. Mononuclear cells were separated by Ficoll-Hypaque, and highly-purified CD34+ cells (>98% positive) were obtained using magnetic beads coated with anti-CD34 monoclonal antibody (mAb) (Miltenyi Biotech, CA). Purified CD34 cells were stained with fluorescein-conjugated mAbs against CD34 and CD117 (Becton Dickinson, CA), AC133 (Miltenyi Biotech, CA), CD54 (Immunotech, CA), CD62E (BioSource, MA), VEGFR-2, Tie-2, vWF, eNOS, CXCR1, CXCR2, and CXCR4 (all Santa Cruz Biotech, CA), and analyzed by four-parameter fluorescence using FACScan (Becton Dickinson, CA). Cells positively selected for CD34 expression were also stained with phycoerythrin (PE)-conjugated anti-CD117 mAb (Becton Dickinson, CA), and sorted for bright and dim fluorescence using a Facstar Plus (Becton Dickinson) and a PE filter. Intracellular staining for GATA-2 was performed by permeabilizing one million cells from each of the brightly and dimly fluorescing cell populations using a Pharmingen Cytofix/Cytoperm™ kit, incubating for 30 minutes on ice with 10 µl of fluorochrome-conjugated mAbs against both CD117 and CD34 surface antigens (Becton Dickinson, CA). After resuspension in 250 µl of Cytofix/Cytoperm™ solution for 20 minutes at 4 degrees C., cells were incubated with a fluorochrome-labeled mAb against GATA-2 (Santa Cruz Biotech, CA) or IgG control for 30 minutes at 4 degrees C., and analyzed by three-parameter flow cytometry.

Chemotaxis of Human Bone-Marrow Derived Endothelial Progenitors:

Highly-purified $CD34+CD117^{bright}$ cells (>98% purity) were plated in 48-well chemotaxis chambers fitted with membranes (8 mm pores) (Neuro Probe, MD). After incubation for 2 hours at 37° C., chambers were inverted and cells were cultured for 3 hours in medium containing IL-8, SDF-1 alpha/beta, and SCF at 0.2, 1.0 and 5.0 µg/ml. The membranes were fixed with methanol and stained with Leukostat™ (Fischer Scientific, Ill). Chemotaxis was calculated by counting migrating cells in 10 high-power fields.

Animals, Surgical Procedures, Injection of Human Cells, and Quantitation of Cellular Migration into Tissues:

Rowett (rnu/rnu) athymic nude rats (Harlan Sprague Dawley, Indianapolis, Ind.) were used in studies approved by the "Columbia University Institute for Animal Care and Use Committee". After anesthesia, a left thoracotomy was performed, the pericardium was opened, and the left anterior descending (LAD) coronary artery was ligated. Sham-operated rats had a similar surgical procedure without having a suture placed around the coronary artery. For studies on cellular migration, $2.0 \times 10^6$ CD34+ cells obtained from a single donor after G-CSF mobilization were injected into the tail vein 48 hours after LAD ligation either alone or together with 50 µg/ml monoclonal antibody (mAb) with known functional inhibitory activity against either human CXCR1, human CXCR2, human CXCR4, rat SDF-1 (all R & D Systems, MN), human CD34 (Pharmingen, CA), or rat IL-8 (Immuno-Laboratories, Japan). Controls received either isotype control antibodies at the same concentration or saline after LAD ligation. Prior to injection, $2.0 \times 10^6$ human cells were incubated with 2.5 µg/mL of the fluorescent carbocyanine DiI dye (Molecular Probes) for 5 minutes at 37° C. and 15 minutes at 4° C. After washing in PBS, DiI-labeled human cells were resuspended in saline and injected intravenously. $2.0 \times 10^6$ CD34+ human cells were also injected into the tail vein of sham-operated or LAD-ligated rats receiving three intramyocardial injections of 1.0 µg/ml recombinant human IL-8, SDF-1, SCF or saline. Each group consisted of 6-10 rats. Quantitation of myocardial infiltration after injection of human cells was performed by assessment of DiI fluorescence in hearts from rats sacrificed 2 days after injection (expressed as number of DiI-positive cells per high power field, minimum 5 fields examined per sample). Quantitation of rat bone marrow infiltration by human cells was performed in 12 rats at baseline, days 2, 7, and 14 by flow cytometric and RT-PCR analysis of the proportion of HLA class I-positive cells relative to the total rat bone marrow population. For studies on neoangiogenesis and effects on myocardial viability and function, $2.0 \times 10^6$ DiI-labelled human CD34+ cells obtained from a single donor after G-CSF mobilization were reconstituted with $10^3$, $10^5$, or $2.0 \times 10^5$ immunopurified $CD34+CD117^{bright}$ cells, and injected into the rat tail vein 48 hours after LAD ligation, in the presence or absence of a mAb with known inhibitory activity against CXCR4. Each group consisted of 6-10 rats. Histologic and functional studies were performed at 2 and 15 weeks.

Measurement of Rat CXC Chemokine mRNA and Protein Expression:

Poly(A)+ mRNA was extracted by standard methods from the hearts of 3 normal and 12 LAD-ligated rats. RT-PCR was used to quantify myocardial expression of rat IL-8 and Gro-alpha mRNA at baseline and at 6, 12, 24 and 48 hours after LAD ligation after normalizing for total rat RNA as measured by GAPDH expression. After priming with oligo (dT) 15-mer and random hexamers, and reverse transcribed with Moloney murine lymphotrophic virus reverse transcriptase (Invitrogen, Carlsbad, Calif., USA), cDNA was amplified in the polymerase chain reaction (PCR) using Taq polymerase (Invitrogen, Carlsbad, Calif., USA), radiolabeled dideoxynucleotide ([a32P]-ddATP: 3,000 Ci/mmol, Amersham, Arlington Heights, Ill.), and primers for rat Cinc (rat homologue of human IL-8/Gro-alpha and GAPDH (Fisher Genosys, CA). Primer pairs (sense/antisense) for rat Cinc and GAPDH were, gaagatagattgcaccgatg (SEQ ID NO:4)/catagcctctcacatttc SEQ ID NO:5), gcgcccgtccgccaatgagctgcgc SEQ ID NO:6)/cttggggacacccttcagcatcttttgg SEQ ID NO:7), and ctctacccacggcaagttcaa SEQ ID NO:8)/gggatgaccttgcccacagc SEQ ID NO:9), respectively. The labelled samples were loaded into 2% agarose gels, separated by electrophoresis, and exposed for radiography for 6 h at −70° C. Serum levels of rat IL-8/Gro-alpha were measured at baseline and at 6, 12, 24 and 48 hours after LAD ligation in four rats by a commercial ELISA using polyclonal antibodies against the rat IL-8/Gro homologue Cinc (ImmunoLaboratories, Japan). The amount of protein in each serum sample was calculated according to a standard curve of optical density (OD) values constructed for known levels of rat IL-8/Gro-alpha protein. Anti-Cinc antibodies were also used according to the manufacturer's instructions at 1:200 dilution in immunohistochemical studies to identify the cellular source of Cinc production in rat myocardium after LAD ligation. Positively-staining cells were visualized as dark gray through the Avidin/Biotin system described below.

Histology and Measurement of Infarct Size:

Following excision at 2 and 15 weeks, left ventricles from each experimental animal were sliced at 10-15 transverse sections from apex to base. Representative sections were fixed in formalin and stained for routine histology (H&E) to determine cellularity of the myocardium, expressed as cell number per high power field (HPF) (600×). A Masson trichrome stain was performed, which labels collagen blue and myocardium red, to evaluate collagen content on a semi-quantitative scale (0-3+), with 1+ light blue, 2+ light blue and patches of dark blue, and 3+ dark blue staining. This enabled measurement of the size of the myocardial scar using a digital image analyzer. The lengths of the infarcted surfaces, involving both epicardial and endocardial regions, were measured with a planimeter digital image analyzer and expressed as a percentage of the total ventricular circumference. Final infarct size was calculated as the average of all slices from each heart. All studies were performed by a blinded pathologist. Infarct size was expressed as percent of total left ventricular area. Final infarct size was calculated as the average of all slices from each heart.

Quantitation of Capillary Density:

In order to quantitate capillary density and species origin of the capillaries, additional sections were stained freshly with mAbs directed against rat or human CD31 (Serotec, UK, and Research Diagnostics, NJ, respectively), factor VIII (Dako, CA), and rat or human MHC class I (Accurate Chemicals, CT). Arterioles were differentiated from large capillaries by the presence of a smooth muscle layer, identified by staining sections with a monoclonal antibody against muscle-specific desmin (Dako, Ca). Staining was performed by immunoperoxidase technique using an Avidin/Biotin Blocking Kit, a rat-absorbed biotinylated anti-mouse IgG, and a peroxidase-conjugate (all Vector Laboratories Burlingame, Calif.). Capillary density was determined at 2 weeks post infarction from sections labeled with anti-CD31 mAb, and confirmed with anti-factor VIII mAb, and compared to the capillary density of the unimpaired myocardium. Values are expressed as the number of CD31-positive capillaries per HPF (400×).

Quantitation of Cardiomyocyte Proliferation:

Cardiomyocyte DNA synthesis and cell cycling was determined by dual staining of rat myocardial tissue sections obtained from LAD-ligated rats at two weeks after injection of either saline or CD34+ human cells, and from healthy rats as negative controls, for cardiomyocyte-specific troponin I and human- or rat-specific Ki-67. Briefly, paraffin embedded sections were microwaved in a 0.1M EDTA buffer, and stained with either a primary monoclonal antibody against rat Ki-67 at 1:3000 dilution (gift of Giorgio Catoretti, Columbia University) or human Ki-67 at 1:300 dilution (Dako, CA) and incubated overnight at 4 degrees C. Following washes, sections were incubated with a species-specific secondary antibody conjugated with alkaline phosphatase at 1:200 dilution (Vector Laboratories Burlingame, Calif.) for 30 minutes and positively-staining nuclei were visualized as blue with a BCIP/NBT substrate kit (Dako, CA). Sections were then incubated overnight at 4 degrees C. with a monoclonal antibody against cardiomyocyte-specific troponin I (Accurate Chemicals, CT) and positively-staining cells were visualized as dark gray through the Avidin/Biotin system described above. Cardiomyocytes progressing through cell cycle in the infarct zone, peri-infarct region, and area distal to the infarct were calculated as the proportion of troponin I-positive cells per high power field co-expressing Ki-67.

Measurement of Myocyte Apoptosis by DNA End-Labeling of Paraffin Tissue Sections:

For in situ detection of apoptosis at the single cell level we used the TUNEL method of DNA end-labeling mediated by dexynucleotidyl transferase (TdT) (Boehringer Mannheim, Mannheim, Germany). Rat myocardial tissue sections were obtained from LAD-ligated rats at two weeks after injection of either saline or CD34+ human cells, and from healthy rats as negative controls. Briefly, tissues were deparaffinized with xylene and rehydrated with graded dilutions of ethanol and two washes in phosphate-buffered saline (PBS). The tissue sections were then digested with Proteinase K (10 µg/ml in Tris/HCL) for 30 minutes at 37° C. The slides were then washed 3 times in PBS and incubated with 50 µl of the TUNEL reaction mixture (TdT and fluorescein-labeled dUTP) and incubated in a humid atmosphere for 60 minutes at 37° C. For negative controls TdT was eliminated from the reaction mixture. Following 3 washes in PBS, the sections were then incubated for 30 minutes with an antibody specific for fluorescein-conjugated alkaline phosphatase (AP) (Boehringer Mannheim, Mannheim, Germany). The TUNEL stain was visualized with a substrate system in which nuclei with DNA fragmentation stained blue, (BCIP/NBT substrate system, Dako, Carpinteria, Calif.). The reaction was terminated following three minutes of exposure with PBS. To determine the proportion of blue-staining apoptotic nuclei within myocytes, tissue was counterstained with a monoclonal antibody specific for desmin. Endogenous peroxidase was blocked by using a 3% hydrogen perioxidase solution in PBS for 15 minutes, followed by washing with 20% goat serum solution. An anti-troponin I antibody (Accurate Chemicals, CT) was incubated overnight (1:200) at 40 degrees C. Following 3 washes sections were then treated with an anti-rabbit IgG, followed by a biotin conjugated secondary antibody for 30 minutes (Sigma, Saint Louis, Mo.). An avidin-biotin complex (Vector Laboratories, Burlingame, Calif.) was then added for an additional 30 minutes and the myocytes were visualized dark gray following 5 minutes exposure in DAB solution mixture (Sigma, Saint Louis, Mo.). Tissue sections were examined microscopically at 200× magnification. Within each 200× field 4 regions were examined, containing at least 250 cells per region and cumulatively approximating 1 mm$^2$ of tissue, at both the peri-infarct site and distally to this site. Stained cells at the edges of the tissue were not counted. Results were expressed as the mean number of apoptotic myocytes per mm$^2$ at each site examined.

Analysis of Myocardial Function:

Echocardiographic studies were performed using a high frequency liner array transducer (SONOS 5500, Hewlett Packard, Andover, Mass.). 2D images were obtained at mid-papillary and apical levels. End-diastolic (EDV) and end-systolic (ESV) left ventricular volumes were obtained by bi-plane area-length method, and % left ventricular ejection fraction was calculated as [(EDV-ESV)/EDV]×100.

cDNA Subtractive Hybridization:

Briefly, messenger RNA was isolated from each heart, and 1 µg was used for first-strand cDNA synthesis with random primers. The subtractive hybridization was performed with the PCR-select cDNA subtraction kit (CLONTECH), following the manufacturer's recommendations. After second-strand synthesis, the two cDNA libraries were digested with RsaI. Digestion products of the "tester" library were ligated to a specific adapter (T7 promoter), then hybridized with a 30-fold excess of the "driver" library for subtraction. After hybridization, the remaining products were further amplified by PCR. In the forward subtraction, which determines the genes that are overexpressed in the ischemic sample, the ischemic tissue is the "tester" and the normal tissue is the "driver." In the reverse subtraction, the "tester" and the "driver" are switched to determine the genes that are down-regulated in the ischemic sample.

Rat Neonatal Cardiac Myocyte Culture:

Neonatal cardiac myocytes were isolated from ventricles of 1 to 3-day old Sprague Dawley rats. Myocytes were isolated by step-wise enzymatic digestion using a modification of a previously described method (Sadoshima et al., 1992, J.

Biol. Chem. 267:10551-10560). PERCOLL gradient was used to enrich for cardiac myocytes during isolation. Myocytes were plated onto gelatin-coated dishes or chamber slides (LABTEK PERMANOX, Nunc) in DMEM/F12 media containing 5% horse serum. Sixteen hours following plating cells were washed and serum starved if required.

Protein Isolation:

Rat Isolated Ventricle.

Isolated ventricles were frozen in liquid nitrogen and stored at −80° C. Frozen ventricle were Polytron homogenised on ice (3 times, 10-s bursts) in RIPA buffer containing 50 mM Tris-HCl (pH 7.4), 150 mM NaCl, 1 mM EDTA, 1 nM PMSF, 1 µg/ml aprotinin, 1 µg/ml leupeptin, 1 mM $Na_3VO_4$ and 1 mM NaF. NP-40 (final concentration 1%) was added for 30 min, then samples were Dounce homogenized on ice (60 strokes). Following centrifugation (6000 rpm, 15 min) the protein concentration of the supernatant was determined (BIORAD Protein Assay).

Neonatal Rat Cardiac Myocytes.

Myocytes were washed twice with ice-cold PBS before collection in RIPA buffer containing the above described components. Following 15-min incubation on an orbital rocker at 4° C., samples were passed 4 times through a 21G needle. Supernatant was collected after centrifugation (14,000 rpm, 15 min) and protein concentration determined (BIORAD Protein Assay).

Western Blot Method:

Rat Isolated Ventricle.

Protein extracts (100 µg) prepared in SDS sample buffer were resolved by SDS/PAGE. PVDF membranes were blocked in PBST containing 5% BSA for 1 h, before overnight incubation with anti-phospho AKT or anti-AKT antibodies diluted 1:1000 in PBST containing 5% BSA (CELL SIGNALING). Densitometric quantification was performed using IMAGEQUANT software (Molecular Dynamics).

Neonatal Rat Cardiac Myocytes.

Serum starved cells were stimulated with SDF-1α at the concentrations and times described. Protein extracts (50 µg) prepared in SDS sample buffer were resolved by SDS/PAGE. PVDF membranes were blocked in PBST containing 5% BSA and incubated overnight with anti-phospho AKT or anti-AKT antibodies diluted 1:1000 in PBST containing 5% BSA (Cell Signalling). Nitrocellulose membranes were blocked in PBST containing 5% skim milk for 1 h prior to overnight incubation with anti-phospho ERK or anti-ERK antibodies diluted 1:1000 in PBST containing 5% skim milk (CELL SIGNALING). Densitometric quantification was performed using IMAGEQUANT software (Molecular Dynamics).

CXCR4 Immunostaining:

Rat Isolated Ventricle.

Cross-sections of ventricle were formalin (10%) fixed and embedded in paraffin. Sections (4 µm) were de-waxed and endogenous peroxide activity was blocked using 3% $H_2O_2$ (20 min). After 1 h blocking using swine serum (1:5 dilution, DAKO), sections were incubated overnight with fusin (CXCR4; H-118, Santa Cruz Biotechnology) at a 1:400 dilution. Immunostaining was developed using a biotinylated secondary antibody (DAKO) linked to avidin/HRP (VectaStain Elite ABC Kit, Vector Laboratories) followed by DAB chromagen (DAKO). Slides were counterstained with haematoxylin.

Neonatal Rat Cardiac Myocytes.

Cells cultured on chamber slides (LabTek Permanox, Nunc) were rinsed with PBS and fixed with ice-cold methanol for 5 min. Endogenous peroxide activity was inhibited using 3% $H_2O_2$ diluted in methanol for 5 min. Slides were blocked for 1 h in swine serum (1:5 dilution, DAKO), and then incubated overnight with fusin (CXCR4; H-118, Santa Cruz Biotechnology) at a 1:200 dilution. Immunostaining was developed using a biotinylated secondary antibody (DAKO) linked to avidin/HRP (VECTASTAIN ELITE ABC Kit, Vector Laboratories) followed by DAB chromagen (DAKO).

REFERENCES

1. Soonpaa M H, Field L J. Assessment of cardiomyocyte DNA synthesis in normal and injured adult mouse hearts. Am J Physiol 272, H220-6 (1997).
2. Kellerman S, Moore J A, Zierhut W, Zimmer H G, Campbell J, Gerdes A M. Nuclear DNA content and nucleation patterns in rat cardiac myocytes from different models of cardiac hypertrophy. J Mol Cell Cardiol 24, 497-505 (1992).
3. Colucci, W. S. Molecular and cellular mechanisms of myocardial failure. Am. J. Cardiol. 80(11A), 15L-25L (1997).
4. Ravichandran, L. V. and Puvanakrishnan, R. In vivo labeling studies on the biosynthesis and degradation of collagen in experimental myocardial myocardial infarction. Biochem. Intl. 24, 405-414 (1991).
5. Agocha, A., Lee, H. W., Eghali-Webb, M. Hypoxia regulates basal and induced DNA synthesis and collagen type I production in human cardiac fibroblasts: effects of TGF-beta, thyroid hormone, angiotensis II and basic fibroblast growth factor. J. Mol. Cell. Cardiol. 29, 2233-2244 (1997).
6. Pfeffer, J. M., Pfeffer, M. A, Fletcher, P. J., Braunwald, E. Progressive ventricular remodeling in rat with myocardial infarction. Am. J. Physiol. 260, H1406-414 (1991).
7. Kocher, A A, et al. Neovascularization of ischemic myocardium by human bone-marrow-derived endothelial progenitor cells prevents cardiomyocyte apoptosis, reduces remodeling and improves cardiac function. Nat Med 7, 430-6 (2001).
8. Kennedy, M. et al. A common precursor for primitive erythropoiesis and definitive haematopoiesis. Nature 386, 488-493 (1997).
9. Choi, K., Kennedy, M., Kazarov, A., Papadimitriou, Keller, G. A common precursor for hematopoietic and endothelial cells. Development 125, 725-732 (1998).
10. Elefanty, A. G., Robb, L., Birner, R., Begley, C. G. Hematopoietic-specific genes are not induced during in vitro differentiation of scl-null embryonic stem cells. Blood 90, 1435-1447 (1997).
11. Labastie, M. C., Cortes, F., Romeo, P. H., Dulac, C., Peault, B. Molecular identity of hematopoietic precursor cells emerging in the human embryo. Blood 92, 3624-3635 (1998).
12. Rafii S, et al. Isolation and characterization of human bone marrow microvascular endothelial cells: hematopoietic progenitor cell adhesion. Blood 84, 10-19 (1994).
13. Shi, Q. et al. Evidence for circulating bone marrow-derived endothelial cells. Blood 92, 362-367 (1998).
14. Lin, Y., Weisdorf, D. J., Solovey, A., Hebbel, R. P. Origins of circulating endothelial cells and endothelial outgrowth from blood. J. Clin. Invest. 105, 71-77 (2000).
15. Asahara, T. et al. Isolation of putative progenitor cells for endothelial angiogenesis. Science 275, 964-967 (1997).
16. Takahashi, T. et al. Ischemia- and cytokine-induced mobilization of bone marrow-derived endothelial progenitor cells for neovascularization. Nat. Med. 5, 434-438 (1999).
17. Kalka, C. et al. Transplantation of ex vivo expanded endothelial progenitor cells for therapeutic neovascularization. Proc. Natl. Acad. Sci. USA 97, 3422-3427 (2000).

18. Kajstura J, Leri A, Finato N, di Loreto N, Beltramo C A, Anversa P. Myocyte proliferation in end-stage cardiac failure in humans. Proc Natl Acad Sci USA 95, 8801-8805 (1998).
19. Beltrami A P, et al. Evidence that human cardiac myocytes divide after myocardial infarction. N Engl J Med 344, 1750-7 (2001).
20. Folkman J. Angiogenesis in cancer, vascular, rheumatoid and other disease. Nat. Med. 1:27 (1995).
21. Strieter, R M. et al. Interleukin-8: a corneal factor that induces neovascularization. Am. J. Pathol. 141, 1279-1284 (1992).
22. Murdoch C, Monk P N, Finn A. Cxc chemokine receptor expression on human endothelial cells. Cytokine 11, 704-12 (1999).
23. Koch, A E. et al. Interleukin-8 (IL-8) as a macrophage-derived mediator of angiogenesis. Science, 258:1798-1801 (1992).
24. Strieter, R M, et al The functional role of the ELR motif in CXC chemokine-mediated angiogenesis. J. Biol. Chem. 270, 27348-27357 (1995).
25. Angiolillo, A L, et al. Human interferon-inducible protein 10 is a potent inhibitor of angiogenesis in vivo. J Exp Med 182, 155-62 (1995).
26. Feil C, Augustin H G. Endothelial cells differentially express functional CXC-chemokine receptor-4 (CXCR-4/fusin) under the control of autocrine activity and exogenous cytokines. Biochem Biophys Res Commun 247, 38-45 (1998).
27. Tachibana, K. et al. The chemokine receptor CXCR4 is essential for vascularization of the gastrointestinal tract. Nature 393, 591-594 (1998).
28. Mohle R, Bautz F, Rafii S, Moore M A, Brugger W, Kanz L. The chemokine receptor CXCR-4 is expressed on CD34+ hematopoietic progenitors and leukemic cells and mediates transendothelial migration induced by stromal cell-derived factor-1. Blood 91, 4523-30 (1998).
29. Imai, K. et al. Selective secretion of chemoattractants for haemopoietic progenitor cells by bone marrow endothelial cells: a possible role in homing of haemopoietic progenitor cells to bone marrow. Br J Haematol 106, 905-11 (1999).
30. Peled, A. et al. Dependence of human stem cell engraftment and repopulation of NOD/SCID mice on CXCR4. Science 283, 845-88 (1999).
31. Voermans C, Gerritsen W R, von dem Borne A E, van der Schoot C E. Increased migration of cord blood-derived CD34+ cells, as compared to bone marrow and mobilized peripheral blood CD34+ cells across uncoated or fibronectin-coated filters. Exp. Hematol. 27, 1806-14 (2000).
32. Janowska-Wieczorek, A. et al. Growth factors and cytokines upregulate gelatinase expression in bone marrow CD34+ cells and their transmigration through reconstituted basement membrane. Blood 93, 3379-3390 (1999).
33. Heymans, S. et al. Inhibition of plasminogen activators or matrix metalloproteinases prevents cardiac rupture but impairs therapeutic angiogenesis and causes cardiac failure. Nat. Med. 5, 1135-1142 (1999).
34. Luca M, Huang S, Gershenwald J E, Singh R K, Reich R, Bar-Eli M. Expression of interleukin-8 by human melanoma cells up-regulates MMP-2 activity and increases tumor growth and metastasis. Am J Pathol 151, 1105-1113 (1997).
35. Masure, S., Proost, P., Van Damme, J., Opdenakker, M D. Purification and identification of 91-kDa neutrophil gelatinase. Release by the activating peptide interleukin-8. Eur. J. Biochem. 198, 391-398 (1991).
36. Hart, P. H. et al. Activation of human monocytes by granulocyte-macrophage colony-stimulating factor: increased urokinase-type plasminogen activator activity. Blood 77, 841-848 (1991).
37. Stacey, K. J., Fowles, L. F., Colman, M. S., Ostrowski, M. C., Hume, D. A. Regulation of urokinase-type plasminogen activator gene transcription by macrophage colony-stimulating factor. Mol. Cell. Biol. 15, 3430-3441 (1995).
38. Pei, X. H. et al. G-CSF increases secretion of urokinase-type plasminogen activator by human lung cancer cells. Clin. Exp. Metastasis 16, 551-558 (1998).
39. Semerad, C L, et al. A role for G-CSF receptor signalling in the regulation of hematopoietic cell function but not lineage commitment or differentiation. Immunity 11, 153-161 (1999).
40. Nagasawa, T, et al. Defects of B-cell lymphopoiesis and bone-marrow myelopoiesis in mice lacking the CXC chemokine PBSF/SDF-1. Nature 382, 635-638 (1996).
41. Rempel S A, Dudas S, Ge S, Gutierrez J A. Identification and localization of the cytokine SDF1 and its receptor, CXC chemokine receptor 4, to regions of necrosis and angiogenesis in human glioblastoma. Clin Cancer Res 6, 102-11 (2000).
42. Globerson, A. Hematopoietic stem cells and aging. Exp. Gerontol. 34, 137-146 (1999).
43. de la Rubia, J., Diaz, M. A., Verdeguer, A., et al. Donor age-related differences in PBPC mobilization with rHuG-CSF. Transfusion 41, 201-205 (2001).
44. Leferovich J M, et al. Heart regeneration in adult MRL mice. Proc Natl Acad Sci USA 98, 9830-9835 (2001).
45. Vander Heiden M G, Plas D R, Rathmell J C, Fox C J, Harris M H, Thompson C B. Growth factors can influence cell survival through effects on glucose metabolism. Mol Cell Biol 21, 5899-5912 (2001).
46. Rössig L, Jadidi A S, Urbich C, Badorff C, Zeiher A M, and Dimmeler S. Akt-dependent phosphorylation of p21Cip1 regulates PCNA binding and proliferation of endothelial cells. Mol Cell Biol 21, 5644-5657 (2001).
47. Tomita S, et al. Autologous transplantation of bone marrow cells improves damaged heart function. Circulation 100, 11-247 (1999).
48. Orlic D, et al. Bone marrow cells regenerate infarcted myocardium. Nature 410, 701-705 (2001)
49. Kehat I, et al. Human embryonic stem cells can differentiate into myocytes with structural and functional properties of cardiomyocytes. J Clin Invest. 108, 407-14 (2001).
50. Rossi et al., 1992, Aids Research and Human Retroviruses 8, 183.
51. Hampel et al., EP0360257
52. Hampel and Tritz, 1989 Biochemistry 28, 4929.
53. Hampel et al., 1990 Nucleic Acids Res. 18, 299.
54. Perrotta and Been, 1992 Biochemistry 31, 16.
55. Guerrier-Takada et al., 1983 Cell 35, 849.
56. Forster and Altman, 1990 Science 249, 783.
57. Saville and Collins, 1990 Cell 61, 685-696.
58. Saville and Collins, 1991 Proc. Natl. Acad. Sci. USA 88, 8826-8830.
59. Guo and Collins, 1995 EMBO J. 14, 368.
60. Cech et al., U.S. Pat. No. 4,987,071.
61. Matzura O, Wennborg A (1996) RNAdraw: an integrated program for RNA secondary structure calculation and analysis under 32-bit Microsoft Windows. *Comput Appl Biosci* 12:247-9.
49. Santoro S W, Joyce G F (1997) A general purpose RNA-cleaving DNA enzyme. *Proc Natl Acad Sci USA* 94:4262-6.

50. Santoro S W, Joyce G F (1998) Mechanism and utility of an RNA-cleaving DNA enzyme. *Biochemistry* 37:13330-42.
51. MacLellan W R and Schneider M D. Genetic dissection of cardiac growth control pathways Annu. Rev. Physiol. 2000. 62:289-320.7.
52. Sherr C J, Roberts J M. CDK inhibitors: positive and negative regulators of G(1)-phase progression. Genes Dev. 1999; 13:1501-1512.
53. Hill M F, Singal P K. Antioxidant and oxidative stress changes during heart failure subsequent to myocardial infarction in rats. Am J Pathol. 1996, 148:291-300.
54. Hill M F, Singal P K. Right and left myocardial antioxidant responses during heart failure subsequent to myocardial infarction. Circulation 1997 96:2414-20.
55. Li, Y., Jenkins, C. W., Nichols, M. A. and Xiong, Y. (1994) Cell cycle expression and p53 regulation of the cyclin-dependent kinase inhibitor p21. Oncogene, 9, 2261-2268
56. Steinman, R. A., Hoffman, B., Iro, A., Guillouf, C., Liebermann, D. A. and El-Houseini, M. E. (1994) Induction of p21 (WAF1/CIP1) during differentiation. Oncogene, 9, 3389-3396
57. Halevy, O., Novitch, B. G., Spicer, D. B., Skapek, S. X., Rhee, J., Hannon, G. J., Beach, D. and Lassar, A. B. (1995) Correlation of terminal cell cycle arrest of skeletal muscle with induction of p21 by MyoD. Science, 267, 1018-1021.
58. Andres, V. and Walsh, K. (1996) Myogenin expression, cell cycle withdrawal and phenotypic differentiation are temporally separable events that precedes cell fusion upon myogenesis. J. Cell Biol., 132, 657-666.
59. Tsurimoto, T. PCNA Binding Proteins. Frontiers in Bioscience, 4:849-858, 1999.
60. Levkau B, Koyama H, Raines E W, Clurman B E, Herren B, Orth K, Roberts J M, Ross R. Cleavage of p21cip1/waf1 and p27 kip1 mediates apoptosis in endothelial cells through activation of cdk2: role of a caspase cascade. Mol Cell. 1998; 1:553-563.
61. Adachi S, et al. Cyclin A/cdk2 activation is involved in hypoxia-induced apoptosis in cardiomyocytes Circ Res. 88:408, 2001.
62. Ichijo H, et al. Induction of apoptosis by ASK1, a mammalian MAPKKK that activates SAPK/JNK and p38 signaling pathways. Science 275:90-94 (1997).
63. Tobiume, K., Inage, T., Takeda, K., Enomoto, S., Miyazono, K. and Ichijo, H. (1997) Molecular cloning and characterization of the mouse apoptosis signal-regulating kinase 1. Biochem. Biophys. Res. Commun., 239, 905-910.
64. Asada M, Yamada T, Ichijo h, Delia D, Miyazono K, Fukumuro K, and Mizutani S Apoptosis inhibitory activity of cytoplasmic p21Cip1/WAF1 in monocytic differentiation. EMBO J, 18:1223-1234, 1999.
65. Saitoh H, et al. Mammalian thioredoxin is a direct inhibitor of apoptosis signal-regulating kinase (ASK)1. EMBO J. 17: 2596-2606, 1998.
66. Nishiyama A, et al. Identification of Thioredoxin-binding Protein-2/Vitamin D3 Up-regulated Protein 1 as a Negative Regulator of Thioredoxin Function and Expression. J Biol Chem, 31, 21645-21650, 1999.
67. Junn E, et al. Vitamin D3 Up-Regulated Protein1 Mediates Oxidative Stress Via Suppressing the Thioredoxin Function. J. Immunol. 164:6287-6295, 2000.
68. Holmgren, A. (1985) Annu. Rev. Biochem. 54, 237-271.
69. Chae, H. Z., Chung, S. J. & Rhee, S. G. (1994) J. Biol. Chem. 269, 27670-27678.
70. Netto, L. E. S., Chae, H. Z., Kang, S., Rhee, S. G. & Stadtman, E. R. (1996) J. Biol. Chem. 271, 15315-15321.
71. Chae, H. Z., Uhm, T. B. & Rhee, S. G. (1994) Proc. Natl. Acad. Sci USA 91, 7022-7026.
72. Kwon, S. J., Park, J., Choi, W., Kim, I. H. & Kim, K. (1994) Biochem. Biophys. Res. Comm. 201, 8-15.
73. Kang, S. W., Baines, I. C. & Rhee, S. G. (1998) J. Biol. Chem. 273, 6303-6311.
74. Hirotsu, S, et al. Crystal structure of a multifunctional 2-Cys peroxiredoxin heme-binding protein 23 kDa/proliferation-associated gene product. Proc. Natl. Acad Sci, USA. 96, 12333-12338, 1999.
75. Siow, R. C. M., et al. (1995) FEBS Lett. 368, 239-242.
76. Prosperi, M., Ferbus, D., Karczinski, I. & Goubin, G. (1993) J. Biol. Chem. 268, 11050-11056.
77. Sauri, H., Butterfield, L., Kim, A. & Shau, H. (1995) Biochem. Biophys. Res. Commun. 208, 964-969.
78. Ishii T et al. Transcription factor Nrf2 coordinately regulates a group of oxidative stress-inducible genes in macrophages. J Biological Chem 2000, 275:16023-16029
79. Itoh K, Wakabayashi N, Katoh Y, Ishii T, Igarashi K, Engel J D, Yamamoto M. Keap1 represses nuclear activation of antioxidant responsive elements by Nrf2 through binding to the amino-terminal Neh2 domain. Genes Dev. 1999 Jan. 1; 13(1):76-86.
80. Lee, J-M, et al. Phosphatidylinositol 3-Kinase, Not Extracellular Signal-regulated Kinase, Regulates Activation of the Antioxidant-Responsive Element in IMR-32 Human Neuroblastoma Cells J. Biol. Chem., 276:20011-20016, 2001.
81. Kim Y C, Masutani H, Yamaguchi Y, Itoh K, Yamamoto M, Yodoi J. Hemin-induced activation of the thioredoxin gene by Nrf2. A differential regulation of the antioxidant responsive element by a switch of its binding factors. J Biol Chem. 2001 276:18399-406.
82. Cho H Y, Jedlicka A E, Reddy S P, Kensler T W, Yamamoto M, Zhang L Y, Kleeberger S R. Role of NRF2 in Protection Against Hyperoxic Lung Injury in Mice. Am J Respir Cell Mol Biol 2002, 26:175-182.
83. Kumuda C. Das, Paula M. B. Pahl, Xiao-Ling Guo, and Carl W. White. Induction of Peroxiredoxin Gene Expression by Oxygen in Lungs of Newborn Primates. Am. J. Respir. Cell Mol. Biol. 2001, 25:226-232.
84. Wen S-T, and Van Etten, R A The PAG gene product, a stress-induced protein with antioxidant properties, is an Abl SH3-binding protein and a physiological inhibitor of c-Abl tyrosine kinase activity. Genes and Development, 19: 2456-2467, 1997.
85. Kharbanda, S., Yuan, Z. M., Weichselbaum, R. & Kufe, D. Determination of cell fate by c-Abl activation in the response to DNA damage. Oncogene 17, 3309-3318 (1998).
86. Yuan Z M et al, Nature 1996 18; 382(6588):272-4.
87. Jost, C. A., Marin, M. C. & Kaelin, W. J. p73 is a human p53-related protein that can induce apoptosis. Nature 389, 191-194 (1997).
88. Agami, R, Blandino G, Oren M, Shaul Y. Interaction of c-Abl and p73 [alpha] and their collaboration to induce apoptosis Nature 399, 809-813 (1999).
89. Sun X, et al. Activation of the cytoplasmic c-Abl tyrosine kinase by reactive oxygen species. J Biol. Chem. 2000, 275:17237-17240.
90. Kumar S, et al. Targeting of the c-Abl Tyrosine Kinase to Mitochondria in the Necrotic Cell Death Response to Oxidative Stress J. Biol. Chem., 276, 17281-17285, 2001.
91. Chen, K. S, and DeLuca, H. F. Isolation and characterization of a novel cDNA from HL-60 cells treated with 1,25-dihydroxyvitamin D-3 JOURNAL Biochim. Biophys. Acta 1219 (1), 26-32 (1994).

92. Zhang et al. Clinical Pharmacology & Therapeutics (1995) 58(1), 44-53.
93. Tetsuro Ishii, Ken Itoh, Junetsu Akasaka, Toru Yanagawa, Satoru Takahashil, Hiroshi Yoshida, Shiro Bannai and Masayuki Yamamoto, Carcinogenesis Vol. 21(5):1013-1016, (2000).
94. Das K C, Pahl P M, Guo X L, White C W, Am. J. Respir. Cell Mol. Biol., (2001), 25(2):226-32.
95. Immenschuh S, Iwahara S, Satoh H, Nell C, Katz N, Muller-Eberhard U., Biochemistry (1995) 17; 34(41):13407-11.
96. Ken Itoh, Nobunao Wakabayashi, Yasutake Katoh, Tetsuro Ishii, Kazuhiko Igarashi, James Douglas Engel, 1 and Masayuki Yamamoto, Genes and Development, 13(1):76-86, (1999).

Experimental Results II

Intravenous Administration of Human Bone Marrow-Derived Endothelial Progenitor Cells Induces Neovascularization and Prevents Cardiomyocyte Apoptosis within Five Days Post-Infarction.

We sought to determine how soon after intravenous injection of bone marrow-derived endothelial progenitor cells does neovascularization develop in hearts of rats having undergone permanent LAD ligation 48 hours earlier. When animals were sacrificed at two days after intravenous injection of DiI-labelled human CD34+ cells obtained by G-CSF mobilization (>98% CD34 purity, containing 6-12% CD117bright angioblasts), numerous DiI positive interstitial cells were seen in the peri-infarct region, but no defined vascular structures expressing DiI could be identified, data not shown. In contrast, animals sacrificed at five days post-infusion of human CD34+ cells demonstrated numerous DiI-positive vascular structures at the peri-infarct region and 3.5-fold higher numbers of capillaries in comparison to rats receiving saline, FIG. 21(*a*) (p<0.01). The increase in microvascularity at 5 days was accompanied by 3.3-fold lower numbers of apoptotic cardiomyocytes at the peri-infarct region, defined by dual positivity for troponin I and TUNEL, in comparison to controls receiving saline, FIG. 21(*b*) (p<0.01). Together, these data indicate that the vasculogenic process of differentiation and organization of bone marrow-derived angioblasts to a mature, functional network of capillaries in the ischemic myocardium takes from two to five days.

Intravenous Administration of Human Bone Marrow-Derived Endothelial Progenitor Cells Induces Cell Cycling of Cardiomyocyte Progenitors and Cardiomyocyte Differentiation.

We examined cardiac tissue from experimental and control animals sacrificed at five days by immunohistochemistry and confocal microscopy for evidence of cycling cardiomyocytes, as has been suggested to occur rarely in the adult heart after acute ischemia. While no mature troponin-positive cycling cardiomyocytes were detected in any control or experimental animals at day 5 post-infarction, animals receiving human bone marrow-derived CD34+ cells demonstrated numerous clusters of small, cycling cells at the peri-infarct region that were of rat origin, as defined by a monoclonal antibody specific for rat Ki67, FIG. 22(*a*). These cells were negative for cardiomyocyte-specific troponin I, a marker of cardiomyocyte differentiation, but stained positively for alpha-sarcomeric actin, indicating they were immature cells of cardiomyocyte lineage. Similar clusters of cycling cardiomyocyte progenitors were not seen in control animals injected with saline.

Tissues obtained from animals sacrificed at two weeks after human CD34+ administration no longer demonstrated clusters of small, cycling cardiomyocyte progenitors, but instead a high frequency of large, mature rat cardiomyocytes at the peri-infarct region with detectable DNA activity, as determined by dual staining with mAbs reactive against cardiomyocyte-specific troponin I and rat Ki67, FIGS. 22(*b*) and (*c*). The number of cycling, mature cardiomyocytes at the peri-infarct region was 4-fold higher in animals receiving human endothelial progenitor cells than in LAD-ligated controls receiving saline (p<0.01) in whom there was a high frequency of cells with fibroblast morphology and reactivity with rat Ki67, but not troponin I. We speculate that the cycling, mature cardiomyocytes seen at day 14 post-infarction in animals who received human endothelial progenitor cells are the differentiated progeny of the small, cycling immature cardiomyocyte progenitors seen in the same anatomical location at day 5 and accompanying the onset of neovascularization. Whether the cycling cardiomyocyte progenitors represent in situ cardiac stem cells normally residing in the heart in a quiescent state, or whether these cells have migrated to the heart from elsewhere in the body, such as the bone marrow, remains to be determined.

Myocardial Expression of HBP23, a Rat Peroxiredoxin Protecting Cells Against Damage by Oxygen Radicals, is Decreased by Ischemia and Increased by Neovascularization.

We next sought to identify a molecular mechanism to explain the relationship between neovascularization at the peri-infarct region and proliferation/regeneration of adjacent cardiomyocyte progenitors. We first performed cDNA subtractive hybridization in order to identify patterns of changes in gene expression between normal rat hearts and rat hearts 48 hours after LAD ligation. Since deficits in antioxidants and increased oxidative stress accompanying myocardial infarction have been directly implicated in the pathogenesis of post-infarct heart failure (13-15), we chose to examine changes in expression of particular antioxidant genes. A family of antioxidant enzymes known as peroxiredoxins, which demonstrate peroxidase activity (16) and are induced by oxygen (17), play a critical role in regulating cell survival during periods of oxidative stress, such as ischemia. They serve to maintain the thiol-disulfide status of the cytosol by undergoing reversible oxidation-reduction reactions involving electron transfer via disulfide bridges formed with thioredoxin (TRX), which constitutes one of the principal cellular reducing systems in mammals (18). In addition, peroxiredoxins can inhibit c-Abl tyrosine kinase activity induced by oxidative stress (19,20) and can rescue cells from both a pro-apoptotic state and cell cycle arrest induced by the activated c-Abl gene product (21). By cDNA subtractive hybridization, we found that expression of the rat peroxiredoxin HBP23 mRNA was reduced in rat hearts 48 hours after LAD ligation compared with normal rat hearts. By RT-PCR, HBP23 mRNA levels in rat hearts decreased at two weeks post-LAD ligation by a mean of 34% compared with normal rat hearts, FIG. 23 (p<0.01). In contrast, HBP23 mRNA levels in LAD-ligated rat hearts two weeks after receiving human angioblasts returned to levels only 14% lower than in non-ischemic controls. Since mRNA expression of peroxiredoxins is induced by oxygen, these data suggested that HBP23 mRNA expression was inhibited by the acute ischemic event and induced following angioblast-dependent neovascularization.

Generation of a DNA Enzyme to Cleave HBP23 mRNA.

To investigate whether induced expression of HBP23 is involved in the mechanism by which neovascularization affects myocardial cellular apoptosis, regeneration/proliferation, and function, we generated a catalytic DNA enzyme targeting specific sequences within the rat HBP23 gene (22, 23). We chose to specifically target pyrimidine-purine junctions at or near the translational start site AUG of messenger RNA for rat HBP23, a region that is conserved between species and has low relative free energy (24). In this region, the rat HBP23 sequence differs by only one base from the human homologue, proliferation-associated gene (PAG). To produce the control DNA enzyme, the nucleotide sequence in the two flanking arms of the HBP23 DNA enzyme was scrambled without altering the catalytic domain. The 3' terminus of each molecule was capped with an inverted 3'-3'-linked thymidine for resistance to 3'-to-5' exonuclease digestion.

The DNA enzyme against HBP23 cleaved the 23-base oligonucleotide synthesized from the sequence of rat HBP23 mRNA, in a dose- and time-dependent manner, FIG. 24 (a). In contrast, the DNA enzyme did not cleave a 23-base oligonucleotide form the human homologue PAG which differs from the rat HBP23 oligonucleotide by only one base, demonstrating its exquisite target specificity. A DNA enzyme with specificity for the same translational start site in the human PAG gene efficiently cleaved the PAG oligonucleotide, but not the one derived from HBP23 (data not shown). The scrambled control DNA enzyme did not cleave either oligonucleotide. To determine the effect of the DNA enzyme on endogenous HBP23 production, cardiomyocyte monolayers obtained from fetal rat hearts were grown to confluence and transfected with species-specific DNA enzymes or scrambled control. Densitometric analysis of RT-PCR products following reverse transcription of cellular mRNA showed that the HBP23 DNA enzyme inhibited steady-state mRNA levels in cultured rat cells by over 80%, FIG. 24 (b), relative to the scrambled DNA.

In Vivo Administration of a DNA Enzyme to Prevent Induction Of HBP23 mRNA in Rat Myocardium: Neovascularization is not Affected, but its Effects on Cardiomyocyte Apoptosis, Regeneration, and Function are Abrogated.

To investigate the in vivo relevance of induced expression of HBP23 in experimental myocardial infarction, 48 hours after LAD ligation rats were injected with human bone marrow-derived endothelial progenitor cells intravenously together with intramyocardial injections of either HBP23 DNA enzyme or scrambled control. As shown in FIG. 25 (a), HBP23 DNA enzyme had no effect on induction of neovascularization by human bone marrow angioblasts. When sacrificed at day 5 post-infusion, rats who received human endothelial progenitors, irrespective of whether HBP23 DNA enzyme or scrambled control was co-injected, demonstrated increased myocardial capillary density in comparison to saline controls. In contrast, injection of the HBP23 DNA enzyme, but not the scrambled control, abrogated the anti-apoptotic effects of neovascularization, FIG. 25 (b), and the improvement in cardiac function, FIG. 25 (c). Among animals receiving human endothelial progenitor cells and demonstrating myocardial neovascularization, treatment with HBP23 DNA enzyme resulted in 1.7-fold higher levels of cardiomyocyte apoptosis ($p<0.01$) and 38% mean deterioration in cardiac function as assessed by echocardiography ($p<0.01$). In addition, the HBP23 DNA enzyme exerted striking effects on cardiomyocyte progenitor proliferation/regeneration. Whereas peri-infarct clusters of small rat cells expressing Ki67 and alpha-sarcomeric actin were easily detected in animals receiving angioblasts together with the scrambled control DNA, none were identified in animals receiving the HBP23 DNA enzyme. These results clearly demonstrate that angioblast-dependent neovascularization protects cardiomyocytes against apoptosis and induces proliferation/regeneration of resident cardiomyocyte lineage progenitors via pathways regulated by peroxiredoxin gene products.

Discussion

In this study we showed that neovascularization of ischemic myocardium by human bone marrow derived angioblasts results in both protection of mature cardiomyocytes at the peri-infarct region against apoptosis and stimulation of cardiomyocyte progenitors at the same site to enter cell cycle, proliferate and regenerate. Moreover, we showed that the mechanism by which angioblast-dependent neovascularization regulates cardiomyocyte survival and self-renewal appears to involve at least one family of genes involved in anti-apoptotic and pro-proliferative pathways accompanying oxidative stress, the peroxiredoxins. While oxygen tension positively regulates peroxiredoxin gene expression (17), whether this alone explains the positive effect of angioblast-mediated neovascularization on HBP mRNA expression is not clear. Since peroxiredoxin mRNA expression is induced by protein kinase C delta (25) it is possible that bone marrow angioblasts may be a source of extracellular signals regulating protein kinase C delta activation and consequently cell survival, such as FGF-1 (26).

Deficits in antioxidants and increased oxidative stress accompanying myocardial infarction have been directly implicated in the pathogenesis of post-infarct heart failure (13-15). Our study suggests that reduced levels of peroxiredoxins post-infarction may be of direct causality in the subsequent remodelling and failure of the left ventricle. The antioxidant effects of peroxiredoxins are coupled with the physiological electron donor activity of the TRX system (27-29). In addition to directly interacting with TRX, the peroxiredoxin gene products specifically bind the SH3 domain of c-Abl, a non-receptor tyrosine kinase, inhibiting its activation (21). Activation of c-Abl through the SH3 domain by stimuli such as agents that damage DNA induces either arrest of the cell cycle in phase G1 or cellular apoptosis (30). Cell cycle arrest is dependent on the kinase activity of c-Abl which downregulates the activity of the cyclin-dependent kinase Cdk2 and induces the expression of p21 (31). By associating with c-Abl in vivo, peroxiredoxins can inhibit tyrosine phosphorylation induced by c-Abl overexpression and rescue cells from both the cytostatic and pro-apoptotic effects of the activated c-Abl gene product (32). Our in vivo demonstration that co-administration of a DNA enzyme directed against the rat peroxiredoxin HBP23 abrogated the anti-apoptotic and pro-proliferative effects of human angioblast-dependent neovascularization in the infarcted rat heart argues strongly that this family of genes is directly implicated in the mechanism of action by which neovascularization results in improvement in cardiac function and prevention of heart failure.

Throughout life, a mixture of young and old cells is present in the normal myocardium. Although most myocytes seem to be terminally differentiated, there is a fraction of younger myocytes that retains the capacity to replicate (33). In the present study, human angioblast-dependent neovascularization resulted, within five days, in proliferation of small, endogenous rat cardiomyocyte precursors at the peri-infarct region. The dividing myocyte precursors could be identified by immunohistochemical criteria on the basis of concomitant cell surface expression of alpha-sarcomeric actin, but not troponin I, and proliferating nuclear structures, defined by an antibody specific for rat Ki67. Since this process was followed within fourteen days by increasing numbers in the same location of mature, cycling cardiomyocytes, defined on the basis of morphology, cell surface expression of troponin I, and nuclear expression of Ki67, we conclude that cycling cardiomyocyte precursors differentiated in situ to become new, mature, functional cardiomyocytes. Whether these precursors are derived from a resident pool of cardiomyocyte stem cells or from a renewable source of circulating bone marrow-derived stem cells that home to the damaged myocardium remains to be determined. Moreover, while the signals required for in situ expansion of cardiomyocyte precursors appear to involve, at least in part, pathways regulated by members of the peroxiredoxin gene family, the signals required for cardiomyocyte differentiation are, at present, unknown. Gaining an understanding of these issues may open the possibility of manipulating the biology of endogenous cardiomyocytes in order to augment the healing process after myocardial ischemia.

Methods and Materials

Purification and Characterization of Cytokine-Mobilized Human CD34+ Cells.

Single-donor leukopheresis products were obtained from humans treated with recombinant G-CSF 10 mg/kg (Amgen, CA) sc daily for four days. Donors were healthy individuals undergoing standard institutional procedures of bone marrow mobilization, harvesting and isolation for allogeneic stem cell transplants. Mononuclear cells were separated by Ficoll-Hypaque, and highly-purified CD34+ cells (>98% positive) were obtained using magnetic beads coated with anti-CD34 monoclonal antibody (mAb) (Miltenyi Biotech, CA). Purified CD34 cells were stained with fluorescein-conjugated mAbs against CD34 and CD117 (Becton Dickinson, CA), AC133 (Miltenyi Biotech, CA), CD54 (Immunotech, CA), CD62E (BioSource, MA), VEGFR-2, Tie-2, vWF, eNOS, CXCR1, CXCR2, and CXCR4 (all Santa Cruz Biotech, CA), and analysed by four-parameter fluorescence using FACScan (Becton Dickinson, CA). Cells positively selected for CD34 expression were also stained with phycoerythrin (PE)-conjugated anti-CD117 mAb (Becton Dickinson, CA), and sorted for bright and dim fluorescence using a Facstar Plus (Becton Dickinson) and a PE filter. Intracellular staining for GATA-2 was performed by permeabilizing one million cells from each of the brightly and dimly fluorescing cell populations using a Pharmingen Cytofix/Cytoperm kit, incubating for 30 minutes on ice with 10 ul of fluorochrome-conjugated mAbs against both CD117 and CD34 surface antigens (Becton Dickinson, CA). After resuspension in 250 ul of Cytofix/Cytoperm solution for 20 minutes at 4 degrees C., cells were incubated with a fluorochrome-labeled mAb against GATA-2 (Santa Cruz Biotech, CA) or IgG control for 30 minutes at 4 degrees C., and analyzed by three-parameter flow cytometry.

Animals, Surgical Procedures, and Injection of Human Cells.

Rowett (rnu/rnu) athymic nude rats (Harlan Sprague Dawley, Indianapolis, Ind.) were used in studies approved by the "Columbia University Institute for Animal Care and Use Committee". After anesthesia, a left thoracotomy was performed, the pericardium was opened, and the left anterior descending (LAD) coronary artery was ligated. Sham-operated rats had a similar surgical procedure without having a suture placed around the coronary artery.

Histology and Measurement of Infarct Size.

Following excision at 2 and 15 weeks, left ventricles from each experimental animal were sliced at 10-15 transverse sections from apex to base. Representative sections were fixed in formalin and stained for routine histology (H&E) to determine cellularity of the myocardium, expressed as cell number per high power field (HPF) (600×). A Masson trichrome stain was performed, which labels collagen blue and myocardium red, to evaluate collagen content on a semi-quantitative scale (0-3+), with 1+ light blue, 2+ light blue and patches of dark blue, and 3+ dark blue staining. This enabled measurement of the size of the myocardial scar using a digital image analyzer. The lengths of the infarcted surfaces, involving both epicardial and endocardial regions, were measured with a planimeter digital image analyzer and expressed as a percentage of the total ventricular circumference. Final infarct size was calculated as the average of all slices from each heart. All studies were performed by a blinded pathologist (MJS). Infarct size was expressed as percent of total left ventricular area. Final infarct size was calculated as the average of all slices from each heart.

Quantitation of Capillary Density.

In order to quantitate capillary density and species origin of the capillaries, additional sections were stained freshly with mAbs directed against rat or human CD31 (Serotec, UK, and Research Diagnostics, NJ, respectively), factor VIII (Dako, CA), and rat or human MHC class I (Accurate Chemicals, CT). Arterioles were differentiated from large capillaries by the presence of a smooth muscle layer, identified by staining sections with a monoclonal antibody against muscle-specific desmin (Dako, Ca). Staining was performed by immunoperoxidase technique using an Avidin/Biotin Blocking Kit, a rat-absorbed biotinylated anti-mouse IgG, and a peroxidase-conjugate (all Vector Laboratories Burlingame, Calif.). Capillary density was determined at 5 days and 2 weeks post infarction from sections labeled with anti-CD31 mAb, and confirmed with anti-factor VIII mAb, and compared to the capillary density of the unimpaired myocardium. Values are expressed as the number of CD31-positive capillaries per HPF (400×).

Quantitation of Cardiomyocyte Proliferation.

Cardiomyocyte DNA synthesis and cell cycling was determined by dual staining of rat myocardial tissue sections obtained from LAD-ligated rats at two weeks after injection of either saline or CD34+ human cells, and from healthy rats as negative controls, for cardiomyocyte-specific troponin I and human- or rat-specific Ki67. Briefly, paraffin embedded sections were microwaved in a 0.1M EDTA buffer, and stained with either a primary monoclonal antibody against rat Ki67 at 1:3000 dilution (gift of Giorgio Catoretti, Columbia University) or human Ki67 at 1:300 dilution (Dako, CA) and incubated overnight at 4 degrees C. Following washes, sections were incubated with a species-specific secondary antibody conjugated with alkaline phosphatase at 1:200 dilution (Vector Laboratories Burlingame, Calif.) for 30 minutes and positively-staining nuclei were visualized as blue with a BCIP/NBT substrate kit (Dako, CA). Sections were then incubated overnight at 4 degrees C. with a monoclonal antibody against cardiomyocyte-specific troponin I (Accurate Chemicals, CT) and positively-staining cells were visualized as brown through the Avidin/Biotin system described above. Cardiomyocytes progressing through cell cycle in the infarct zone, peri-infarct region, and area distal to the infarct were calculated as the proportion of troponin I-positive cells per high power field co-expressing Ki67. For confocal microscopy, fluorescein isothiocyanate (FITC)-conjugated rabbit anti-mouse IgG was used as secondary antibody to detect Ki67 in nuclei. A Cy5-conjugated mouse mAb against alpha-sarcomeric actin (clone 5C5; Sigma) was used to detect cardiomyocytes, and propidium iodide was used to identify all nuclei.

Measurement of Myocyte Apoptosis by DNA End-Labeling of Paraffin Tissue Sections.

For in situ detection of apoptosis at the single cell level we used the TUNEL method of DNA end-labeling mediated by dexynucleotidyl transferase (TdT) (Boehringer Mannheim, Mannheim, Germany). Rat myocardial tissue sections were obtained from LAD-ligated rats at two weeks after injection of either saline or CD34+ human cells, and from healthy rats as negative controls. Briefly, tissues were deparaffinized with xylene and rehydrated with graded dilutions of ethanol and two washes in phosphate-buffered saline (PBS). The tissue sections were then digested with Proteinase K (10 ug/ml in Tris/HCL) for 30 minutes at 370 C. The slides were then washed 3 times in PBS and incubated with 50 ul of the TUNEL reaction mixture (TdT and fluorescein-labeled dUTP) and incubated in a humid atmosphere for 60 minutes at 370 C. For negative controls TdT was eliminated from the reaction mixture. Following 3 washes in PBS, the sections were then incubated for 30 minutes with an antibody specific for fluorescein-conjugated alkaline phosphatase (AP) (Boehringer Mannheim, Mannheim, Germany). The TUNEL stain was visualized with a substrate system in which nuclei with DNA fragmentation stained blue, (BCIP/NBT substrate system, DAKO, Carpinteria, Calif.). The reaction was terminated following three minutes of exposure with PBS. To determine the proportion of blue-staining apoptotic nuclei within myocytes, tissue was counterstained with a monoclonal antibody specific for desmin. Endogenous peroxidase was blocked by using a 3% hydrogen perioxidase solution in PBS for 15 minutes, followed by washing with 20% goat serum solution. An anti-troponin I antibody (Accurate Chemicals, CT) was incubated overnight (1:200) at 40 degrees C.

Following 3 washes sections were then treated with an anti-rabbit IgG, followed by a biotin conjugated secondary antibody for 30 minutes (Sigma, Saint Louis, Mo.). An avidin-biotin complex (Vector Laboratories, Burlingame, Calif.) was then added for an additional 30 minutes and the myocytes were visualized brown following 5 minutes exposure in DAB solution mixture (Sigma, Saint Louis, Mo.). Tissue sections were examined microscopically at 20× magnification. Within each 20× field 4 regions were examined, containing at least 250 cells per region and cumulatively approximating 1 mm2 of tissue, at both the peri-infarct site and distally to this site. Stained cells at the edges of the tissue were not counted. Results were expressed as the mean number of apoptotic myocytes per mm2 at each site examined.

Analyses of Myocardial Function:

Echocardiographic studies were performed using a high frequency liner array transducer (SONOS 5500, Hewlett Packard, Andover, Mass.). 2D images were obtained at mid-papillary and apical levels. End-diastolic (EDV) and end-systolic (ESV) left ventricular volumes were obtained by bi-plane area-length method, and % left ventricular ejection fraction was calculated as [(EDV-ESV)/EDV]×100.

cDNA Subtractive Hybridization:

This technique enabled comparison of the pattern of gene expression between hearts from normal rats and rats who underwent left anterior descending (LAD) coronary artery ligation 48 hours earlier. Briefly, messenger RNA was isolated from each heart, and 1 μg was used for first-strand cDNA synthesis with random primers. The subtractive hybridization was performed with the PCR-select cDNA subtraction kit (CLONTECH), following the manufacturer's recommendations. After second-strand synthesis, the two cDNA libraries were digested with RsaI. Digestion products of the "tester" library were ligated to a specific adapter (T7 promoter), then hybridized with a 30-fold excess of the "driver" library for subtraction. After hybridization, the remaining products were further amplified by PCR. In the forward subtraction, which determines the genes that are overexpressed in the ischemic sample, the ischemic tissue is the "tester" and the normal tissue is the "driver." In the reverse subtraction, the "tester" and the "driver" are switched to determine the genes that are down-regulated in the ischemic sample.

Reverse Transcription-Polymerase Chain Reaction (RT-PCR) Analysis of HBP23 mRNA Expression:

Total RNA was extracted using RNeasy Kits from Qiagen (Valencia, Calif.) from normal rat hearts or from hearts of rats who underwent LAD ligation two weeks earlier and received either saline or human angioblasts. RNA was reverse transcribed with SMART cDNA Synthesis Kit (Clontech, Palo Alto, Calif.). Amplification reactions were conducted in a 25 ul volume with an initial step of 94 C for 5 min, followed by 26-32 cycles of 94 C for 30 sec and 68 C for 1 min, using TITANIUM Taq PCR Kits (Clontech, Palo Alto, Calif.). Primers for HBP23 were 5'-GCTGATGAAGG-TATCTCTTTCAGGGGCCTC (SEQ ID NO:10) and 5'-GATGGTCTGCCCCTTACCAATAGTGGAAG (SEQ ID NO:11). Rat GAPDH was used as internal control (forward primer 5'TGAAGGTCGGAGTCAACGGATTTG3' (SEQ ID NO:12), reverse primer 5'CATGTGGGCCA TGAGG TCCA CCAC3' (SEQ ID NO:13)). Ethidium bromide stained bands of amplified fragments were quantified by densitometric.

DNA Enzymes and RNA Substrates:

DNA enzymes with 3'-3' inverted thymidine were synthesized by Integrated DNA technologies (Coralville, Iowa) and purified by RNase-free IE-HPLC or RP-HPLC. The short RNA substrates corresponding to target DNA enzyme sequences were chemically synthesized followed by RNAse-free PAGE purification and also made by in vitro transcription from a DNA template. Rat HBP23 cDNA and human PAG cDNA were amplified by RT-PCR from total RNA of cultured rat fetal cardiomyocytes and HUVEC, respectively, using the following primer pair: 5'TTTACCCTCTTGACTT-TACTTTTGTGTGTCCCAC3' (forward primer) (SEQ ID NO:10) and 5'CCAGCTGGGCACACTTCACCATG3' (reverse primer) (SEQ ID NO:11). HBP23 and PAG cDNA were cloned into pGEM-T vectors (Promega) to obtain plasmid constructs pGEM-ratHBP23 and pGEM-humanPAG. cDNA sequences were verified using an automatic sequencing machine. 32P-labeled-nucleotide rat HBP23 and human PAG RNA transcripts were prepared by in vitro transcription (SP6 polymerase, Promega) in a volume of 20 ml for 1 hour at 32° C. Unincorporated label and short nucleotides (<350base) were separated from radiolabeled species by centriguration on Chromaspin-200 columns (Clontech, Palo Alto, Calif.). Synthetic RNA substrates were end-labeled with 32P using T4 polynucleotide kinase and incubated with 0.05¾5 uM HBP23 or scrambled DNA enzyme. Reactions were allowed to proceed at 37° C. and were "quenched" by transfer of aliquots to tubes containing 90% formamide, 20 mM EDTA and loading dye. Samples were separated by electrophoresis on 15% TBE-urea denaturing polyacrylamide gels and detected by autoradiography at −80° C. Primary rat fetal cardiomyocytes were obtained from Clonetic (USA) and grown in medium containing 2% FCS, 100 ug/ml streptomycin and 100 IU/ml penicillin at 37° C. in a humidified atmosphere of 5% CO2. Cells were used in experiments between passage 6 and 8. Subconfluent (70-80%) rat fetal cardiomyocytes were transfected using 0.5 ml of serum-free medium containing 0.05¾5 uM HBP23 or scrambled DNA enzyme and 20 ug/ml cationic lipids (DOTAP). After incubation for eight hours cells were lysed using Trizol reagent (Life-Sciences, CA) to isolate RNA for RT-PCR of HBP23 expression, as above.

REFERENCES

1. MacLellan W R and Schneider M D. Genetic dissection of cardiac growth control pathways Annu. Rev. Physiol. 2000. 62:289-320.

2. Soonpaa M H, Field L J. Assessment of cardiomyocyte DNA synthesis in normal and injured adult mouse hearts. Am J Physiol 272, H220-6 (1997).
3. Kellerman S, Moore J A, Zierhut W, Zimmer H G, Campbell J, Gerdes A M. Nuclear DNA content and nucleation patterns in rat cardiac myocytes from different models of cardiac hypertrophy. J Mol Cell Cardiol 24, 497-505 (1992).
4. Colucci, W. S. Molecular and cellular mechanisms of myocardial failure. Am. J. Cardiol. 80(11A), 15L-25L (1997).
5. Ravichandran, L. V. and Puvanakrishnan, R. In vivo labeling studies on the biosynthesis and degradation of collagen in experimental myocardial myocardial infarction. Biochem. Intl. 24, 405-414 (1991).
6. Agocha, A., Lee, H. W., Eghali-Webb, M. Hypoxia regulates basal and induced DNA synthesis and collagen type I production in human cardiac fibroblasts: effects of TGF-beta, thyroid hormone, angiotensis II and basic fibroblast growth factor. J. Mol. Cell. Cardiol. 29, 2233-2244 (1997).
7. Pfeffer, J. M., Pfeffer, M. A, Fletcher, P. J., Braunwald, E. Progressive ventricular remodeling in rat with myocardial infarction. Am. J. Physiol. 260, H1406-414 (1991).
8. Kajstura J, Leri A, Finato N, di Loreto N, Beltramo C A, Anversa P. Myocyte proliferation in end-stage cardiac failure in humans. Proc Natl Acad Sci USA 95, 8801-8805 (1998).
9. Beltrami A P, et al. Evidence that human cardiac myocytes divide after myocardial infarction. N Engl J Med 344, 1750-7 (2001).
10. Kocher, A A, et al. Neovascularization of ischemic myocardium by human bone-marrow-derived angioblasts prevents cardiomyocyte apoptosis, reduces remodeling and improves cardiac function. Nat. Med. 7, 430-6 (2001).
11. Vander Heiden M G, Plas D R, Rathmell J C, Fox C J, Harris M H, Thompson C B. Growth factors can influence cell survival through effects on glucose metabolism. Mol Cell Biol 21, 5899-5912 (2001).
12. Rössig L, Jadidi A S, Urbich C, Badorff C, Zeiher A M, and Dimmeler S. Akt-dependent phosphorylation of p21Cip1 regulates PCNA binding and proliferation of endothelial cells. Mol Cell Biol 21, 5644-5657 (2001).
13. Hill M F, Singal P K. Antioxidant and oxidative stress changes during heart failure subsequent to myocardial infarction in rats. Am J Pathol. 148, 291-300 (1996).
14. Hill M F, Singal P K. Right and left myocardial antioxidant responses during heart failure subsequent to myocardial infarction. Circulation 96, 2414-20 (1997).
15. Cesselli D, et al. Oxidative stress-mediated cardiac cell death is a major determinant of ventricular dysfunction and failure in dog dilated cardiomyopathy. Circ Res 89, 279-86 (2001).
16. Chae, H. Z., Chung, S. J. & Rhee, S. G. Thioredoxin-dependent peroxide reductase from yeast. J. Biol. Chem. 269, 27670-27678 (1994).
17. Das K C, Pahl P M, Guo X-L, and White C W. Induction of peroxiredoxin gene expression by oxygen in lungs of newborn primates. Am. J. Respir. Cell Mol. Biol., 25, 226-232, 2001.
18. Holmgren, A. Thioredoxin. Annu. Rev. Biochem. 54, 237-271 (1985).
19. Sun X, et al. Activation of the cytoplasmic c-Abl tyrosine kinase by reactive oxygen species. J Biol. Chem. 275, 17237-17240 (2000).
20. Kumar S, et al. Targeting of the c-Abl tyrosine kinase to mitochondria in the necrotic cell death response to oxidative stress. J. Biol. Chem. 276, 17281-17285 (2001).
21. Wen S-T, and Van Etten, R A. The PAG gene product, a stress-induced protein with antioxidant properties, is an Abl SH3-binding protein and a physiological inhibitor of c-Abl tyrosine kinase activity. Genes and Development 19, 2456-2467 (1997).
22. Breaker, R. R. Making catalytic DNAs. Science 290, 2095-2096 (2000).
23. Khachigian, L. M. Catalytic DNAs as potential therapeutic agents and sequence-specific molecular tools to dissect biological function. J Clin Invest 106, 1189-1195 (2000).
24. Zuker, M. On finding all suboptimal foldings of an RNA molecule. Science 244, 48-52 (1989).
25. Li B, Ishii T, Choon Ping Tan C P, Soh J W, and Goff S P. Pathways of induction of Peroxiredoxin I expression in osteoblasts. Roles of p38 mitogen-activated protein kinase and protein kinase c. J. Biol. Chem., 277, 12418-12422 (2002).
26. Wert M M and Palfrey H C. Divergence in the anti-apoptotic signalling pathways used awareness by nerve growth factor and basic fibroblast growth factor (bFGF) in PC12 cells: rescue by bFGF involves protein kinase Cd. Biochem. J. 352:175-182 (2000).
27. Chae, H. Z., Chung, S. J. & Rhee, S. G. J. Biol. Chem. 269, 27670-27678 (1994).
28. Kwon, S. J., Park, J., Choi, W., Kim, I. H. & Kim, K. Biochem. Biophys. Res. Comm. 201, 8-15 (1994).
29. Kang, S. W., Baines, I. C. & Rhee, S. G. J. Biol. Chem. 273, 6303-6311 (1998).
30. Wen S-T, and Van Etten, R A. The PAG gene product, a stress-induced protein with antioxidant properties, is an Abl SH3-binding protein and a physiological inhibitor of c-Abl tyrosine kinase activity. Genes and Development 19, 2456-2467 (1997).
31. Kharbanda, S., Yuan, Z. M., Weichselbaum, R. and Kufe, D. Determination of cell fate by c-Abl activation in the response to DNA damage. Oncogene 17, 3309-3318 (1998).
32. Yuan Z M, Huang Y, Whang Y, Sawyers C, Weichselbaum R, Kharbanda S, and Kufe D. Role for c-Abl tyrosine kinase in growth arrest response to DNA damage. Nature 382, 272-4 (1996).
33. Anversa P and Nadal-Ginard B. Myocyte renewal and ventricular remodelling Nature 415, 240-243 (2002).

What is claimed is:

1. A method of treating a subject suffering from a disorder of a heart tissue involving loss or apoptosis of cardiomyocytes which comprises intramyocardially or intracoronarily administering to the subject an amount of an agent comprising a human stromal derived factor-1 effective to induce regeneration of endogenous cardiomyocytes and thereby treat the disorder of the heart tissue involving loss or apopotosis of cardiomyocytes in the subject, wherein the agent increases number of cycling cardiomyocytes.

2. The method of claim 1, wherein the agent is administered intramyocardially or intracoronarily via (a) a stent, (b) a scaffold, or (c) a slow-release formulation.

3. The method of claim 1, wherein the agent is administered intramyocardially.

4. The method of claim 3, wherein the agent is administered intramyocardially by direct injection into a myocardium.

5. The method of claim 1, wherein the human stromal-derived factor-1 is human stromal-derived factor-1α.

6. The method of claim 1, wherein the human stromal-derived factor-1 is human stromal-derived factor-1β.

7. The method of claim 1, wherein the disorder of the heart tissue comprises myocardial infarction, congestive heart failure, chronic ischemia, ischemic disease, diabetic heart disease or cardiomyopathy.

8. The method of claim 1, wherein the disorder of the heart tissue comprises ischemic disease.

9. The method of claim 1, wherein the treatment of the disorder of the heart tissue results in an improved ejection fraction of the heart.

* * * * *

SEQUENCE LISTING

<160> NUMBER OF SEQ ID NOS: 11

<210> SEQ ID NO 1
<211> LENGTH: 2780
<212> TYPE: DNA
<213> ORGANISM: HOMO SAPIENS

<400> SEQUENCE: 1

```
aaactaaccc ctctttttct ccaaaggagt gcttgtggag atcggatctt ttctccagca      60 attggggaa agaaggcttt ttctctgact tcgcttagtg taaccagcgg cgtatatttt     120
ttaggcgcct tttcgaaaac ctagtagtta atattcattt gtttaaatct tatttattt     180 ttaagctcaa actgcttaag aataccttaa ttccttaaag tgaaataatt ttttgcaaag    240
gggtttcctc gatttggagc ttttttttc ttccaccgtc atttctaact cttaaaacca    300
actcagttcc atcatggtga tgttcaagaa gatcaagtct tttgaggtgg tctttaacga    360
ccctgaaaag gtgtacggca gtggcgagaa ggtggctggc cgggtgatag tggaggtgtg    420
tgaagttact cgtgtcaaag ccgttaggat cctggcttgc ggagtggcta aagtgctttg    480
gatgcaggga tcccagcagt gcaaacagac ttcggagtac ctgcgctatg aagacacgct    540
tcttctggaa gaccagccaa caggtgagaa tgagatggtg atcatgagac ctggaaacaa    600
atatgagtac aagttcggct ttgagcttcc tcagggggcct ctgggaacat ccttcaaagg    660
aaaatatggg tgtgtagact actgggtgaa ggcttttctt gaccgcccga gccagccaac    720
tcaagagaca aagaaaaact ttgaagtagt ggatctggtg gatgtcaata cccctgattt    780
aatggcacct gtgtctgcta aaaagaaaa gaaagtttcc tgcatgttca ttcctgatgg    840
gcgggtgtct gtctctgctc gaattgacag aaaaggattc tgtgaaggtg atgagatttc    900
catccatgct gactttgaga atacatgttc ccgaattgtg gtcccaaag ctgccattgt    960 ggcccgccac acttaccttg ccaatggcca gaccaaggtg ctgactcaga agttgtcatc   1020
agtcagaggc aatcatatta tctcagggac atgcgcatca tggcgtggca agagccttcg   1080
ggttcagaag atcaggcctt ctatcctggg ctgcaacatc cttcgagttg aatattcctt   1140
actgatctat gttagcgttc ctggatccaa gaaggtcatc cttgacctgc ccctggtaat   1200
tggcagcaga tcaggtctaa gcagcagaac atccagcatg ccagccgaa ccagctctga   1260 gatgagttgg gtagatctga acatccctga taccccagaa gctcctccct gctatatgga   1320
tgtcattcct gaagatcacc gattggagag cccaaccact cctctgctag atgacatgga   1380
tggctctcaa gacagcccta tctttatgta tgcccctgag ttcaagttca tgccaccacc   1440
gacttatact gaggtggatc cctgcatcct caacaacaat gtgcagtgag catgtggaag   1500
aaaagaagca gctttaccta cttgtttctt tttgtctctc ttcctggaca ctcactttt    1560 cagagactca acagtctctg caatggagtg tgggtccacc ttagcctctg acttcctaat   1620
gtaggaggtg gtcagcaggc aatctcctgg gccttaaagg atgcggactc atcctcagcc   1680
agcgcccatg ttgtgataca ggggtgtttg ttggatgggt ttaaaaataa ctagaaaaac   1740
tcaggcccat ccattttctc agatctcctt gaaaattgag gccttttcga tagtttcggg   1800
tcaggtaaaa atggcctcct ggcgtaagct tttcaaggtt ttttggaggc ttttttgtaaa  1860 ttgtgatagg aactttggac cttgaactta cgtatcatgt ggagaagagc caatttaaca   1920
aactaggaag atgaaaaggg aaattgtggc caaaactttg ggaaaggag gttcttaaaa   1980 tcagtgtttc ccctttgtgc acttgtagaa aaaaagaaa aaccttctag agctgatttg   2040
atggacaatg gagagagctt tccctgtgat tataaaaaag gaagctagct gctctacggt   2100
catctttgct taagagtata ctttaacctg gcttttaaag cagtagtaac tgccccacca   2160
aaggtcttaa aagccatttt tggagcctat tgcactgtgt tctcctactg caaatatttt   2220
catatgggag gatggttttc tcttcatgta agtccttgga attgattcta aggtgatgtt   2280
cttagcactt taattcctgt caaatttttt gttctcccct tctgccatct taaatgtaag   2340
```

```
ctgaaactgg tctactgtgt ctctagggtt aagccaaaag acaaaaaaaa ttttactact    2400
tttgagattg ccccaatgta cagaattata taattctaac gcttaaatca tgtgaaaggg    2460
ttgctgctgt cagccttgcc cactgtgact tcaaacccaa ggaggaactc ttgatcaaga    2520
tgcccaaccc tgtgatcaga acctccaaat actgccatga gaaactagag ggcaggtctt    2580
cataaaagcc ctttgaaccc ccttcctgcc ctgtgttagg agatagggat attggcccct    2640
cactgcagct gccagcactt ggtcagtcac tctcagccat agcactttgt tcactgtcct    2700
gtgtcagagc actgagctcc acccttttct gagagttatt acagccagaa agtgtgggct    2760
gaagatggtt ggtttcatgt                                                2780

<210> SEQ ID NO 2
<211> LENGTH: 391
<212> TYPE: PRT
<213> ORGANISM: HOMO SAPIENS

<400> SEQUENCE: 2

Met Val Met Phe Lys Lys Ile Lys Ser Phe Glu Val Val Phe Asn Asp
1               5                   10                  15

Pro Glu Lys Val Tyr Gly Ser Gly Glu Lys Val Ala Gly Arg Val Ile
            20                  25                  30

Val Glu Val Cys Glu Val Thr Arg Val Lys Ala Val Arg Ile Leu Ala
        35                  40                  45

Cys Gly Val Ala Lys Val Leu Trp Met Gln Gly Ser Gln Gln Cys Lys
    50                  55                  60

Gln Thr Ser Glu Tyr Leu Arg Tyr Glu Asp Thr Leu Leu Leu Glu Asp
65                  70                  75                  80

Gln Pro Thr Gly Glu Asn Glu Met Val Ile Met Arg Pro Gly Asn Lys
                85                  90                  95

Tyr Glu Tyr Lys Phe Gly Phe Glu Leu Pro Gln Gly Pro Leu Gly Thr
            100                 105                 110

Ser Phe Lys Gly Lys Tyr Gly Cys Val Asp Tyr Trp Val Lys Ala Phe
        115                 120                 125

Leu Asp Arg Pro Ser Gln Pro Thr Gln Glu Thr Lys Lys Asn Phe Glu
    130                 135                 140

Val Val Asp Leu Val Asp Val Asn Thr Pro Asp Leu Met Ala Pro Val
145                 150                 155                 160

Ser Ala Lys Lys Glu Lys Lys Val Ser Cys Met Phe Ile Pro Asp Gly
                165                 170                 175

Arg Val Ser Val Ser Ala Arg Ile Asp Arg Lys Gly Phe Cys Glu Gly
            180                 185                 190

Asp Glu Ile Ser Ile His Ala Asp Phe Glu Asn Thr Cys Ser Arg Ile
        195                 200                 205

Val Val Pro Lys Ala Ala Ile Val Ala Arg His Thr Tyr Leu Ala Asn
    210                 215                 220

Gly Gln Thr Lys Val Leu Thr Gln Lys Leu Ser Ser Val Arg Gly Asn
225                 230                 235                 240

His Ile Ile Ser Gly Thr Cys Ala Ser Trp Arg Gly Lys Ser Leu Arg
                245                 250                 255

Val Gln Lys Ile Arg Pro Ser Ile Leu Gly Cys Asn Ile Leu Arg Val
            260                 265                 270

Glu Tyr Ser Leu Leu Ile Tyr Val Ser Val Pro Gly Ser Lys Lys Val
        275                 280                 285

Ile Leu Asp Leu Pro Leu Val Ile Gly Ser Arg Ser Gly Leu Ser Ser
```

```
            290                 295                 300
Arg Thr Ser Ser Met Ala Ser Arg Thr Ser Ser Glu Met Ser Trp Val
305                 310                 315                 320

Asp Leu Asn Ile Pro Asp Thr Pro Glu Ala Pro Pro Cys Tyr Met Asp
                325                 330                 335

Val Ile Pro Glu Asp His Arg Leu Glu Ser Pro Thr Thr Pro Leu Leu
                340                 345                 350

Asp Asp Met Asp Gly Ser Gln Asp Ser Pro Ile Phe Met Tyr Ala Pro
            355                 360                 365

Glu Phe Lys Phe Met Pro Pro Pro Thr Tyr Thr Glu Val Asp Pro Cys
    370                 375                 380

Ile Leu Asn Asn Asn Val Gln
385                 390

<210> SEQ ID NO 3
<211> LENGTH: 1176
<212> TYPE: DNA
<213> ORGANISM: HOMO SAPIENS

<400> SEQUENCE: 3
atggtgatgt tcaagaagat caagtctttt gaggtggtct ttaacgaccc tgaaaaggtg      60
tacggcagtg cgagaaggt ggctggccgg gtgatagtgg aggtgtgtga agttactcgt     120
gtcaaagccg ttaggatcct ggcttgcgga gtggctaaag tgctttggat gcagggatcc     180
cagcagtgca acagacttc ggagtacctg cgctatgaag acacgcttct tctggaagac     240
cagccaacag gtgagaatga tggtgatc atgagacctg aaacaaata tgagtacaag     300 ttcggctttg agcttcctca ggggcctctg gaacatcct tcaaaggaaa atatgggtgt     360
gtagactact gggtgaaggc ttttcttgac cgcccgagcc agccaactca agagacaaag     420 aaaaacttg aagtagtgga tctggtggat gtcaataccc ctgatttaat ggcacctgtg     480
tctgctaaaa aagaaaagaa agtttcctgc atgttcattc ctgatgggcg ggtgtctgtc     540
tctgctcgaa ttgacagaaa aggattctgt gaaggtgatg agatttccat ccatgctgac     600
tttgagaata catgttcccg aattgtggtc cccaaagctg ccattgtggc ccgccacact     660
taccttgcca atggccagac caaggtgctg actcagaagt tgtcatcagt cagaggcaat     720
catattatct cagggacatg cgcatcatgg cgtggcaaga gccttcgggt tcagaagatc     780
aggccttcta tcctgggctg caacatcctt cgagttgaat attccttact gatctatgtt     840
agcgttcctg gatccaagaa ggtcatcctt gacctgcccc tggtaattgg cagcagatca     900
ggtctaagca gcagaacatc cagcatggcc agccgaacca gctctgagat gagttgggta     960
gatctgaaca tccctgatac cccagaagct cctccctgct atatgggtgt cattcctgaa    1020
gatcaccgat ggagagccc aaccactcct ctgctagatg acatggatgg ctctcaagac    1080
agccctatct ttatgtatgc ccctgagttc aagttcatgc caccaccgac ttatactgag    1140
gtggatccct gcatcctcaa caacaatgtg cagtga                              1176

<210> SEQ ID NO 4
<211> LENGTH: 20
<212> TYPE: DNA
<213> ORGANISM: ARTIFICIAL SEQUENCE
<220> FEATURE:
<223> OTHER INFORMATION: PRIMER DIRETCTED TO RAT Cinc

<400> SEQUENCE: 4
gaagatagat tgcaccgatg                                                   20
```

<210> SEQ ID NO 5
<211> LENGTH: 18
<212> TYPE: DNA
<213> ORGANISM: ARTIFICIAL SEQUENCE
<220> FEATURE:
<223> OTHER INFORMATION: PRIMER DIRETCTED TO RAT Cinc

<400> SEQUENCE: 5
catagcctct cacatttc                                                18

<210> SEQ ID NO 6
<211> LENGTH: 25
<212> TYPE: DNA
<213> ORGANISM: ARTIFICIAL SEQUENCE
<220> FEATURE:
<223> OTHER INFORMATION: PRIMER DIRETCTED TO RAT Cinc

<400> SEQUENCE: 6
gcgcccgtcc gccaatgagc tgcgc                                        25

<210> SEQ ID NO 7
<211> LENGTH: 28
<212> TYPE: DNA
<213> ORGANISM: ARTIFICIAL SEQUENCE
<220> FEATURE:
<223> OTHER INFORMATION: PRIMER DIRETCTED TO RAT Cinc

<400> SEQUENCE: 7
cttggggaca cccttcagca tcttttgg                                     28

<210> SEQ ID NO 8
<211> LENGTH: 21
<212> TYPE: DNA
<213> ORGANISM: ARTIFICIAL SEQUENCE
<220> FEATURE:
<223> OTHER INFORMATION: PRIMER DIRETCTED TO RAT Cinc

<400> SEQUENCE: 8
ctctacccac ggcaagttca a                                            21

<210> SEQ ID NO 9
<211> LENGTH: 20
<212> TYPE: DNA
<213> ORGANISM: ARTIFICIAL SEQUENCE
<220> FEATURE:
<223> OTHER INFORMATION: PRIMER DIRETCTED TO RAT Cinc

<400> SEQUENCE: 9
gggatgacct tgcccacagc                                              20

<210> SEQ ID NO 10
<211> LENGTH: 34
<212> TYPE: DNA
<213> ORGANISM: ARTIFICIAL SEQUENCE
<220> FEATURE:
<223> OTHER INFORMATION: PRIMER DIRECTED TO RAT HBP23

<400> SEQUENCE: 10
tttaccctct tgactttact tttgtgtgtc ccac                              34

<210> SEQ ID NO 11
<211> LENGTH: 23
<212> TYPE: DNA
<213> ORGANISM: ARTIFICIAL SEQUENCE
<220> FEATURE:
<223> OTHER INFORMATION: PRIMER DIRECTED TO RAT HBP23

```
<400> SEQUENCE: 11
ccagctgggc acacttcacc atg                                              23
```